US012799478B2

(12) United States Patent
Nedialkova et al.

(10) Patent No.: US 12,799,478 B2
(45) Date of Patent: Nov. 17, 2026

(54) METHOD FOR cDNA LIBRARY CONSTRUCTION AND ANALYSIS FROM TRANSFER RNA

(71) Applicant: Max-Planck-Gesellschaft zur Förderung der Wissenschaften e.V., Munich (DE)

(72) Inventors: Danny D. Nedialkova, Gräfelfing (DE); Andrew Behrens, Munich (DE); Geraldine Rodschinka, Munich (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 195 days.

(21) Appl. No.: 18/684,644

(22) PCT Filed: Aug. 18, 2021

(86) PCT No.: PCT/EP2021/072902
§ 371 (c)(1),
(2) Date: Feb. 16, 2024

(87) PCT Pub. No.: WO2023/020688
PCT Pub. Date: Feb. 23, 2023

(65) Prior Publication Data
US 2026/0117220 A1 Apr. 30, 2026

(51) Int. Cl.
*C12N 15/10* (2006.01)

(52) U.S. Cl.
CPC ..... *C12N 15/1068* (2013.01); *C12N 15/1089* (2013.01)

(58) Field of Classification Search
CPC ....................................................... C12Q 1/68
See application file for complete search history.

(56) References Cited

PUBLICATIONS

Wu, High-Throughput Sequencing with Thermostable Group II Intron Reverse Transcriptases, Dissertation, University of Texas, May 2019.*

(Continued)

*Primary Examiner* — Yung-Sheng M Tsui
(74) *Attorney, Agent, or Firm* — Pillsbury Winthrop Shaw Pittman LLP

(57) ABSTRACT

The present invention relates to a method for the generation of a cDNA library from transfer RNA (tRNA) comprising (a) optionally ligating at least one DNA adapter to 3'-end of tRNA, wherein 3'-end of the DNA adapter is preferably a chain terminator dideoxycytidine, preferably under one or more of the following conditions: (i) crowding reagent at 5% to 35%, preferably 15% to 30%, and most preferably about 25%, (ii) $MgCl_2$ concentration of 1 mM to 15 mM, preferably 3 to 12 mM and most preferably about 10 mM (iii) a temperature of 12 °C to 37 °C, preferably of about 25 °C (iv) a pH of 6.0 to 9.0, preferably 6.5 to 8.0 and most preferably about 7.0, (v) reducing agent concentration of 0.1 mM to 10 mM, preferably 0.5 to 5 mM and most preferably about 1 mM, and (vi) a reaction time of at least 30 min, preferably at least 1.5 h and most preferably at least 3 h; and (b) reverse transcription in a primer-dependent reaction, in case step (a) is present, or in a template-switching reaction, in case step (a) is absent, of tRNAs into cDNA by a group II intron reverse transcriptase, under the following conditions: (i) KCl or NaCl at a concentration of 20 mM to 250 mM, preferably 50 to 100 mM and most preferably about 75 mM, (ii) $MgCl_2$ at a concentration of 0.5 mM to 15 mM, preferably 1 to 5 mM and most preferably about 3 mM, (iii) a temperature of 30 °C to 65 °C, preferably of about 42 °C, and (iv) a reaction time of at least 2 h, preferably at least 8 h and most preferably at least 15 h, and preferably (v) a pH of 6.5 to 9.5, preferably 7.0 to 8.5 and most preferably about 8.0, and/or (vi) a reducing agent (DTT) at a concentration of (Continued)

Figures 1A, 1B:
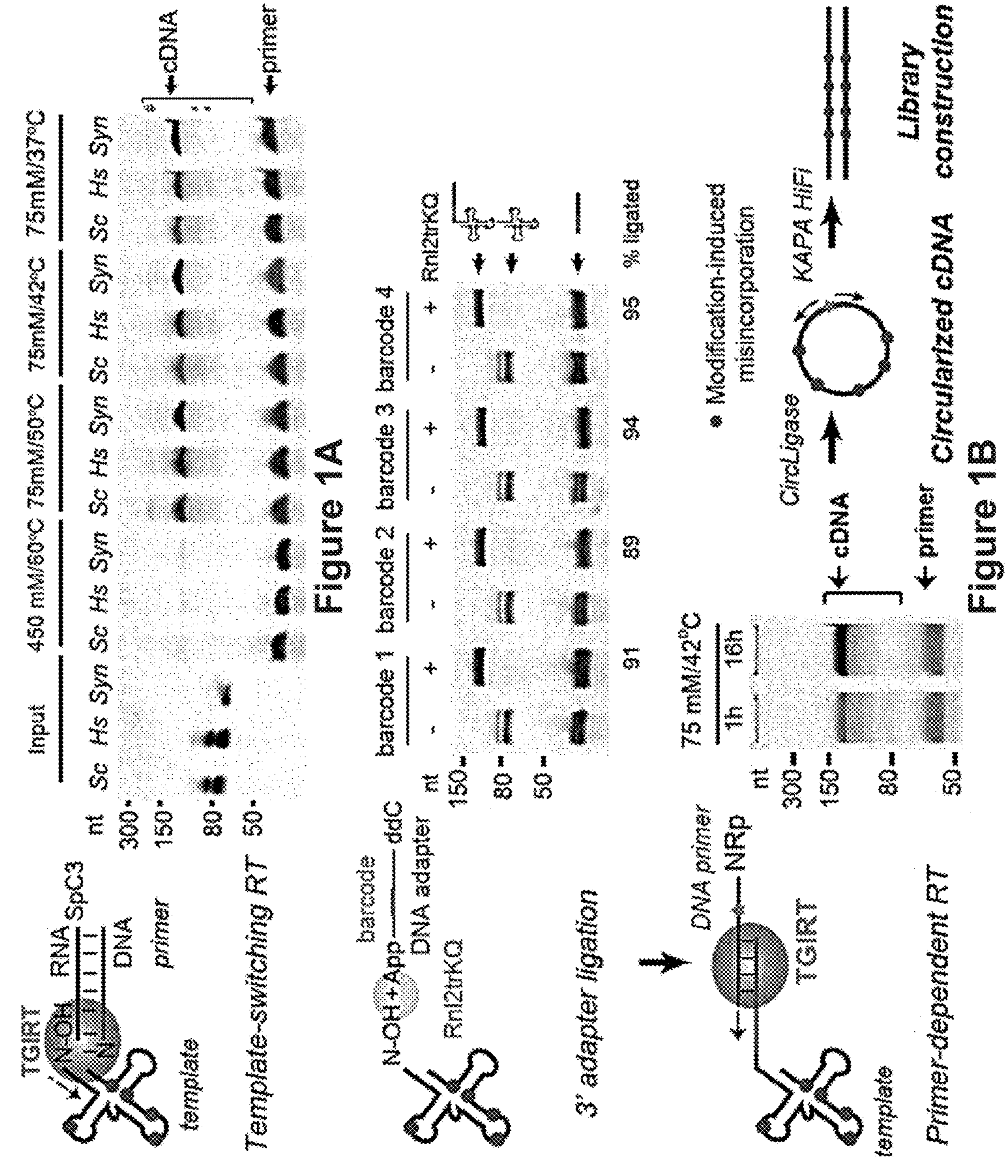

1 mM to 12.5 mM, preferably 3 to 8 mM and most preferably about 5 mM.

15 Claims, 13 Drawing Sheets

Specification includes a Sequence Listing.

(56) References Cited

PUBLICATIONS

Qin et al, High-throughput sequencing of human plasma RNA by using thermostable group II intron reverse transcriptases, RNA. Jan. 2016;22(1):111-128. doi: 10.1261/rna.054809.115.*
Cozen et al., "ARM-seq: AlkB-facilitated RNA methylation sequencing reveals a complex landscape of modified tRNA fragments", Nature Methods, Aug. 3, 2015, pp. 879-884, vol. 12(9).
Evans et al., "Determination of tRNA aminoacylation levels by high-throughput sequencing", Nucleic Acids Research, Jun. 6, 2017, pp. 1-8, e133, vol. 45(14).
Gogakos et al., "Characterizing Expression and Processing of Precursor and Mature Human tRNAs by HydrotRNAseq and PAR-CLIP", Cell Reports, Aug. 8, 2017, pp. 1463-1475, vol. 20.
Hoffmann et al., "Accurate mapping of tRNA reads", Bioinformatics, Dec. 8, 2017, pp. 1116-1124.
Mohr et al., "Thermostable group II intron reverse transcriptase fusion proteins and their use in cDNA synthesis and next-generation RNA sequencing", RNA, 2013, pp. 958-970, vol. 19.
Pinkard et al., "Quantitative tRNA-sequencing uncovers metazoan tissue-specific tRNA regulation", Nature Communications, 2020, pp. 4104-4115, vol. 11.
Zhao et al., "An ultraprocessive, accurate reverse transcriptase encoded by a metazoan group II intron", RNA, 2018, pp. 183-195, vol. 24.
Zheng et al., "Efficient and quantitative high-throughput tRNA sequencing", Nature Methods, Jul. 27, 2015, pp. 835-839, vol. 12(9).
Zhuang et al., "Structural bias in T4 RNA ligase-mediated 3'-adapter ligation", Nucleic Acids Research, Jan. 12, 2012, pp. 1-14, e54, vol. 40(7).
Patent Cooperation Treaty, International Search Report and Written Opinion issued in PCT/EP2021/072902, May 13, 2022, pp. 1-16.
Behrens et al., "High-resolution 1-15 quantitative profiling of tRNA abundance and modification status in eukaryotes by mim-tRNAseq", Molecular Cell, Elsevier, Feb. 12, 2021, pp. 1802-1815, e1-e7, vol. 81(8).
Pinkard et al., "Quantitative tRNA-sequencing uncovers metazoan tissue-specific tRNA regulation", Nature Communications, Dec. 1, 2020, pp. 1-15, vol. 11(1).
Gogakos, et al., "Characterizing Expression and Processing of Precursor and Mature Human tRNAs by Hydro-tRNAseq and PAR-CLIP", Cell Reports, Aug. 1, 2017, pp. 1463-1475, vol. 20(6).
Clark et al., "tRNA base methylation identification and quantification via high-throughput sequencing", RNA, Nov. 1, 2016, pp. 1771-1784, vol. 22(11).
Cozen et al., "ARM-seq: AlkB-facilitated RNA methylation sequencing reveals a complex landscape of modified tRNA fragments", Nature Methods, Sep. 1, 2015, pp. 879-884, vol. 12(9).
Wu, Ching Kai Douglas, "High-throughput sequencing with thermostable group II intron reverse transcriptases", Doctoral Dissertation, May 1, 2019, pp. 1-255.
Zhao Chen et al: "An ultraprocessive, accurate reverse transcriptase encoded by a metazoan group II intron", RNA, Feb. 1, 2018, pp. 183-195, vol. 24.

* cited by examiner

```
                          SEQUENCE LISTING


<160> NUMBER OF SEQ ID NOS: 25

<210> SEQ ID NO 1
<211> LENGTH: 562
<212> TYPE: PRT
<213> ORGANISM: Thermosynechococcus elongatus

<400> SEQUENCE: 1

Met Glu Thr Arg Gln Met Thr Val Asp Gln Thr Thr Gly Ala Val Thr
1               5                   10                  15

Asn Gln Thr Glu Thr Ser Trp His Ser Ile Asn Trp Thr Lys Ala Asn
            20                  25                  30

Arg Glu Val Lys Arg Leu Gln Val Arg Ile Ala Lys Ala Val Lys Glu
        35                  40                  45

Gly Arg Trp Gly Lys Val Lys Ala Leu Gln Trp Leu Leu Thr His Ser
    50                  55                  60

Phe Tyr Gly Lys Ala Leu Ala Val Lys Arg Val Thr Asp Asn Ser Gly
65                  70                  75                  80

Ser Arg Thr Pro Gly Val Asp Gly Ile Thr Trp Ser Thr Gln Glu Gln
                85                  90                  95

Lys Thr Gln Ala Ile Lys Ser Leu Arg Arg Arg Gly Tyr Lys Pro Gln
            100                 105                 110

Pro Leu Arg Arg Val Tyr Ile Pro Lys Ala Asn Gly Lys Gln Arg Pro
        115                 120                 125

Leu Gly Ile Pro Thr Met Lys Asp Arg Ala Met Gln Ala Leu Tyr Ala
    130                 135                 140

Leu Ala Leu Glu Pro Val Ala Glu Thr Thr Ala Asp Arg Asn Ser Tyr
145                 150                 155                 160

Gly Phe Arg Arg Gly Arg Cys Thr Ala Asp Ala Ala Gly Gln Cys Phe
                165                 170                 175

Leu Ala Leu Ala Lys Ala Lys Ser Ala Glu His Val Leu Asp Ala Asp
            180                 185                 190

Ile Ser Gly Cys Phe Asp Asn Ile Ser His Glu Trp Leu Leu Ala Asn
        195                 200                 205

Thr Pro Leu Asp Lys Gly Ile Leu Arg Lys Trp Leu Lys Ser Gly Phe
    210                 215                 220

Val Trp Lys Gln Gln Leu Phe Pro Thr His Ala Gly Thr Pro Gln Gly
225                 230                 235                 240

Gly Val Ile Ser Pro Val Leu Ala Asn Ile Thr Leu Asp Gly Met Glu
                245                 250                 255

Glu Leu Leu Ala Lys His Leu Arg Gly Gln Lys Val Asn Leu Ile Arg
            260                 265                 270

Tyr Ala Asp Asp Phe Val Val Thr Gly Lys Asp Glu Glu Thr Leu Glu
        275                 280                 285

Lys Ala Arg Asn Leu Ile Gln Glu Phe Leu Lys Glu Arg Gly Leu Thr
```

```
    290                 295                 300

Leu Ser Pro Glu Lys Thr Lys Ile Val His Ile Glu Glu Gly Phe Asp
305                 310                 315                 320

Phe Leu Gly Trp Asn Ile Arg Lys Tyr Asn Gly Val Leu Leu Ile Lys
                325                 330                 335

Pro Ala Lys Lys Asn Val Lys Ala Phe Leu Lys Lys Ile Arg Asp Thr
            340                 345                 350

Leu Arg Glu Leu Arg Thr Ala Thr Gln Glu Ile Val Ile Asp Thr Leu
        355                 360                 365

Asn Pro Ile Ile Arg Gly Trp Ala Asn Tyr His Lys Gly Gln Val Ser
    370                 375                 380

Lys Glu Thr Phe Asn Arg Val Asp Phe Ala Thr Trp His Lys Leu Trp
385                 390                 395                 400

Arg Trp Ala Arg Arg Arg His Pro Asn Lys Pro Ala Gln Trp Val Lys
                405                 410                 415

Asp Lys Tyr Phe Ile Lys Asn Gly Ser Arg Asp Trp Val Phe Gly Met
            420                 425                 430

Val Met Lys Asp Lys Asn Gly Glu Leu Arg Thr Lys Arg Leu Ile Lys
        435                 440                 445

Thr Ser Asp Thr Arg Ile Gln Arg His Val Lys Ile Lys Ala Asp Ala
    450                 455                 460

Asn Pro Phe Leu Pro Glu Trp Ala Glu Tyr Phe Glu Lys Arg Lys Lys
465                 470                 475                 480

Leu Lys Lys Ala Pro Ala Gln Tyr Arg Arg Ile Arg Arg Glu Leu Trp
                485                 490                 495

Lys Lys Gln Gly Gly Ile Cys Pro Val Cys Gly Gly Glu Ile Glu Gln
            500                 505                 510

Asp Met Leu Thr Asp Ile His His Ile Leu Pro Lys His Lys Gly Gly
        515                 520                 525

Ser Asp Asp Leu Asp Asn Leu Val Leu Ile His Ala Asn Cys His Lys
    530                 535                 540

Gln Val His Ser Arg Asp Gly Gln His Ser Arg Ser Leu Leu Lys Glu
545                 550                 555                 560

Gly Leu


<210> SEQ ID NO 2
<211> LENGTH: 562
<212> TYPE: PRT
<213> ORGANISM: Thermosynechococcus elongatus

<400> SEQUENCE: 2

Met Glu Thr Arg Gln Met Ala Val Glu Gln Thr Thr Gly Ala Val Thr
1               5                   10                  15

Asn Gln Thr Glu Thr Ser Trp His Ser Ile Asp Trp Ala Lys Ala Asn
            20                  25                  30

Arg Glu Val Lys Arg Leu Gln Val Arg Ile Ala Lys Ala Val Lys Glu
        35                  40                  45

Gly Arg Trp Gly Lys Val Lys Ala Leu Gln Trp Leu Leu Thr His Ser
    50                  55                  60

Phe Tyr Gly Lys Ala Leu Ala Val Lys Arg Val Thr Asp Asn Ser Gly
65                  70                  75                  80

Ser Lys Thr Pro Gly Val Asp Gly Ile Thr Trp Ser Thr Gln Glu Gln
                85                  90                  95

Lys Ala Gln Ala Ile Lys Ser Leu Arg Arg Arg Gly Tyr Lys Pro Gln
```

-continued

```
            100                 105                 110

Pro Leu Arg Arg Val Tyr Ile Pro Lys Ala Asn Gly Lys Gln Arg Pro
        115                 120                 125

Leu Gly Ile Pro Thr Met Lys Asp Arg Ala Met Gln Ala Leu Tyr Ala
    130                 135                 140

Leu Ala Leu Glu Pro Val Ala Glu Thr Thr Ala Asp Arg Asn Ser Tyr
145                 150                 155                 160

Gly Phe Arg Arg Gly Arg Cys Ile Ala Asp Ala Ala Thr Gln Cys His
                165                 170                 175

Ile Thr Leu Ala Lys Thr Asp Arg Ala Gln Tyr Val Leu Asp Ala Asp
            180                 185                 190

Ile Ala Gly Cys Phe Asp Asn Ile Ser His Glu Trp Leu Leu Ala Asn
        195                 200                 205

Ile Pro Leu Asp Lys Arg Ile Leu Arg Lys Trp Leu Lys Ser Gly Phe
    210                 215                 220

Val Trp Lys Gln Gln Leu Phe Pro Ile His Ala Gly Thr Pro Gln Gly
225                 230                 235                 240

Gly Val Ile Ser Pro Met Leu Ala Asn Met Thr Leu Asp Gly Met Glu
                245                 250                 255

Glu Leu Leu Asn Lys Phe Pro Arg Ala His Lys Val Lys Leu Ile Arg
            260                 265                 270

Tyr Ala Asp Asp Phe Val Val Thr Gly Glu Thr Lys Glu Val Leu Tyr
        275                 280                 285

Ile Ala Gly Ala Val Ile Gln Ala Phe Leu Lys Glu Arg Gly Leu Thr
    290                 295                 300

Leu Ser Lys Glu Lys Thr Lys Ile Val His Ile Glu Glu Gly Phe Asp
305                 310                 315                 320

Phe Leu Gly Trp Asn Ile Arg Lys Tyr Asp Gly Lys Leu Leu Ile Lys
                325                 330                 335

Pro Ala Lys Lys Asn Val Lys Ala Phe Leu Lys Lys Ile Arg Asp Thr
            340                 345                 350

Leu Arg Glu Leu Arg Thr Ala Pro Gln Glu Ile Val Ile Asp Thr Leu
        355                 360                 365

Asn Pro Ile Ile Arg Gly Trp Thr Asn Tyr His Lys Asn Gln Ala Ser
    370                 375                 380

Lys Glu Thr Phe Val Gly Val Asp His Leu Ile Trp Gln Lys Leu Trp
385                 390                 395                 400

Arg Trp Ala Arg Arg Arg His Pro Ser Lys Ser Val Arg Trp Val Lys
                405                 410                 415

Ser Lys Tyr Phe Ile Gln Ile Gly Asn Arg Lys Trp Met Phe Gly Ile
            420                 425                 430

Trp Thr Lys Asp Lys Asn Gly Asp Pro Trp Ala Lys His Leu Ile Lys
        435                 440                 445

Ala Ser Glu Ile Arg Ile Gln Arg Arg Gly Lys Ile Lys Ala Asp Ala
    450                 455                 460

Asn Pro Phe Leu Pro Glu Trp Ala Glu Tyr Phe Glu Gln Arg Lys Lys
465                 470                 475                 480

Leu Lys Glu Ala Pro Ala Gln Tyr Arg Arg Thr Arg Arg Glu Leu Trp
                485                 490                 495

Lys Lys Gln Gly Gly Ile Cys Pro Val Cys Gly Gly Glu Ile Glu Gln
            500                 505                 510

Asp Met Leu Thr Glu Ile His His Ile Leu Pro Lys His Lys Gly Gly
        515                 520                 525
```

Thr Asp Asp Leu Asp Asn Leu Val Leu Ile His Thr Asn Cys His Lys
530 535 540

Gln Val His Asn Arg Asp Gly Gln His Ser Arg Phe Leu Leu Lys Glu
545 550 555 560

Gly Leu

<210> SEQ ID NO 3
<211> LENGTH: 562
<212> TYPE: PRT
<213> ORGANISM: Thermosynechococcus elongatus

<400> SEQUENCE: 3

Met Glu Thr Arg Gln Met Ala Val Glu Gln Thr Thr Gly Ala Val Thr
1 5 10 15

Asn Gln Thr Glu Thr Ser Trp His Ser Ile Asp Trp Ala Lys Ala Asn
20 25 30

Arg Glu Val Lys Arg Leu Gln Val Arg Ile Ala Lys Ala Val Lys Glu
35 40 45

Gly Arg Trp Gly Lys Val Lys Ala Leu Gln Trp Leu Leu Thr His Ser
50 55 60

Phe Tyr Gly Lys Ala Leu Ala Val Lys Arg Val Thr Asp Asn Ser Gly
65 70 75 80

Ser Lys Thr Pro Gly Val Asp Gly Ile Thr Trp Ser Thr Gln Glu Gln
85 90 95

Lys Ala Gln Ala Ile Lys Ser Leu Arg Arg Arg Gly Tyr Lys Pro Gln
100 105 110

Pro Leu Arg Arg Val Tyr Ile Pro Lys Ala Ser Gly Lys Gln Arg Pro
115 120 125

Leu Gly Ile Pro Thr Thr Lys Asp Arg Ala Met Gln Ala Leu Tyr Ala
130 135 140

Leu Ala Leu Glu Pro Val Ala Glu Thr Thr Ala Asp Arg Asn Ser Tyr
145 150 155 160

Gly Phe Arg Gln Gly Arg Cys Thr Ala Asp Ala Ala Gly Gln Cys Phe
165 170 175

Thr Val Leu Gly Arg Ser Asp Cys Ala Lys Tyr Ile Leu Asp Ala Asp
180 185 190

Ile Thr Gly Cys Phe Asp Asn Ile Ser His Glu Trp Leu Leu Asp Asn
195 200 205

Ile Pro Leu Asp Lys Glu Val Leu Arg Lys Trp Leu Lys Ser Gly Phe
210 215 220

Val Trp Lys Gln Gln Leu Phe Pro Thr His Ala Gly Thr Pro Gln Gly
225 230 235 240

Gly Val Ile Ser Pro Met Leu Ala Asn Met Thr Leu Asp Gly Met Glu
245 250 255

Glu Leu Leu Lys Lys His Leu Arg Lys Gln Lys Val Asn Leu Ile Arg
260 265 270

Tyr Ala Asp Asp Phe Val Val Thr Gly Glu Ser Lys Glu Thr Leu Glu
275 280 285

Lys Val Thr Thr Val Ile Gln Glu Phe Leu Lys Glu Arg Gly Leu Thr
290 295 300

Leu Ser Glu Glu Lys Thr Lys Val Val His Ile Glu Glu Gly Phe Asp
305 310 315 320

Phe Leu Gly Trp Asn Ile Arg Lys Tyr Gly Glu Lys Leu Leu Ile Lys
325 330 335

```
Pro Ala Lys Lys Asn Ile Lys Ala Phe His Lys Lys Ile Arg Asp Ala
            340                 345                 350

Leu Lys Glu Leu Arg Thr Ala Thr Gln Glu Ala Val Ile Asp Thr Leu
        355                 360                 365

Asn Pro Ile Ile Lys Gly Trp Ala Asn Tyr His Arg Asn Gln Val Ser
    370                 375                 380

Lys Arg Ile Phe Asn Arg Ala Asp Asp Asn Ile Trp His Lys Leu Trp
385                 390                 395                 400

Arg Trp Ala Lys Arg Arg His Pro Asn Lys Pro Ala Arg Trp Thr Lys
                405                 410                 415

Asn Lys Tyr Phe Ile Lys Ile Gly Asn Arg His Trp Val Phe Gly Thr
            420                 425                 430

Trp Lys Lys Asp Lys Glu Gly Arg Leu Arg Ser Arg Tyr Leu Ile Lys
        435                 440                 445

Ala Gly Asp Thr Arg Ile Gln Arg His Val Lys Ile Lys Ala Asp Ala
    450                 455                 460

Asn Pro Phe Leu Pro Glu Trp Ala Glu Tyr Phe Glu Glu Arg Lys Lys
465                 470                 475                 480

Leu Lys Glu Ala Pro Ala Gln Tyr Arg Arg Ile Arg Arg Glu Leu Trp
                485                 490                 495

Lys Lys Gln Gly Gly Ile Cys Pro Val Cys Gly Gly Glu Ile Glu Gln
            500                 505                 510

Asp Met Leu Thr Glu Ile His His Ile Leu Pro Lys His Lys Gly Gly
        515                 520                 525

Ser Asp Asp Leu Asp Asn Leu Val Leu Ile His Ala Asn Cys His Lys
    530                 535                 540

Gln Val His Ser Arg Asp Gly Gln His Ser Arg Phe Leu Leu Lys Glu
545                 550                 555                 560

Gly Leu


<210> SEQ ID NO 4
<211> LENGTH: 635
<212> TYPE: PRT
<213> ORGANISM: Geobacillus stearothermophilus

<400> SEQUENCE: 4

Met Lys Val Asn Lys Leu Val Val Lys Ser Glu Gln Asp Leu Arg Asn
1               5                   10                  15

Cys Leu Asp Leu Leu Tyr Gln Glu Ala Lys Lys Gly Lys His Phe Tyr
            20                  25                  30

Gly Met Leu Glu Leu Leu Gln Asn Asp Val Val Ile Leu Glu Ala Ile
        35                  40                  45

Arg Asn Ile Lys Ser Asn Lys Gly Ser Lys Thr Ala Gly Ile Asp Gln
    50                  55                  60

Lys Ile Val Asp Asp Tyr Leu Leu Met Pro Thr Glu Lys Val Phe Gly
65                  70                  75                  80

Met Ile Lys Ala Lys Leu Asn Asp Tyr Lys Pro Ile Pro Val Arg Arg
                85                  90                  95

Cys Asn Lys Pro Lys Gly Asn Ala Lys Ser Ser Lys Arg Lys Gly Asn
            100                 105                 110

Ser Pro Asn Glu Glu Gly Glu Thr Arg Pro Leu Gly Ile Ser Ala Val
        115                 120                 125

Thr Asp Arg Ile Ile Gln Glu Met Leu Arg Ile Val Leu Glu Pro Ile
    130                 135                 140
```

```
Phe Glu Ala Gln Phe Tyr Pro His Ser Tyr Gly Phe Arg Pro Tyr Arg
145                 150                 155                 160

Ser Thr Glu His Ala Leu Ala Trp Met Leu Lys Ile Ile Asn Gly Ser
                165                 170                 175

Lys Leu Tyr Trp Val Val Lys Gly Asp Ile Glu Ser Tyr Phe Asp His
            180                 185                 190

Ile Asn His Lys Lys Leu Leu Asn Ile Met Trp Asn Met Gly Val Arg
        195                 200                 205

Asp Lys Arg Val Leu Cys Ile Val Lys Lys Met Leu Lys Ala Gly Gln
    210                 215                 220

Val Ile Gln Gly Lys Phe Tyr Pro Thr Ala Lys Gly Ile Pro Gln Gly
225                 230                 235                 240

Gly Ile Ile Ser Pro Leu Leu Ala Asn Val Tyr Leu Asn Ser Phe Asp
                245                 250                 255

Trp Met Val Gly Gln Glu Tyr Glu Tyr His Pro Asn Asn Ala Asn Tyr
            260                 265                 270

Arg Glu Lys Lys Asn Ala Leu Ala Ala Leu Arg Asn Lys Gly His His
        275                 280                 285

Pro Val Phe Tyr Ile Arg Tyr Ala Asp Asp Trp Val Ile Leu Thr Asp
    290                 295                 300

Thr Lys Glu Tyr Ala Glu Lys Ile Arg Glu Gln Cys Lys Gln Tyr Leu
305                 310                 315                 320

Ala Cys Glu Leu His Leu Thr Leu Ser Asp Glu Lys Thr Phe Ile Ala
                325                 330                 335

Asp Ile Arg Glu Gln Arg Val Lys Phe Leu Gly Phe Cys Ile Glu Ala
            340                 345                 350

Gly Lys Arg Arg Phe His Lys Lys Gly Phe Ala Ala Arg Met Ile Pro
        355                 360                 365

Asp Met Glu Lys Val Asn Ala Lys Val Lys Glu Ile Lys Arg Asp Ile
    370                 375                 380

Arg Leu Leu Arg Thr Arg Lys Ser Glu Leu Glu Lys Ala Leu Asp Ile
385                 390                 395                 400

Glu Asn Ile Asn Thr Lys Ile Ile Gly Leu Ala Asn His Leu Lys Ile
                405                 410                 415

Gly Ile Ser Lys Tyr Ile Met Gly Lys Val Asp Arg Val Ile Glu Glu
            420                 425                 430

Thr Ala Tyr Arg Thr Trp Val Lys Met Tyr Gly Lys Glu Lys Ala Ala
        435                 440                 445

Gln Tyr Lys Arg Pro Val Ser Glu Phe His Asn Arg Ile Asp Arg His
    450                 455                 460

Lys Gly Tyr Gln Met Lys His Phe Ser Val Val Thr Glu Asp Gly Ile
465                 470                 475                 480

Arg Val Gly Ile Thr His Ala Lys Ile Thr Pro Ile Gln Tyr Ala Thr
                485                 490                 495

Val Phe Lys Gln Glu Met Thr Pro Tyr Thr Ala Asp Gly Arg Lys Met
            500                 505                 510

Tyr Glu Glu Lys His Arg Lys Ile Arg Leu Pro Asp Lys Met Ser Leu
        515                 520                 525

Phe Asp His Asp Ser Ile Phe Ile Tyr Ile Leu Ser Glu His Asn Asp
    530                 535                 540

Gly Lys Tyr Asn Leu Glu Tyr Phe Leu Asn Arg Val Asn Val Phe His
545                 550                 555                 560
```

```
Arg Asp Lys Gly Lys Cys Lys Ile Cys Ala Val Tyr Leu Ser Pro Gly
                565                 570                 575

Asn Phe His Cys His His Ile Asp Pro Ser Lys Pro Leu Ser Glu Ile
            580                 585                 590

Asn Lys Thr Val Asn Leu Ile Ser Leu Cys Asn Gln Cys His Arg Leu
        595                 600                 605

Val His Ser Asn Gln Glu Pro Pro Phe Thr Glu Arg Lys Met Phe Asp
    610                 615                 620

Lys Leu Thr Lys Tyr Arg Asn Lys Leu Lys Ile
625                 630                 635


<210> SEQ ID NO 5
<211> LENGTH: 420
<212> TYPE: PRT
<213> ORGANISM: Geobacillus stearothermophilus

<400> SEQUENCE: 5

Met Ala Leu Leu Glu Arg Ile Leu Ala Arg Asp Asn Leu Ile Thr Ala
1               5                   10                  15

Leu Lys Arg Val Glu Ala Asn Gln Gly Ala Pro Gly Ile Asp Gly Val
            20                  25                  30

Ser Thr Asp Gln Leu Arg Asp Tyr Ile Arg Ala His Trp Ser Thr Ile
        35                  40                  45

His Ala Gln Leu Leu Ala Gly Thr Tyr Arg Pro Ala Pro Val Arg Arg
    50                  55                  60

Val Glu Ile Pro Lys Pro Gly Gly Gly Thr Arg Gln Leu Gly Ile Pro
65                  70                  75                  80

Thr Val Val Asp Arg Leu Ile Gln Gln Ala Ile Leu Gln Glu Leu Thr
                85                  90                  95

Pro Ile Phe Asp Pro Asp Phe Ser Ser Ser Ser Phe Gly Phe Arg Pro
            100                 105                 110

Gly Arg Asn Ala His Asp Ala Val Arg Gln Ala Gln Gly Tyr Ile Gln
        115                 120                 125

Glu Gly Tyr Arg Tyr Val Val Asp Met Asp Leu Glu Lys Phe Phe Asp
    130                 135                 140

Arg Val Asn His Asp Ile Leu Met Ser Arg Val Ala Arg Lys Val Lys
145                 150                 155                 160

Asp Lys Arg Val Leu Lys Leu Ile Arg Ala Tyr Leu Gln Ala Gly Val
                165                 170                 175

Met Ile Glu Gly Val Lys Val Gln Thr Glu Glu Gly Thr Pro Gln Gly
            180                 185                 190

Gly Pro Leu Ser Pro Leu Leu Ala Asn Ile Leu Leu Asp Asp Leu Asp
        195                 200                 205

Lys Glu Leu Glu Lys Arg Gly Leu Lys Phe Cys Arg Tyr Ala Asp Asp
    210                 215                 220

Cys Asn Ile Tyr Val Lys Ser Leu Arg Ala Gly Gln Arg Val Lys Gln
225                 230                 235                 240

Ser Ile Gln Arg Phe Leu Glu Lys Thr Leu Lys Leu Lys Val Asn Glu
                245                 250                 255

Glu Lys Ser Ala Val Asp Arg Pro Trp Lys Arg Ala Phe Leu Gly Phe
            260                 265                 270

Ser Phe Thr Pro Glu Arg Lys Ala Arg Ile Arg Leu Ala Pro Arg Ser
        275                 280                 285

Ile Gln Arg Leu Lys Gln Arg Ile Arg Gln Leu Thr Asn Pro Asn Trp
    290                 295                 300
```

```
Ser Ile Ser Met Pro Glu Arg Ile His Arg Val Asn Gln Tyr Val Met
305                 310                 315                 320

Gly Trp Ile Gly Tyr Phe Arg Leu Val Glu Thr Pro Ser Val Leu Gln
                325                 330                 335

Thr Ile Glu Gly Trp Ile Arg Arg Arg Leu Arg Leu Cys Gln Trp Leu
            340                 345                 350

Gln Trp Lys Arg Val Arg Thr Arg Ile Arg Glu Leu Arg Ala Leu Gly
        355                 360                 365

Leu Lys Glu Thr Ala Val Met Glu Ile Ala Asn Thr Arg Lys Gly Ala
    370                 375                 380

Trp Arg Thr Thr Lys Thr Pro Gln Leu His Gln Ala Leu Gly Lys Thr
385                 390                 395                 400

Tyr Trp Thr Ala Gln Gly Leu Lys Ser Leu Thr Gln Arg Tyr Phe Glu
                405                 410                 415

Leu Arg Gln Gly
            420


<210> SEQ ID NO 6
<211> LENGTH: 427
<212> TYPE: PRT
<213> ORGANISM: Eubacterium rectale

<400> SEQUENCE: 6

Met Asp Thr Ser Asn Leu Met Glu Gln Ile Leu Ser Ser Asp Asn Leu
1               5                   10                  15

Asn Arg Ala Tyr Leu Gln Val Val Arg Asn Lys Gly Ala Glu Gly Val
            20                  25                  30

Asp Gly Met Lys Tyr Thr Glu Leu Lys Glu His Leu Ala Lys Asn Gly
        35                  40                  45

Glu Thr Ile Lys Gly Gln Leu Arg Thr Arg Lys Tyr Lys Pro Gln Pro
    50                  55                  60

Ala Arg Arg Val Glu Ile Pro Lys Pro Asp Gly Gly Val Arg Asn Leu
65                  70                  75                  80

Gly Val Pro Thr Val Thr Asp Arg Phe Ile Gln Gln Ala Ile Ala Gln
                85                  90                  95

Val Leu Thr Pro Ile Tyr Glu Glu Gln Phe His Asp His Ser Tyr Gly
            100                 105                 110

Phe Arg Pro Asn Arg Cys Ala Gln Gln Ala Ile Leu Thr Ala Leu Asn
        115                 120                 125

Ile Met Asn Asp Gly Asn Asp Trp Ile Val Asp Ile Asp Leu Glu Lys
    130                 135                 140

Phe Phe Asp Thr Val Asn His Asp Lys Leu Met Thr Leu Ile Gly Arg
145                 150                 155                 160

Thr Ile Lys Asp Gly Asp Val Ile Ser Ile Val Arg Lys Tyr Leu Val
                165                 170                 175

Ser Gly Ile Met Ile Asp Asp Glu Tyr Glu Asp Ser Ile Val Gly Thr
            180                 185                 190

Pro Gln Gly Gly Asn Leu Ser Pro Leu Leu Ala Asn Ile Met Leu Asn
        195                 200                 205

Glu Leu Asp Lys Glu Met Glu Lys Arg Gly Leu Asn Phe Val Arg Tyr
    210                 215                 220

Ala Asp Asp Cys Ile Ile Met Val Gly Ser Glu Met Ser Ala Asn Arg
225                 230                 235                 240

Val Met Arg Asn Ile Ser Arg Phe Ile Glu Glu Lys Leu Gly Leu Lys
```

```
                245                 250                 255

Val Asn Met Thr Lys Ser Lys Val Asp Arg Pro Ser Gly Leu Lys Tyr
            260                 265                 270

Leu Gly Phe Gly Phe Tyr Phe Asp Pro Arg Ala His Gln Phe Lys Ala
        275                 280                 285

Lys Pro His Ala Lys Ser Val Ala Lys Phe Lys Lys Arg Met Lys Glu
    290                 295                 300

Leu Thr Cys Arg Ser Trp Gly Val Ser Asn Ser Tyr Lys Val Glu Lys
305                 310                 315                 320

Leu Asn Gln Leu Ile Arg Gly Trp Ile Asn Tyr Phe Lys Ile Gly Ser
                325                 330                 335

Met Lys Thr Leu Cys Lys Glu Leu Asp Ser Arg Ile Arg Tyr Arg Leu
            340                 345                 350

Arg Met Cys Ile Trp Lys Gln Trp Lys Thr Pro Gln Asn Gln Glu Lys
        355                 360                 365

Asn Leu Val Lys Leu Gly Ile Asp Arg Asn Thr Ala Arg Arg Val Ala
    370                 375                 380

Tyr Thr Gly Lys Arg Ile Ala Tyr Val Cys Asn Lys Gly Ala Val Asn
385                 390                 395                 400

Val Ala Ile Ser Asn Lys Arg Leu Ala Ser Phe Gly Leu Ile Ser Met
                405                 410                 415

Leu Asp Tyr Tyr Ile Glu Lys Cys Val Thr Cys
            420                 425


<210> SEQ ID NO 7
<211> LENGTH: 76
<212> TYPE: DNA
<213> ORGANISM: Artificial Sequence
<220> FEATURE:
<223> OTHER INFORMATION: /note="combined DNA/RNA molecule"
      /note="E.coli tRNA-Lys-UUU with intact 3'-CCA"

<400> SEQUENCE: 7

gggucguuag cucaguuggu agagcaguug acuuuuaauc aauuggucgc agguucgaau     60

ccugcacgac ccacca                                                     76


<210> SEQ ID NO 8
<211> LENGTH: 75
<212> TYPE: DNA
<213> ORGANISM: Artificial Sequence
<220> FEATURE:
<223> OTHER INFORMATION: /note="combined DNA/RNA molecule"
      /note="E.coli tRNA-Lys-UUU with intact 3'-CC"

<400> SEQUENCE: 8

gggucguuag cucaguuggu agagcaguug acuuuuaauc aauuggucgc agguucgaau     60

ccugcacgac ccacc                                                      75


<210> SEQ ID NO 9
<211> LENGTH: 34
<212> TYPE: DNA
<213> ORGANISM: Artificial Sequence
<220> FEATURE:
<223> OTHER INFORMATION: barcode 11

<400> SEQUENCE: 9

gatatcgtca agatcggaag agcacacgtc tgaa                                 34


<210> SEQ ID NO 10
```

<211> LENGTH: 34
<212> TYPE: DNA
<213> ORGANISM: Artificial Sequence
<220> FEATURE:
<223> OTHER INFORMATION: barcode 12

<400> SEQUENCE: 10
gatagctaca agatcggaag agcacacgtc tgaa 34

<210> SEQ ID NO 11
<211> LENGTH: 34
<212> TYPE: DNA
<213> ORGANISM: Artificial Sequence
<220> FEATURE:
<223> OTHER INFORMATION: barcode 13

<400> SEQUENCE: 11
gatgcataca agatcggaag agcacacgtc tgaa 34

<210> SEQ ID NO 12
<211> LENGTH: 34
<212> TYPE: DNA
<213> ORGANISM: Artificial Sequence
<220> FEATURE:
<223> OTHER INFORMATION: barcode 14

<400> SEQUENCE: 12
gattctagca agatcggaag agcacacgtc tgaa 34

<210> SEQ ID NO 13
<211> LENGTH: 50
<212> TYPE: DNA
<213> ORGANISM: Artificial Sequence
<220> FEATURE:
<223> OTHER INFORMATION: /note="combined DNA/RNA molecule"
/note="RNA oligonucleotide "

<400> SEQUENCE: 13
gagcacacgu cugaacucca cucuuucccu acacgacgcu cuuccgaucu 50

<210> SEQ ID NO 14
<211> LENGTH: 52
<212> TYPE: DNA
<213> ORGANISM: Artificial Sequence
<220> FEATURE:
<223> OTHER INFORMATION: DNA oligonucleotide
<220> FEATURE:
<221> NAME/KEY: variation
<222> LOCATION: 52
<223> OTHER INFORMATION: /replace="a,c,g,t"

<400> SEQUENCE: 14
ragatcggaa gagcgtcgtg tagggaaaga gtggagttca gacgtgtgct cn 52

<210> SEQ ID NO 15
<211> LENGTH: 57
<212> TYPE: DNA
<213> ORGANISM: Artificial Sequence
<220> FEATURE:
<223> OTHER INFORMATION: RT primer
<220> FEATURE:
<221> NAME/KEY: variation
<222> LOCATION: 2
<223> OTHER INFORMATION: /replace="a,c,g,t"

<400> SEQUENCE: 15
rnagatcgga agagcgtcgt gtagggaaag aggtgactgg agttcagacg tgtgctc 57

<210> SEQ ID NO 16
<211> LENGTH: 49
<212> TYPE: DNA
<213> ORGANISM: Artificial Sequence
<220> FEATURE:
<223> OTHER INFORMATION: forward primer

<400> SEQUENCE: 16
aatgatacgg cgaccaccga gatctacact ctttccctac acgacgctc 49

<210> SEQ ID NO 17
<211> LENGTH: 52
<212> TYPE: DNA
<213> ORGANISM: Artificial Sequence
<220> FEATURE:
<223> OTHER INFORMATION: reverse primer
<220> FEATURE:
<221> NAME/KEY: variation
<222> LOCATION: 25
<223> OTHER INFORMATION: /replace="a,c,g,t"
<220> FEATURE:
<221> NAME/KEY: variation
<222> LOCATION: 26
<223> OTHER INFORMATION: /replace="a,c,g,t"
<220> FEATURE:
<221> NAME/KEY: variation
<222> LOCATION: 27
<223> OTHER INFORMATION: /replace="a,c,g,t"
<220> FEATURE:
<221> NAME/KEY: variation
<222> LOCATION: 28
<223> OTHER INFORMATION: /replace="a,c,g,t"
<220> FEATURE:
<221> NAME/KEY: variation
<222> LOCATION: 29
<223> OTHER INFORMATION: /replace="a,c,g,t"
<220> FEATURE:
<221> NAME/KEY: variation
<222> LOCATION: 30
<223> OTHER INFORMATION: /replace="a,c,g,t"

<400> SEQUENCE: 17
caagcagaag acggcatacg agatnnnnnn gtgactggag ttcagacgtg tg 52

<210> SEQ ID NO 18
<211> LENGTH: 36
<212> TYPE: DNA
<213> ORGANISM: Artificial Sequence
<220> FEATURE:
<223> OTHER INFORMATION: 5'-end 32P-labeled probe

<400> SEQUENCE: 18
cggaacctct ggattagaag tccagcgcgc tcgtcc 36

<210> SEQ ID NO 19
<211> LENGTH: 32
<212> TYPE: DNA
<213> ORGANISM: Artificial Sequence
<220> FEATURE:
<223> OTHER INFORMATION: Gly-CCC-2

<400> SEQUENCE: 19
cgggtcgcaa gaatgggaat cttgcatgat ac 32

<210> SEQ ID NO 20
<211> LENGTH: 18
<212> TYPE: DNA
<213> ORGANISM: Artificial Sequence
<220> FEATURE:
<223> OTHER INFORMATION: tRNA-Leu-UAA

<400> SEQUENCE: 20
cgcggacaac cgtccaac 18

<210> SEQ ID NO 21
<211> LENGTH: 16
<212> TYPE: DNA
<213> ORGANISM: Artificial Sequence
<220> FEATURE:
<223> OTHER INFORMATION: tRNA-Pro-UGG

<400> SEQUENCE: 21
tgaacccagg gcctct 16

<210> SEQ ID NO 22
<211> LENGTH: 21
<212> TYPE: PRT
<213> ORGANISM: Artificial Sequence
<220> FEATURE:
<223> OTHER INFORMATION: tRNA isotype

<400> SEQUENCE: 22

```
Phe Lys Tyr Ile Leu Met Arg Asp Ala Ser Thr Glu Met Asn Gly Val
1               5                   10                  15

His Pro Trp Gln Cys
            20
```

<210> SEQ ID NO 23
<211> LENGTH: 20
<212> TYPE: PRT
<213> ORGANISM: Artificial Sequence
<220> FEATURE:
<223> OTHER INFORMATION: tRNA isotype

<400> SEQUENCE: 23

```
Ile Cys Phe Ala Tyr Arg Asp Glu Leu Lys Trp His Ser Pro Thr Met
1               5                   10                  15

Asn Val Gly Gln
            20
```

<210> SEQ ID NO 24
<211> LENGTH: 21
<212> TYPE: PRT
<213> ORGANISM: Artificial Sequence
<220> FEATURE:
<223> OTHER INFORMATION: tRNA isotype

<400> SEQUENCE: 24

```
Val Leu Tyr Met Phe Lys Arg Cys Ala Ser Trp Thr Asn Ile Glu Pro
1               5                   10                  15

Gln Asp Gly His Met
            20
```

<210> SEQ ID NO 25
<211> LENGTH: 20
<212> TYPE: PRT
<213> ORGANISM: Artificial Sequence
<220> FEATURE:
<223> OTHER INFORMATION: tRNA isotype -continued

```
<400> SEQUENCE: 25

Tyr Lys Phe Thr Asn Trp Asp Ile Cys Met Arg Pro Ala Val Gly Gln
1               5                   10                  15

Leu Ser Met Glu
            20
```

METHOD FOR cDNA LIBRARY CONSTRUCTION AND ANALYSIS FROM TRANSFER RNA

CROSS-REFERENCE TO RELATED APPLICATIONS

This application is a Section 371 National Stage Application of International Application PCT/EP2021/072902, filed on Aug. 18, 2021, entitled "METHOD FOR CDNA LIBRARY CONSTRUCTION AND ANALYSIS FROM TRANSFER RNA". The disclosure of the afore-listed patent filing is incorporated herein by reference in its entirety, including all text, tables and drawings.

SEQUENCE LISTING

This application contains a Sequence Listing that has been submitted electronically in ASCII format and is hereby incorporated by reference in its entirety. The ASCII copy, created on Jun. 12, 2025, is named "009848-0578682_Corrected_SL.txt" and is 31,542 bytes in size.

The present invention relates to a method for the generation of a cDNA library from transfer RNA (tRNA), comprising (a) optionally ligating at least one DNA adapter to the 3'-end of tRNA, wherein the 3'-end of the DNA adapter is preferably a chain terminator dideoxycytidine, preferably under one or more of the following conditions: (i) crowding reagent at 5% to 35%, preferably 15% to 30%, and most preferably about 25%, (ii) $MgCl_2$ concentration of 1 mM to 15 mM, preferably 3 to 12 mM and most preferably about 10 mM (iii) a temperature of 12 °C to 37 °C, preferably of about 25 °C (iv) a pH of 6.0 to 9.0, preferably 6.5 to 8.0 and most preferably about 7.0, (v) reducing agent concentration of 0.1 mM to 10 mM, preferably 0.5 to 5 mM and most preferably about 1 mM, and (vi) a reaction time of at least 30 min, preferably at least 1.5 h and most preferably at least 3 h; and (b) reverse transcription in a primer-dependent reaction, in case step (a) is present, or in a template-switching reaction, in case step (a) is absent of the tRNA into cDNA by a group II intron reverse transcriptase, under the following conditions: (i) KCl or NaCl at a concentration of 20 mM to 250 mM, preferably 50 to 100 mM and most preferably about 75 mM, (ii) $MgCl_2$ at a concentration of 0.5 mM to 15 mM, preferably 1 to 5 mM and most preferably about 3 mM, (iii) a temperature of 30 °C to 65 °C, preferably of about 42 °C, and (iv) a reaction time of at least 2 h, preferably at least 8 h and most preferably at least 15 h, and preferably (vi) a pH of 6.5 to 9.5, preferably 7.0 to 8.5 and most preferably about 8.0, and/or (vi) a reducing agent (DTT) at a concentration of 1 mM to 12.5 mM, preferably 3 to 8 mM and most preferably about 5 mM In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Transfer RNAs (tRNAs) are short, abundant molecules required for translating genetic information into protein sequences. The composition of cellular tRNA pools is critical for efficient mRNA decoding and proteome integrity. tRNA expression is dynamically regulated in different tissues and during development (Dittmar et al., 2006; Ishimura et al., 2014; Kutter et al., 2011; Schmitt et al., 2014), and defective tRNA biogenesis is linked to neurological disorders and cancer (Kirchner and Ignatova, 2015).

Nevertheless, the regulation of tRNA levels and its physiological significance remain under-appreciated because of a lack of accurate, high-resolution methods for tRNA quantitation. A major challenge is posed by the stable structure and pervasive Watson-Crick face modifications, which block reverse transcriptase (RT) (Motorin et al., 2007). Library generation workflows without a strategy for overcoming RT blocks yield mostly short reads due to premature RT stops at modified sites, as for instance in quantitative mature tRNA sequencing (QuantM-tRNAseq) (Pinkard et al., 2020). Hybridization-based approaches can circumvent the need for cDNA synthesis, but they can only distinguish tRNAs differing by at least eight nucleotides (Dittmar et al., 2006). This limitation is problematic given the extensive sequence similarity among tRNA transcripts, which can differ by a single nucleotide even if they read different codons (Chan and Lowe, 2016). Strategies to overcome structure- and modification-induced RT barriers have included tRNA fragmentation (Arimbasseri et al., 2015; Gogakos et al., 2017; Karaca et al., 2014), the use of a thermostable template-switching RT in thermostable group II intron RTsequencing (TGIRT-seq and DM-tRNAseq) (Katibah et al., 2014; Qin et al., 2016; Zheng et al., 2015), and enzymatic removal of some base methylations in AlkB-facilitated RNA methylation sequencing (ARM-seq) and DM-tRNAseq (Cozen et al., 2015; Zheng et al., 2015).

Although these methods have improved tRNA representation in sequencing libraries, several limitations remain. First, all of these methods relieve only a fraction of RT blocks, which can bias recovery toward tRNA subsets with few modified sites or those that are better substrates for demethylation in vitro. Second, removing modifications eliminates information about their presence and stoichiometry, which could be inferred from signatures of RT stops and misincorporations (Clark et al., 2016; Ebhardt et al., 2009; Hauenschild et al., 2015; Katibah et al., 2014; Li et al., 2017; Motorin et al., 2007; Qin et al., 2016; Ryvkin et al., 2013; Safra et al., 2017; Zheng et al., 2015). RNA modification profiling based solely on misincorporation signatures would be advantageous, as RT stops can also arise from RNA degradation or structure. Conditions that enable read-through of Watson-Crick face modified sites while abrogating stops, however, have not been described for any RT so far (Werner et al., 2020). A variant of the HIV-1 RT with improved readthrough of N1-methyladenosine ($m^1A$) was recently derived by protein evolution (Zhou et al., 2019), but whether this enzyme can also overcome any of the other types of RT-blocking tRNA modifications is unknown.

The computational analysis of tRNA sequencing data also presents significant challenges that are often overlooked. The number of predicted tRNA anticodon families in different genomes ranges from 33 in *M. hominis* to 57 in humans, with many tRNAs encoded by multiple gene copies. In eukaryotes, there is also considerable sequence variation among tRNAs with identical anticodons, which becomes more pronounced with increasing organismal complexity (Goodenbour and Pan, 2006). While the 41 tRNA anticodon families in budding yeast constitute 54 distinct tRNA transcripts, ~400 unique tRNA molecules can be potentially produced in human cells (Chan and Lowe, 2016). Some of these can have tissue-specific functions even in the presence of closely related isodecoders (tRNAs that share an anticodon but differ in sequence elsewhere; Ishimura et al., 2014).

The exceptional degree of tRNA sequence similarity can undermine alignment accuracy, particularly for short reads resulting from premature RT stops (Pinkard et al., 2020) or tRNA fragmentation (Arimbasseri et al., 2015; Gogakos et al., 2017). The problem is compounded by multiple mismatches between tRNA-derived reads and the genomic reference that arise from RT misincorporation during modification readthrough. Current alignment approaches allow mismatches at any position of a read (Arimbasseri et al., 2015; Gogakos et al., 2017; Hoffmann et al., 2018; Katibah et al., 2014; Pinkard et al., 2020; Qin et al., 2016; Zheng et al., 2015), which can decrease mapping accuracy for nearly identical tRNAs. The total number of mismatches is also limited in some approaches, which can eliminate reads from highly modified tRNAs. Computational tool choice can thus substantially affect measurements of tRNA abundance and modification.

The technical problem to be solved herein is therefore the provision of a novel workflow that overcomes the experimental and optionally also computational hurdles to quantitative tRNA profiling.

Hence, the present invention relates to a method for the generation of a cDNA library from tRNA, comprising (a) optionally ligating at least one DNA adapter to the 3'-end of tRNA, wherein the 3'-end of the DNA adapter is preferably a chain terminator dideoxycytidine, preferably under one or more of the following conditions: (i) crowding reagent (preferably PEG-4000 or PEG-8000) at 5% to 35%, preferably 15% to 30%, and most preferably about 25%, (ii) $MgCl_2$ concentration of 1 mM to 15 mM, preferably 3 to 12 mM and most preferably about 10 mM (iii) a temperature of 12 °C to 37 °C, preferably of about 25 °C (iv) a pH of 6.0 to 9.0, preferably 6.5 to 8.0 and most preferably about 7.0, (v) reducing agent (preferably DTT) concentration of 0.1 mM to 10 mM, preferably 0.5 to 5 mM and most preferably about 1 mM, and (vi) a reaction time of at least 30 min, preferably at least 1.5 h and most preferably at least 3 h; and (b) reverse transcription in a primer-dependent reaction, in case step (a) is present, or in a template-switching reaction, in case step (a) is absent, of the tRNA into cDNA by a group II intron reverse transcriptase, under the following conditions: (i) KCl or NaCl at a concentration of 20 mM to 250 mM, preferably 50 to 100 mM and most preferably about 75 mM, (ii) $MgCl_2$ at a concentration of 0.5 mM to 15 mM, preferably 1 to 5 mM and most preferably about 3 mM, (iii) a temperature of 30 °C to 65 °C, preferably of about 42 °C, and (iv) a reaction time of at least 2 h, preferably at least 8 h and most preferably at least 15 h, and preferably (v) a pH of 6.5 to 9.5, preferably 7.0 to 8.5 and most preferably about 8.0, and/or (vi) a reducing agent (preferably DTT) at a concentration of 1 mM to 12.5 mM, preferably 3 to 8 mM and most preferably about 5 mM.

The term "about" as used herein means with increasing preference ±20%, ±10% and ±5 of the respective value.

cDNA (complementary DNA) is DNA synthesized from a single-stranded RNA template in a reaction catalyzed by the enzyme reverse transcriptase (RT). In accordance with the present invention the template RNA is tRNA. A cDNA library is generally a collection of different reverse-transcribed RNA templates which constitute some portion of the transcriptome of the organism and are stored as a "library" of cDNA molecules for sequencing and quantitation purposes. In accordance with the present invention the cDNA library comprises the complementary DNA strands of tRNAs.

The term "tRNA" as used herein refers to single tRNA as well as and preferably to a plurality of tRNAs, such as with increasing preference at least 2, at least 5, at least 10, at least 50, at least 100, at least 250 and at least 500 different tRNAs. The term "tRNA" as used herein more preferably is "a pool of tRNAs" and most preferebaly the pool of tRNAs within a cell. Each cell type in multicellular organisms may also comprise a different pool of tRNA. The tRNA pool is composed of various tRNA isoacceptor families, each family carries a different anticodon sequence that decodes the relevant codon by Watson-Crick base pairing, or codons with non-perfect base pairing of the third nucleotide by the wobble interaction. tRNA isoacceptor families are further classified to isotypes if they carry the same amino acid.

A tRNA (transfer RNA) is a type of RNA molecule that helps to decode a messenger RNA (mRNA) sequence into a protein. tRNAs function at specific sites in the ribosome during translation, which is a process that synthesizes a protein from an mRNA molecule. Proteins are built from smaller units called amino acids, which are specified by three-nucleotide mRNA sequences called "codons". Each codon represents a particular amino acid, and each codon is recognized by one or more specific tRNAs. The tRNA molecule has a distinctive folded structure with three hairpin loops that form the shape of a three-leafed clover. One of these hairpin loops contains a sequence called the "anticodon", which can recognize and decode an mRNA codon. Each tRNA has its corresponding amino acid attached to its 3' end. When a tRNA recognizes and binds to its corresponding codon in the ribosome, the tRNA transfers the appropriate amino acid to the end of the growing amino acid chain. Then the tRNAs and ribosome continue to decode the mRNA molecule until the entire sequence is translated into a protein. Organisms vary in the number of tRNA genes in their genome. For example, the nematode worm *C. elegans* has 708 genes encoding a tRNA, *Saccharomyces cerevisiae* has 275 tRNA genes and humans have more than 600 nuclear genes encoding cytoplasmic tRNA molecules. A tRNA is typically 60 to 100 nucleotides in length in eukaryotes.

A wide variety of tRNA modifications are found in the tRNA anticodon, which are crucial for precise codon recognition and reading frame maintenance, thereby ensuring accurate and efficient protein synthesis. In addition, tRNA-body regions are also frequently modified and thus stabilized in the cell. Over the past two decades, 16 novel tRNA modifications were discovered in various organisms, and the chemical space of tRNA modification continues to expand. Recent studies have revealed that tRNA modifications can be dynamically altered in response to levels of cellular metabolites and environmental stresses. Importantly, it is now understood that deficiencies in tRNA modification can have pathological consequences, which are termed 'RNA modopathies'. Dysregulation of tRNA modification is involved in mitochondrial diseases, neurological disorders and cancer (Suzuki (2021), Nature Reviews Molecular Cell Biology, 22:375-392).

A reverse transcriptase (RT) is an enzyme that is capable of generating a complementary DNA (cDNA) from an RNA template in a process termed reverse transcription. A group II intron RT is an RT being encoded by mobile group II introns, bacterial retrotransposons that are evolutionary ancestors of introns and retroelements in eukaryotes. Unlike retroviral RTs, which evolved to help retroviruses evade host defenses by introducing and propagating mutational variations, group II intron RTs evolved to function in retrohoming, a retrotranposition mechanism that requires faithful synthesis of a full-length cDNA of a long, highly structured group II intron RNA. Their beneficial properties for RNA-seq include high fidelity, processivity, and strand displacement activity, along with a proficient template-switching activity that is minimally dependent upon base pairing and enables the seamless attachment of RNA-seq adapters to target RNAs without RNA tailing or ligation. Thermostable group II intron RTs (TGIRTs) from bacterial thermophiles combine these beneficial properties with the ability to function at high temperatures (60-65 °C), which help melt out stable RNA secondary structures that can impede reverse transcription. A recent crystal structure of a full-length TGIRT enzyme (Gsl-IIC RT, a form of which is sold commercially as TGIRT-III; InGex) in active conformation with bound substrates revealed that group II intron RTs are closely related to RNA-dependent RNA polymerases, as expected for an ancestral RT, and identified a series of novel structural features that may contribute to their high fidelity and processivity. These features include more constrained binding pockets than retroviral RTs for the templating RNA base, 3' end of the DNA primer, and the incoming dNTP, as well as a larger fingers region that enables more extensive contact with the template-primer substrate than is possible for retroviral RTs (Xu et al. (2019), Scientific Reports, 9:7953).

The DNA adapter is an oligonucleotide sequence that is to be ligated to the 3'-end of tRNA, preferably the tRNAs in the pool in step (a) of the method of the invention. The DNA adapter comprises a sequence that is complementary to a sequence within an RT primer to be used in step (b) of the claimed method in primer-dependent RT reaction. The complementary sequence serves as the start site for the reverse transcription.

The overall length of the oligonucleotide sequence of the DNA adapter is preferably within 45 and 25 nucleotides and most preferably about 35 nucleotides. The complementary sequence within the adapter can generally be found at the 3'-end of DNA adapter and preferably has length of between 10 and 20 nucleotides and most preferably about 15 nucleotides.

The preferred chain terminator dideoxycytidine (ddC) at the 3'-end of the DNA adapter is to prevent concatemer formation. The 5'-end of the DNA adapter is preferably phosphorylated which enables the pre-adenylation of the DNA adapter prior to ligation. Pre-adenylation can be effected by a RNA ligase, such as the Mth RNA ligase. The effect to the reducing agent, such as DTT will discussed in connection with reverse transcription herein below.

The inventors not only optimized the conditions for the reverse transcription reaction but also the conditions for the adapter ligation. For this reason the ligation is with increasing preference under one or more, two or more, three or more, four or more, five or more, and most preferably all six of the following conditions: (i) crowding reagent (preferably PEG-4000 or PEG-8000) at 5% to 35%, preferably 15% to 30%, and most preferably about 25%, (ii) $MgCl_2$ concentration of 1 mM to 15 mM, preferably 3 to 12 mM and most preferably about 10 mM (iii) a temperature of 12 °C to 37 °C, preferably of about 25 °C (iv) a pH of 6.0 to 9.0, preferably 6.5 to 8.0 and most preferably about 7.5, (v) reducing agent (preferably DTT) concentration of 0.1 mM to 10 mM, preferably 0.5 to 5 mM and most preferably about 1 mM, and (vi) a reaction time of at least 30 min, preferably at least 1.5 h and most preferably at least 3 h. Under these conditions the ligation works particularly well and highly reliable. The one or more, two or more, three or more conditions preferably comprise one, two or all three of the conditions i), iii) and vi) because in particular these conditions were found to result in superior ligation efficiency.

The ligase to be use in step (a) is not particularly limited and can be any suitable RNA ligase. Preferred is T4 RNA ligase, in particular T4 RNA ligase 2 since it is used in the appended examples. T4 RNA Ligase 2 is also known as T4 Rnl2 (gp24.1) and has both intermolecular and intramolecular RNA strand joining activity. The enzyme can ligate the 3' OH of RNA to the 5' phosphate of DNA.

The most widely used and therefore preferred crowding agent is polyethylene glycol (PEG). PEG is preferably PEG-4000 or PEG-8000. Macromolecular crowding refers to the effects of adding macromolecules to a solution, as compared to a solution containing no macromolecules. Macromolecular crowding alters the binding properties and rate constants of a number of enzyme ligases. Hence, a crowding agent is an agent that is capable of altering the binding properties and rate constants of a number of enzyme ligases.

As discussed above, in case the method of the invention comprises step (a) the tRNA, preferably the tRNAs in the pool carry at their 3'-end a DNA adapter that harbors a sequence being complementary to the primer that is used in a primer-dependent RT. The method of the invention preferably comprises step (a) and there also preferably is carried out as a primer-dependent RT. The RT generally comprises the complementary sequence at its 3'-end and preferably has length of 12 to 25 nucleotides (nt), more preferably about 15 nt. The RT primer preferably comprises an 18-atom hexaethyleneglycol spacer that is thought to block elongation by DNA polymerases, which helps prevent rolling circle amplification during the subsequent PCR step for library construction. The sequences 5' and 3' to the 18-atom hexaethyleneglycol spacer spacer provide primer-binding sites for library construction PCR after cDNA circularization.

However, it also possible to omit the DNA adapter ligation of step (a) in which case the RT in step (b) is a template-switch reaction. This method uses the ability of group II intron RTs to template-switch directly from an artificial DNA/RNA hybrid primer substrate containing an RNA-seq adapter sequence to the 3' end of an RNA template, thereby coupling RNA-seq adapter addition to the initiation of cDNA synthesis. Hence, the template-switch reaction uses RNA/DNA duplex with a single-nucleotide-overhang that is produced by annealing an RNA oligonucleotide to a DNA oligonucleotide. The RNA oligonucleotide and the DNA oligonucleotide both preferably have a length of between 40 and 60 nucleotides and most preferably of about 50 nucleotides, provided that the single-nucleotide-overhang is produced. The single-nucleotide-overhang can be found in the DNA oligonucleotide.

The method according the first aspect of the invention is a sensitive method for cDNA library construction from endogenously modified tRNAs. By identifying conditions that enable efficient RT readthrough of modified sites, the inventors advantageously achieved a uniform sequence coverage of tRNA, in particular tRNA pools from yeast, fly, and human cells while retaining modification signatures. The method is sensitive, robust, and applicable to any organism with a known genome, and, thus, will help to shed new light on previously intractable aspects of tRNA biology. The method according the first aspect of the invention is published in Behrens et al. (2021), Molecular Cell, 81:1-14 and the technical superiority of the method according the first aspect of the invention is appraised in the review article Winer and Schwartz. Molecular Cell, 81:1595-1597.

Via careful calibration of reverse transcription reaction, the inventors succeeded in achieving a complete read-through of the entire tRNA sequence in nearly all molecules.

This was critical to avoid bias in the quantification caused by RT-blocking modifications. Indeed, the examples herein below show that tRNAs with multiple RT-stop-causing modifications were under-represented in the previous protocols as compared to the method of the present invention.

The careful calibration of reverse transcription reaction resulted in the following conditions: (i) KCl or NaCl at a concentration of 20 mM to 250 mM, preferably 50 to 100 mM and most preferably about 75 mM, (ii) $MgCl_2$ at a concentration of 0.5 mM to 15 mM, preferably 1 to 5 mM and most preferably about 3 mM, (iii) a temperature of 30 °C to 65 °C, preferably of about 42 °C, and (iv) a reaction time of at least 2 h, preferably at least 8 h and most preferably at least 15 h, and preferably (v) a pH of 6.5 to 9.5, preferably 7.0 to 8.5 and most preferably about 8.0, and/or (vi) a reducing agent (preferably DTT) at a concentration of 1 mM to 12.5 mM, preferably 3 to 8 mM and most preferably about 5 mM. Among KCl and NaCl KCl is preferred as it is used in the appended examples.

Regarding the conditions according to items (i) to (iii) is of note that the salt concentrations and the temperature are lower than use in prior art methods for the generation of a cDNA library from tRNA, in particular a pool of tRNAs. The inventors found that at lower salt and temperature conditions the cDNA yield was dramatically improved (see also FIG. 1A). In addition, it was found that in the case of extending the reaction time as compared to the prior art and to the time as specified by item (iv) nearly all premature RT stops can be prevented without compromising template integrity (see FIG. 1B). Hence the conditions according to items (i) to (iv) are the key to achieving a complete read-through of the entire tRNA sequence in nearly all molecules.

Items (v) further sets the ideal pH conditions. According item (vi) a reducing agent, preferably dithiothreitol (DTT) is used in the RT. While a reducing agent is not essential for the RT it helps to break bonds (like disulfide bonds) which might loosen the secondary structure of the tRNA and might facilitate RT enzyme initiation of transcription and processivity.

In accordance with a preferred embodiment, the method of the invention further comprises prior to step (a), (a') the purification of tRNAs from an RNA preparation.

Means and methods for the isolation of tRNAs from RNA preparations are known in the art (see, for example, Cayama et al (2000), Nucleic Acids Res.; 28 (12): e64). As discussed, tRNA is typically 60 to 100 nucleotides in length in eukaryotes. Hence, one example to isolate tRNA is gel size selection and in particular the gel size selection as used in the appended examples.

In accordance with a more preferred embodiment, the method of the invention further comprises prior to step (a'), (a'') the isolation of an RNA preparation from eukaryotic cells.

Also means and methods for the isolation of RNA from cells or other biological material such a tissue of body fluids are known in the art. The most commonly used method is guanidinium thiocyanate-phenol-chloroform extraction. The filter-paper based lysis and elution method features high throughput capacity.

In accordance with a further preferred embodiment, the method of the invention further comprises the construction of a sequencing library by PCR amplification of the cDNA as obtained in step (b), wherein the cDNA is optionally circularized prior to the amplification.

Means and methods for the PCR amplification of the cDNA are well established and, for example, reviewed in Yin (2004), Molecular Biotechnology, 27:245-252. Methods for cDNA amplification comprising cDNA circularization are described in Polidoros et a. (2015), BIOTECHNIQUES, 41 (1) and the appended examples.

The cDNA library is single-stranded and typically not in sufficient quantity to be directly subjected to high-throughput sequencing. It is therefore amplified after being converted into double-stranded DNA by means of PCR. Hence, a "sequencing library" is a library constructed by means of PCR from the cDNA library according to the invention. This requires either circularization of the cDNA (as illustrated in the appended examples) or ligation of another adapter to the 3' of the cDNA. This is necessary since PCR amplification requires both 5' and 3' primer binding sites. An additional purpose of the PCR is that it adds sequences to the 5' and 3' ends of the library that are required for high-throughput sequencing.

In accordance with another preferred embodiment, at least one DNA adapter comprises at least two, three or four DNA adapters that are distinguished from each other by a barcode sequence.

In other words, the method of the invention further comprises in accordance with this preferred embodiment one, two, three, or four DNA adapters that are distinguished from each other by unique barcode sequences.

A barcode is a short section of DNA with the primer that allow to distinguish one primer from all other primers in a mixture of primers. The barcode does not from part of the complementary sequence of the DNA adapter but can generally be found 5' of the complementary sequence of the DNA adapter.

In the appended examples four barcoded DNA adapters are used. The use of two or more barcoded DNA allows to separate the tRNA from each other and thereby to reduce the cost of the RT reaction and to allow similar treatment of up to four cellular tRNA pools present in the same reaction tube under the same reaction conditions.

In accordance with a different preferred embodiment, the method of the invention further comprises (d) sequencing the sequencing library as obtained in step (c).

The full-length cDNAs and accordingly also the sequencing library generated therefrom contain the complete sequence information of their respective tRNA templates. This information can be determined by full-length sequencing of the sequencing library and provides knowledge of the sequence and abundance of the tRNA. Means and methods for the sequencing of the sequencing library are known in the art.

In accordance with a more preferred embodiment, the method of the invention further comprises (e) aligning the sequencing reads as obtained in step (d) to known tRNA reference sequences.

By the alignment of the sequencing reads as obtained from the cDNA to known tRNA reference sequences it is generally possible to identify which tRNAs were present and the abundance of the original tRNA, preferably pool of tRNAs that was used in order to obtain the cDNA library by the method of the invention.

The alignment is generally made by a computer and, thus, step (e) is generally a computer-implemented method.

A number of tRNA libraries are available and non-limiting examples are GtRNAdb, GtRNAdb 2.0, mitotRNAdb (all University of California Santa Cruz), tRNAdb 2009 (all university of Leipzig) or T-psi-C (institute of human genetics, Polish Academy of Sciences).

Preferably the tRNA reference sequences from the databases GtRNAdb (genomic tRNAs) and mitotRNAdp (mitochondrial tRNA) are used, noting that these two databases were used in the examples. Alignment with the tRNA reference sequences is preferably performed with the algorithm Bowtie (v1.2.2), Bowtie 2 (preferred version v2.3.3.1), or GSNAP whereby GSNAP is most preferred.

Further details on the preferred mode of step (e) can be taken from the section "tRNA read alignment with Bowtie and Bowtie 2" in the appended examples.

Step (e) and the further computational framework according the preferred embodiments that will be described wherein below (e.g., for data analysis, and visualization) provide a user-friendly computational toolkit, which allows measurements of tRNA abundance, charging fractions, and modification profiles with unprecedented accuracy and resolution, the method of the invention and this computational toolkit allow the identification of a wide variation in tRNA isodecoder abundance among different human cell lines and an interdependence among tRNA modifications at distinct sites.

Figure 2A:
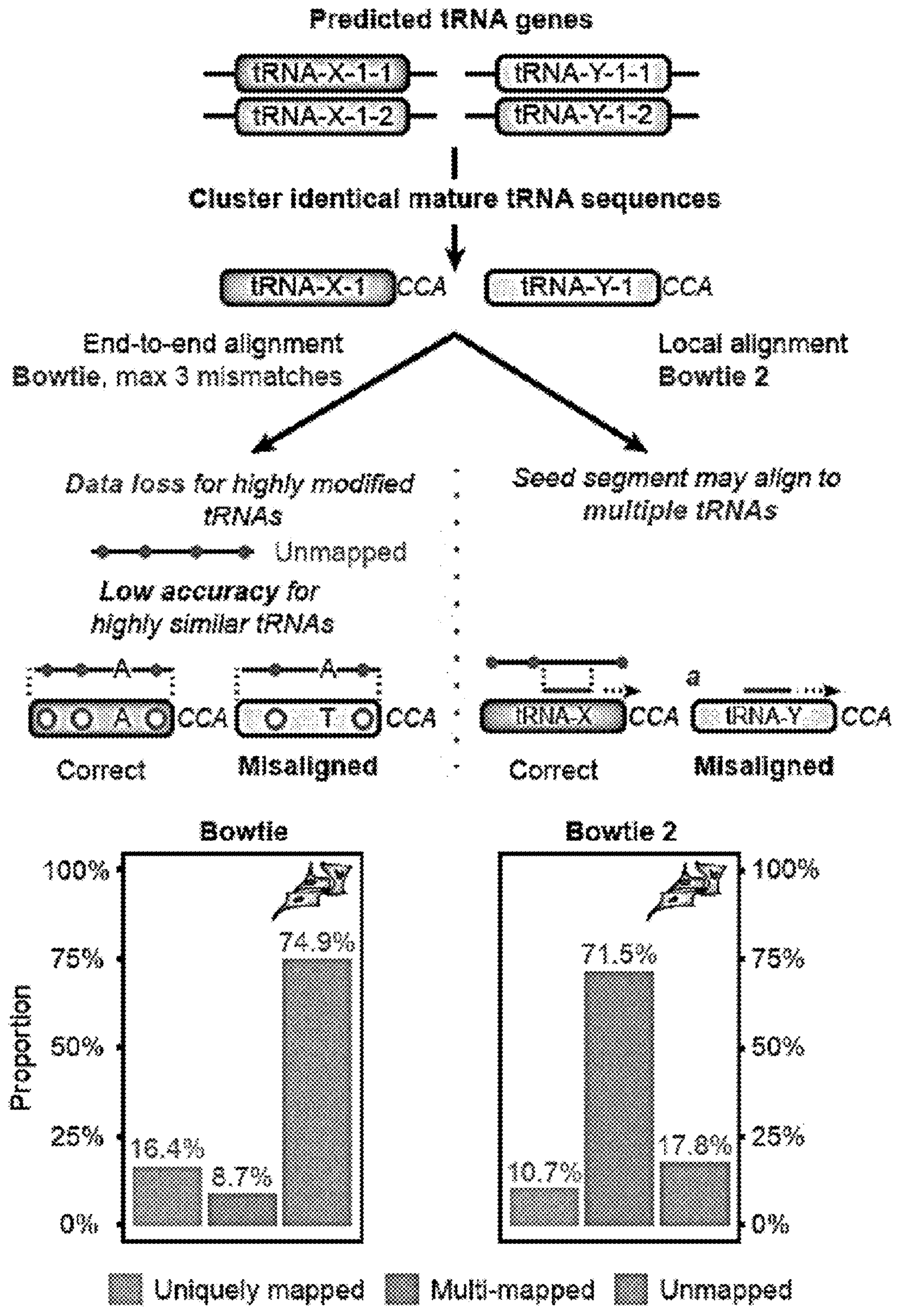
Figure 2B:
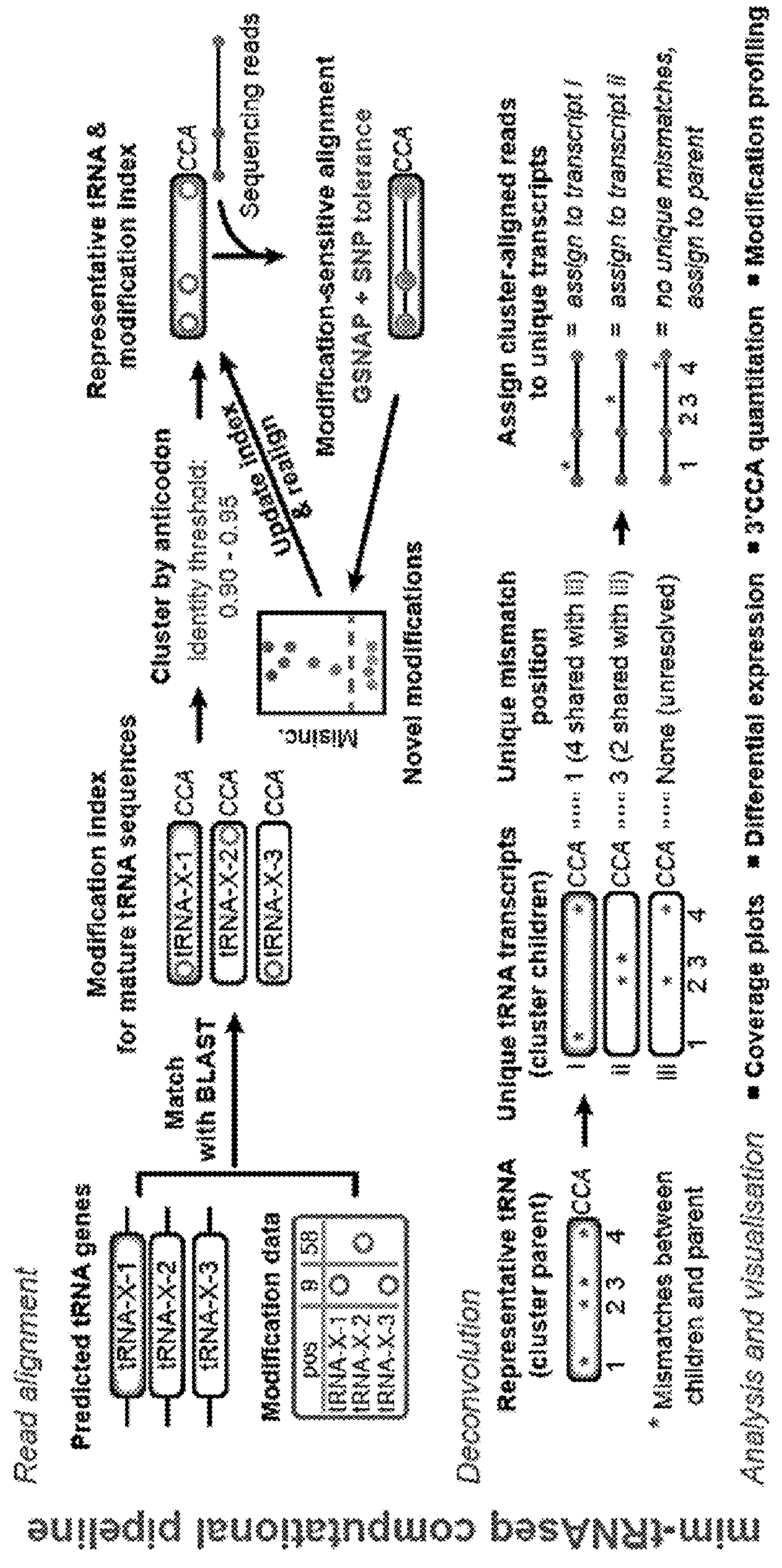

The entire toolkit is accessible https://github.com/nedialkova-lab/mim-tRNAseq and illustrated in FIGS. 2A and 2B. The toolkit is an automated analysis pipeline for the quantitation and analysis of tRNA expression and modifications:

Cluster tRNAs, index modifications, and perform SNP-tolerant read alignment with GSNAP.

Deconvolve cluster aligned reads back into unique tRNA transcript-level reads

Calculate coverage information and plots (useful for QC)· Quantify expression

Calculate tRNA differential expression with DESeq2.

Analyze functional tRNA pools and tRNA completeness via 3'-CCA analysis

Comprehensive modification quantification and misincorporation signature analysis In accordance with a further more preferred embodiment, the method of the invention further comprises (f) aligning the sequencing reads as obtained in step (d) to a reference of known tRNA transcript sequences, wherein the reference comprises information on the identity and location of known modified ribonucleosides in tRNAs.

As discussed herein above, a wide variety of tRNA modifications are found in tRNAs. These modifications may result in mismatches between the tRNA and the cDNA as obtained after RT. In order to be able to correct the alignment for such mismatched the reference preferably comprises information on the identity and location of known modified ribonucleosides in tRNAs.

Also, this alignment is generally made by a computer and, thus, also step (f) is generally a computer-implemented method.

Likewise, a number of tRNA libraries with information on modified ribonucleosides in tRNAs are available and non-limiting examples are Modomics (Boccaletto (2018), Nucleic Acids Res; 46 (D1): D303-D307), T-psi-C (institute of human genetics, Polish Academy of Sciences) and "The RNA Modification Database" (KU Leuven). A review of tRNA modification databases is available from Ma et al. (2021), Methods, https://doi.org/10.1016/j.ymeth.2021.03.003).

Herein, preferably Modomics is used, noting that this database is also used in the appended examples. Modomics provides comprehensive annotations of tRNA and the data therein can be used to enable position-specific mismatch tolerance during alignment. It is in particular preferred to use Modomics in combination with GSNAP to detect mismatches caused by modifications in sequencing reads.

Further details on the preferred mode of the performance of step (f) can be taken from the section "modification indexing and clustering" of the appended examples.

In accordance with an even more preferred embodiment, the reads are aligned using a short read alignment algorithm, preferably by using the Genomic Short-read Nucleotide Alignment Program to the reference generated in (f), wherein the reference is preferably clustered into clusters of tRNA genes sharing an anticodon.

The alignment of sequencing reads as obtained from a tRNA based cDNA library is generally difficult for two reasons. As discussed, tRNA modifications may result in mismatches between the tRNA and the cDNA as obtained after RT. In addition, tRNAs share a high sequence identity to each other which makes it difficult to distinguish them from each other with high certainty.

Short read alignment aims to align short reads to reference genomes, which is essential to almost all applications related to next-generation sequencing technologies, such as methylation patterns profiling (MeDIP-Seq), protein-DNA interactions mapping (ChIP-Seq), and differentially expressed genome identification (RNA-Seq). All these applications require aligning large quantities of short reads to reference.

A number of short read alignment algorithms are available from the prior art that are particularly useful for RNA. Non-limiting examples are provided in Hoffman et al. (2018), Bioinformatics, 34 (7): 1116-1124 and Tsuchiya (2016), Bioinformatics, 32 (12): i369-i377.

The short read alignment algorithm is preferably Genomic Short-read Nucleotide Alignment Program (GSNAP, preferred version v2019-02-26) that is also employed in the appended examples (Wu et al. (2010), Bioinformatics, 26 (7): 873-81 and Wu et al. (2016), Methods Mol Biol.; 1418:283-334). GSNAP is a tool to align single- and paired-end reads to a reference genome. The GSNAP algorithm is based on the seed-and-extend method and works on reads down to 14 nucleotides of length, and computes SNP-tolerant alignments of various combinations of major and minor alleles. The algorithm can discover long-distance and interchromosomal splicing events by utilizing known splice sites data or by probabilistic models. In addition, the GSNAP algorithm can construct alignments using reads originating from bisulfite-treated DNA samples.

The additional step of clustering the reference into clusters of tRNA genes sharing an anticodon offers the technical advantage to first assign the reads to a particular cluster of tRNAs that share sequence similarity followed by deconvolution into individual tRNAs. In both the alignment and the deconvolution steps, only nucleotide positions lacking chemical modifications are taken into consideration to avoid erroneous assignments due to RT-mediated misincorporations. This read-assignment strategy significantly increases the number of reads that can be uniquely assigned to an individual tRNAs.

In accordance with a more preferred embodiment, the reads are optionally aligned to RNA reference sequences in single nucleotide polymorphism (SNP)-tolerant mode, using known modified ribonucleotides as potential sites of mismatch to the reference sequence.

The above-described clustering and SNP tolerance mode both prevent data loss for defined tRNA subsets. The details of the preferred SNP-tolerant mode to be employed can be taken from the section "Read alignment and modification discovery" in the appended examples.

In brief, in a SNP tolerance mode modified sites of tRNA are treated as pseudo-SNPs to allow modification-induced mismatches at these sites in a sequence- and position-specific manner. The non-templated nucleotide extensions are not counted as mismatches during alignment. If a mismatch is specified, then misincorporation analysis is performed and new, unannotated modifications are called. The existing SNP index is then updated with these new sites, and realignment of all reads is performed with a mismatch tolerance set. This procedure is useful for detecting unknown modifications in poorly annotated tRNAs and allows more accurate and efficient read alignment, which improves the results of all downstream analyses.

In accordance with a further more preferred embodiment, the method of the invention further comprises (g) subjecting the reads aligned to clusters to a deconvolution algorithm that assigns the aligned reads to unique tRNA species.

The algorithm that assigns cluster aligned reads to unique tRNA species is capable of restoring single-transcript resolution for subsequent analyses. In the algorithm each cluster is assessed for single nucleotide differences that distinguish unique tRNA sequences, on the basis of which each read is separated from the cluster "parent" and assigned to an individual transcript.

Further details on the preferred mode of a deconvolution algorithm that assigns the aligned reads to unique tRNA species can be taken from the section "read deconvolution" in the appended examples. Further details on the preferred mode of evaluating the results of the deconvolution algorithm can be taken from the section "Modification, RT stop, readthrough and 3'-CCA end analyses" in the appended examples.

Also step (g) is generally a computer-implemented method.

In accordance with a yet further more preferred embodiment, the method of the invention further comprises after read deconvolution (h) the analysis of one or more of read coverage, 3'-CCA, differential tRNA abundance and modification profiling.

Read coverage describes how often, in average, a reference sequence is covered by bases from the reads. This is an important information because multiple observations per base are needed to obtain to a reliable call. Therefore, read coverage is also used as a unit for the statistical power of sequencing data. Depending on the reference, there are different ways to calculate this coverage which are shown below.

3'-CCA is a cytosine-cytosine-adenine sequence at the 3' end of all tRNA molecules required for the attachment of the amino acid at this end of the tRNA.

Differential tRNA abundance defines the relative abundance of different tRNAs, in particular in the tRNA pool. Cells use the tRNA abundance to affect protein expression.

Modification profiling designates the profiling of the nucleotide modifications of tRNA, preferably the tRNA pool.

Further details on the preferred mode of step (h) can be taken from the section "Post-alignment analyses" in the appended examples.

In brief, normalized coverage can be scaled to account for potential differences in 3'-CCA intactness. Read counts per unique tRNA sequence can be summed up to calculate read counts per isoacceptor family (all tRNAs sharing an anticodon). These counts can be subsequently used by a DESeq2 pipeline for count transformations, sample distance analysis using distance matrix heatmaps, PCA plots, and differential expression analysis at the level of isoacceptor families and unique tRNA transcripts (only for completely resolved clusters). In the case that only one experimental condition is supplied, or if there are no replicates for one or more conditions, differential expression analysis is not performed on these samples, but a normalized counts table is still produced for investigations into tRNA abundance.

The method of the invention may also further comprise "Post-alignment analyses" as detailed in the examples. For instance, filtered out unique tRNA sequences may be excluded from all downstream analyses, except differential expression analysis by DESeq2 (preferred version v1.26.0, Love et al (2014), Genome Biol. 15, 550) where all unique tRNA sequences are included.

Step (h) is likewise generally a computer-implemented method.

In accordance with a further preferred embodiment, the group II intron reverse transcriptase is a thermostable group II intron reverse transcriptase.

A thermostable group II intron reverse transcriptase (TGIRTs) function at high temperatures (usually 60-65 °C), which help melt out stable RNA secondary structures that can impede reverse transcription. For this reason, TGIRT is the preferred example of RTs.

The TGIRT RT is preferably TGIRT™-III Enzyme (InGex catalogue No. TGIRT50). This enzyme displays higher thermostability, processivity, and fidelity than retroviral reverse transcriptases, allowing full-length, end-to-end cDNA synthesis from highly structured or heavily modified RNAs (e.g., tRNAs), and RNAs containing GC-rich repeat expansions.

In accordance with a more preferred embodiment, the TGIRT has the sequence of any one of SEQ ID NOs: 1 to 5 or a sequence being at least 80% identical thereto.

In accordance with a more preferred embodiment, the MarathonRT has the sequence of SEQ ID NO: 6 or a sequence being at least 80% identical thereto.

The sequence identities of at least 80% is with increasing preference at least 85%, at least 90%, at least 95%, at least 96%, at least 97%, at least 98% and at least 99% sequence identity.

The sequence identities herein are preferably determined with the BLAST algorithm, in particular protein BLAST (blastp).

The MarathonRT has been purified from *Eubacterium* rectale is an ultraprocessive reverse transcriptase used to catalyze the formation of DNA from RNA (kerafast, catalogue No. EYU007).

Unless otherwise defined, all technical and scientific terms used herein have the same meaning as commonly understood by one of ordinary skill in the art to which this invention belongs. In case of conflict, the patent specification including definitions, will prevail.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

This also holds true for alternatives in different claims that depend from each other. Thus, if claim 1 recites three alternatives of the same category and claim 2 recites three alternatives of a different category as recited in claim 1, and refers back to claim 1, all combinations of the alternatives as recited in claims 1 and 2 are explicitly disclosed herein.

The above considerations apply mutatis mutandis to all appended claims

The figures show.

FIG. 1. An optimized workflow for full-length cDNA library construction from eukaryotic tRNA pools FIG. 1(A)-Schematic of template-switching TGIRT reactions primed by an RNA/DNA duplex with a single-nucleotide 3' overhang and a gel image of cDNA products from endogenously modified IRNA pools from *S. cerevisiae* (Sc). K562 cells (Hs), or a synthetic unmodified IRNA (Syn) at different reaction temperatures and salt concentration. Red, reaction conditions previously used for ERNA library construction; asterisks, premature stops to cDNA synthesis; hash, potential products from end-to-end linkage of tRNAs.

FIG. 1(B)-Schematic of the mim-tRNAseq library generation workflow. Top gel image: 3' adapter ligation reactions with four barcoded adapters. Ligation efficiency was measured by normalizing input tRNA band intensity to that in reactions from which Rnl2trKQ was omitted. Bottom gel image: comparison of cDNA yield in short (1 h) or extended (16 h) primer-dependent TGIRT RT on a mix of adapter-ligated IRNA pools from *S. cerevisiae* and human K562 and HEK293T cells.

FIG. 2. The mim-tRNAseq computational pipeline: a comprehensive framework for tRNA sequencing data analysis FIG. 2(A)-Bowtie and Bowtie 2 alignment strategies and mapping statistics for a tRNA library from HEK293T cells constructed with the mim-tRNAseq workflow (n=1).

FIG. 2(B)-Outline of the mim-tRNAseq computational pipeline.

Figure 2C:
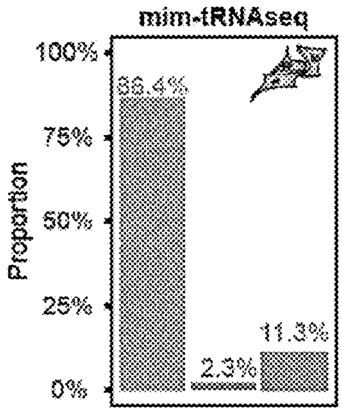

FIG. 2(C)-Alignment statistics of HEK293T data (as in A; n=1) using the mim-tRNAseq pipeline.

Figure 2D:
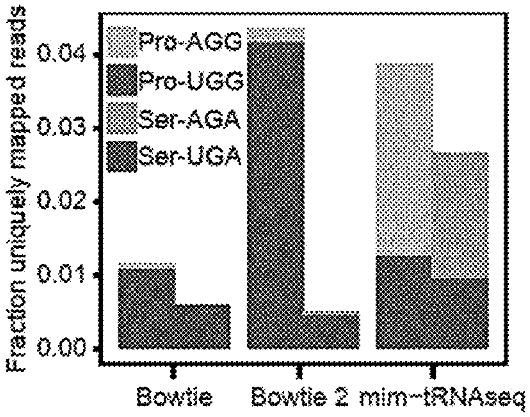

FIG. 2(D)-Uniquely aligned read proportions for inosine 34 (134)- and uridine 34 (U34)-containing Ser and Pro tRNA isoacceptors using the three alignment strategies on a HEK293T dataset generated as in FIG. 1B.

(E) Distribution of uniquely aligned reads among tRNA isotypes in published datasets and mim-tRNAseq from HEK293-derived cell lines (hydro-tRNAseq and QuantM-tRNAseq: HEK293 T-Rex Flp-IN; DM-tRNAseq control or AlkB-treated [+AlkB] and mim-tRNAseq library construction: HEK293T). Proportions were obtained from published counts per tRNA ("publ") or after re-analysis of the datasets with the mim-tRNAseq pipeline ("new"). tRNA families that carry the same amino acid (isotypes) are sorted by the number of RT barriers annotated in MODOMICS (decreasing from top to bottom; grayscale, isotypes without MODOMICS annotation).

Figure 3A:
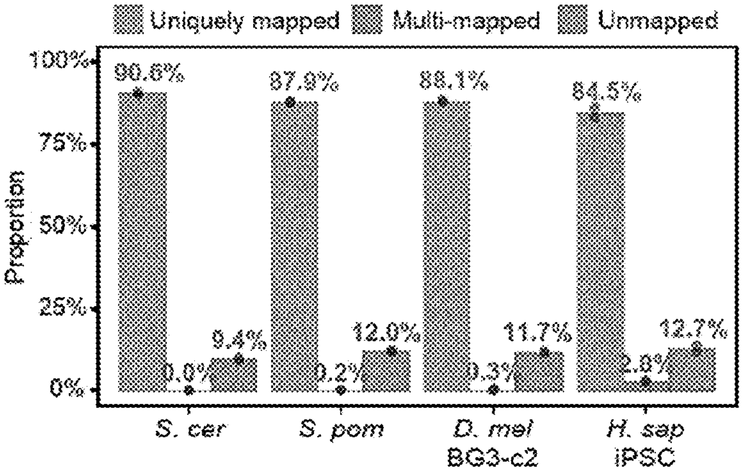

FIG. 3. mim-tRNAseq improves quantitative analysis of tRNA pools in cells from diverse eukaryotes FIG. 3(A)-Alignment statistics for mim-tRNAseq datasets from the indicated cell types. Bars and labels indicate average values, dots show individual sample values (n=2).

Figure 3B:
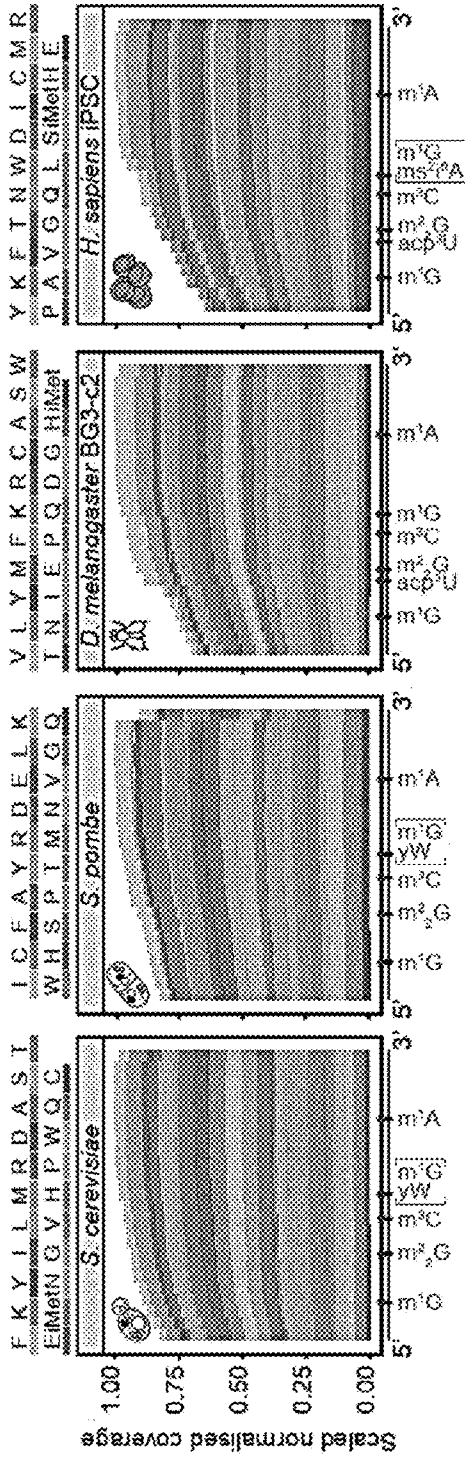

FIG. 3(B)-Metagene analysis of scaled sequence coverage across nuclear-encoded tRNA isotypes ordered per sample by differences between 3' and 5' coverage (decreasing order from top to bottom; n=1). y axis values normalized to the second-to-last bin from the 3' end. Each x axis bin represents 4% of tRNA length. Indicated are major known barriers to RT.

Figure 3C:
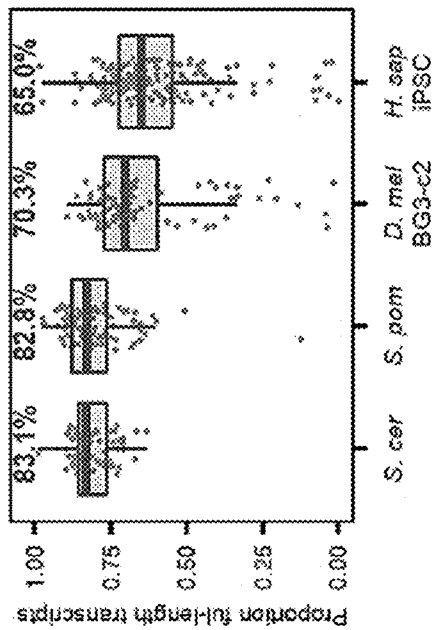

FIG. 3(C)-Boxplots of full-length fraction per IRNA transcript in datasets from (B) (center line and label: median; box limits: upper and lower quartiles; whiskers: 1.5× interquartile range).

Figure 3D:
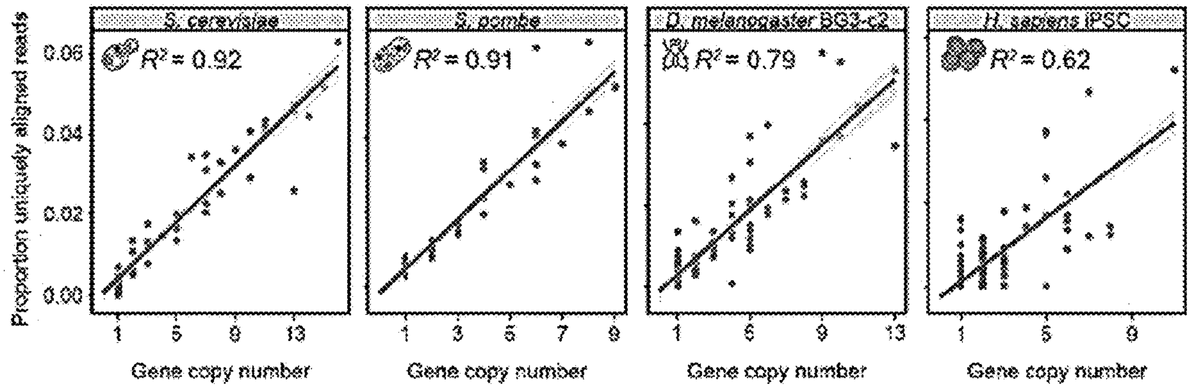

FIG. 3(D)-Correlation plots of unique tRNA gene copy number and corresponding proportion of uniquely aligned tRNA reads in single replicates (same samples as in B) from *S. cerevisiae, S. pombe*, and *D. melanogaster* BG3-c2 cells and hiPSCs. Solid blue lines: linear regression model; shaded gray: 95% confidence interval (CI).

Figure 4A:
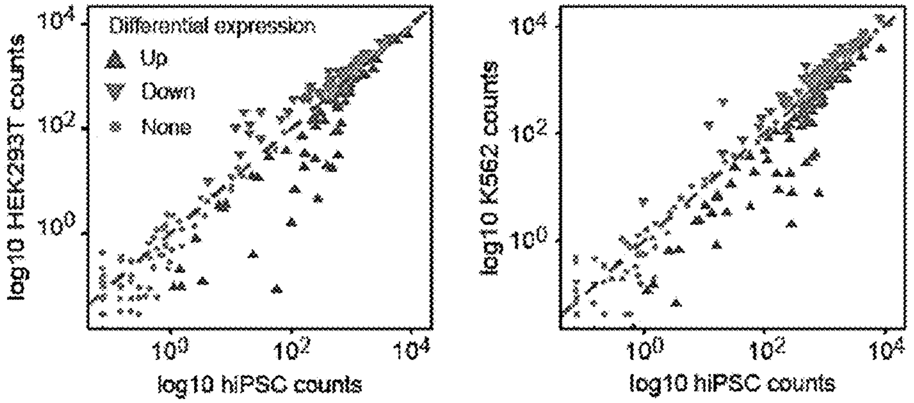

FIG. 4. mim-tRNAseq accurately captures differential tRNA expression and aminoacylation with single-transcript resolution FIG. 4(A)-Differential expression analysis of unique tRNA transcripts in HEK293T and K562 relative to hiPSCs. Axes represent log-transformed normalized read counts from DESeq2, with significant down- and upregulation in hiPSCs indicated with closed orange and green triangles, respectively (false discovery rate [FDR]-adjusted one-sided Wald test $p \leq 0.01$, n=2).

Figure 4B:
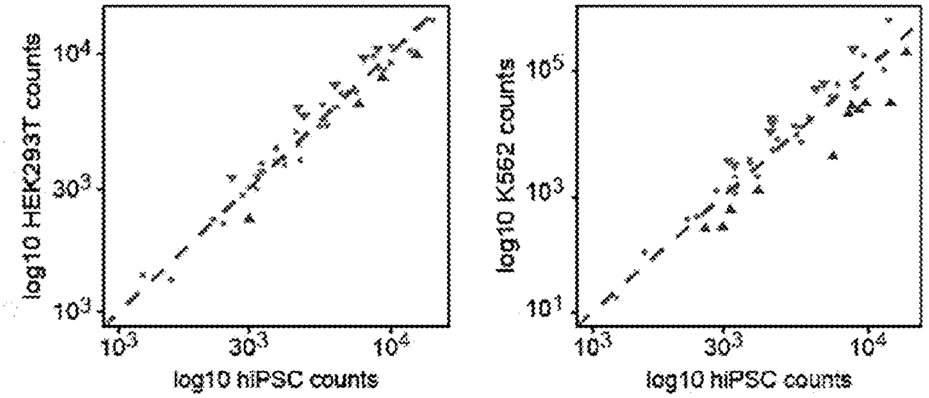

FIG. 4(B)-Differential expression analysis as in (A) for counts per tRNA anticodon family.

Figure 4C:
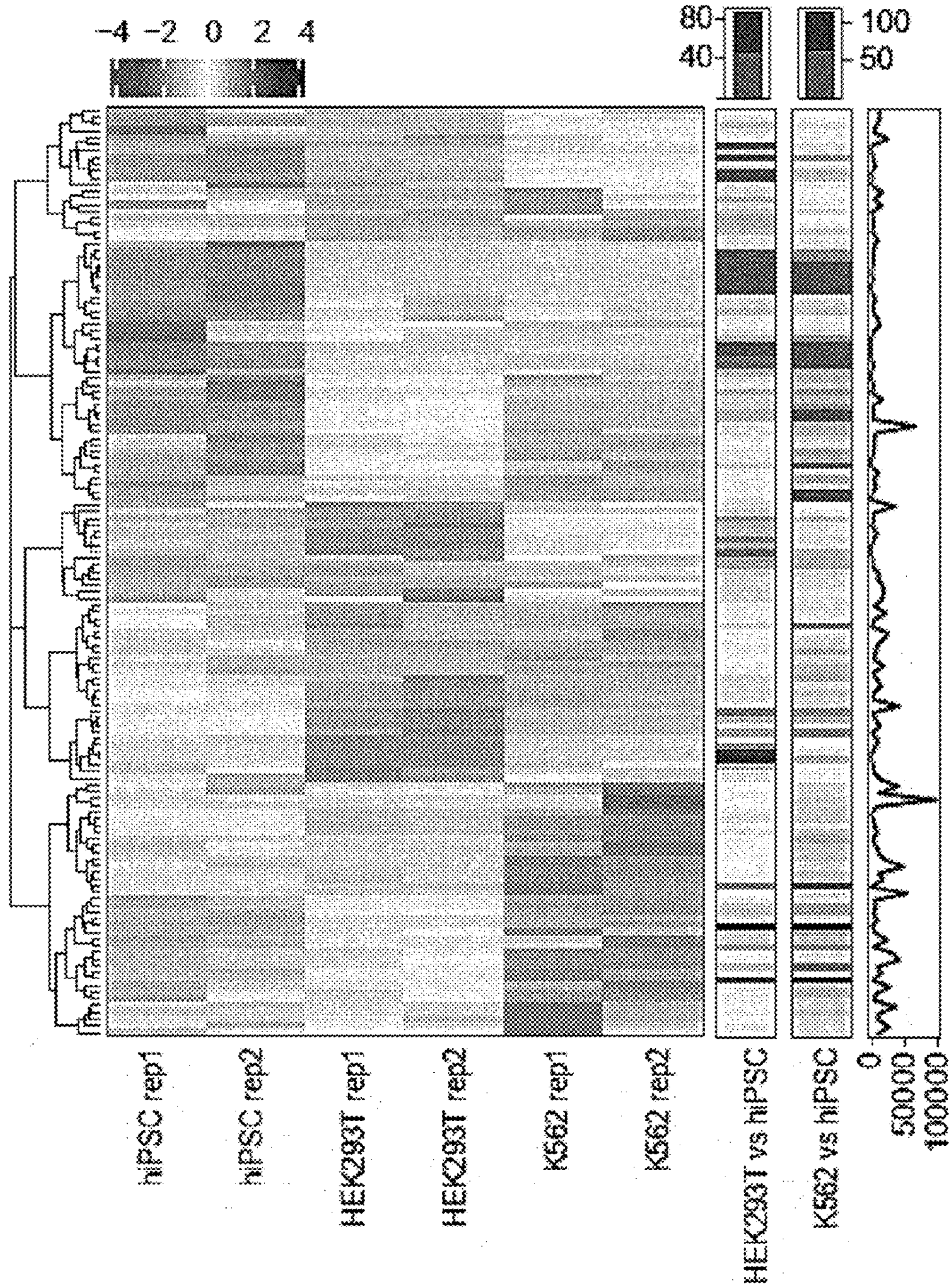

FIG. 4(C)-Left panel: hierarchically clustered expression heatmap showing scaled z score of normalized unique transcript counts in HEK293T, K562, and hiPSCs (n=2). Middle panels: differential expression for HEK293T and K562 relative to IPSCs (values, $\log_2$ fold changes; bar plots, numbers of up- and downregulated genes in green and orange, respectively). Right panel: base mean normalized per tRNA transcript across all samples.

Figure 4D:
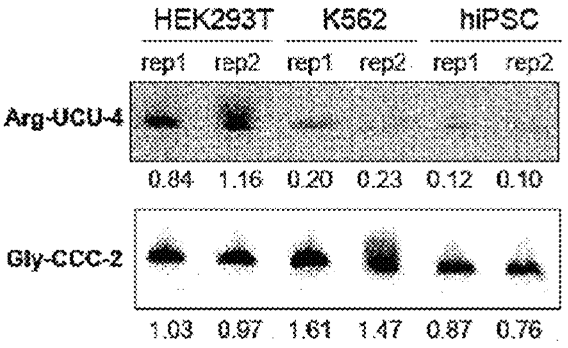

FIG. 4(D)-Northern blot analysis of tRNA-Arg-UCU-4 and tRNA-Gly-CCC-2 in HEK293T, K562, and hiPSCs (n=2, matched samples to those used for mim-tRNAseq). Band intensities were quantified by densitometry and normalized to the mean value for HEK293T.

Figure 4E:
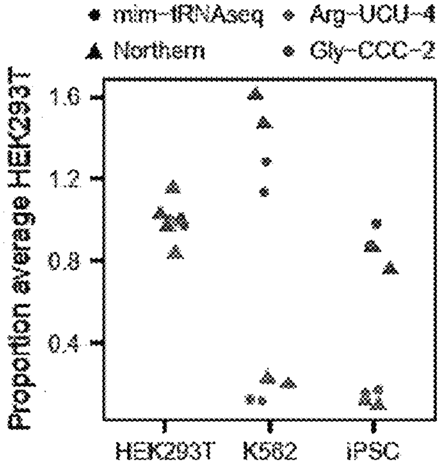

FIG. 4(E)-Relative abundance of IRNA-Arg-UCU-4 and tRNA-Gly-CCC-2 in HEK293T, K562, and hiPSCs measured by mim-tRNAseq (C) or northern blotting (D), normalized to the mean value for HEK293T (n=2, matched samples).

Figure 4F:
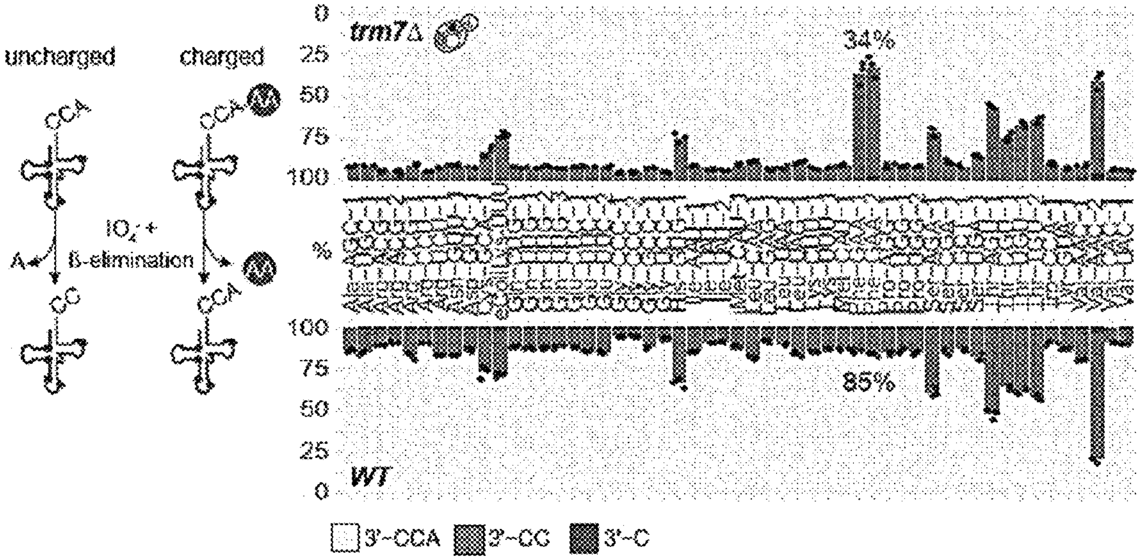

FIG. 4(F) tRNA charging analysis in wild-type and trm7Δ *S. cerevisiae*. Charged IRNA are represented by proportion of reads with 3'-CCA ends (light green, in %). Light green bars and tRNA-Phe-GAA labels, average charged tRNA fractions (% CCA; n=3).

FIG. 5. Near-complete modification readthrough in mim-tRNAseq datasets enables modification discovery and annotation FIG. 5(A)-Average proportion of stops (red) and misincorporation rates (blue) per nucleotide for all RNA unique transcripts (n=2) in *S. cerevisiae, S. pombe*, and *D. melanogaster* BG3-c2 cells and hiPSCs. x axis, canonical tRNA position at major sites with known RT barriers.

Figure 5A:
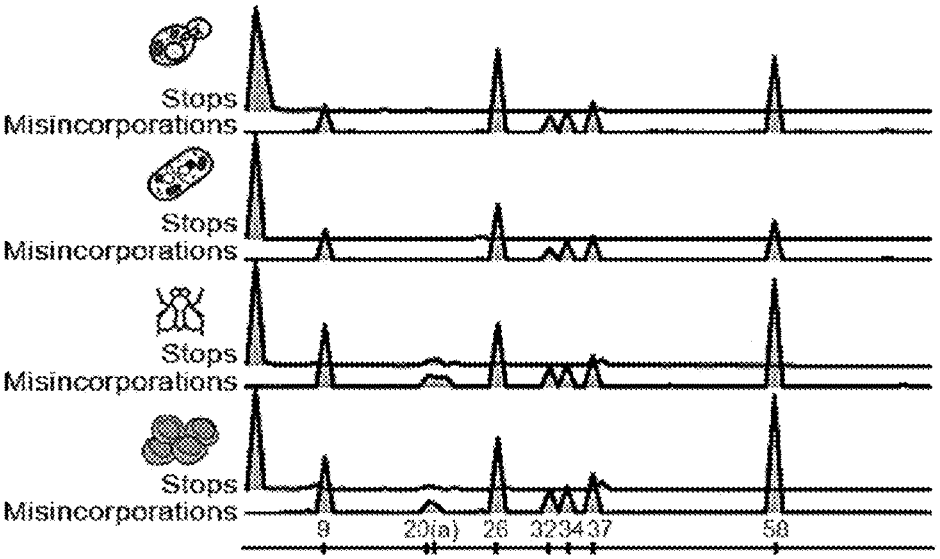
Figure 5B:
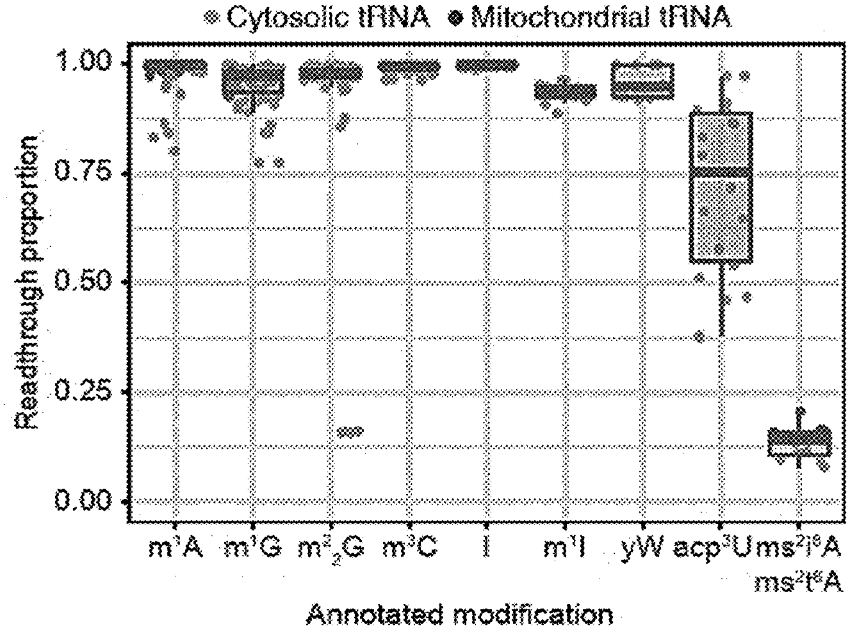

FIG. 5(B)-RT readthrough per annotated modification aggregated for cytosolic and mitochondrial tRNA from the four species.

Figure 5C:
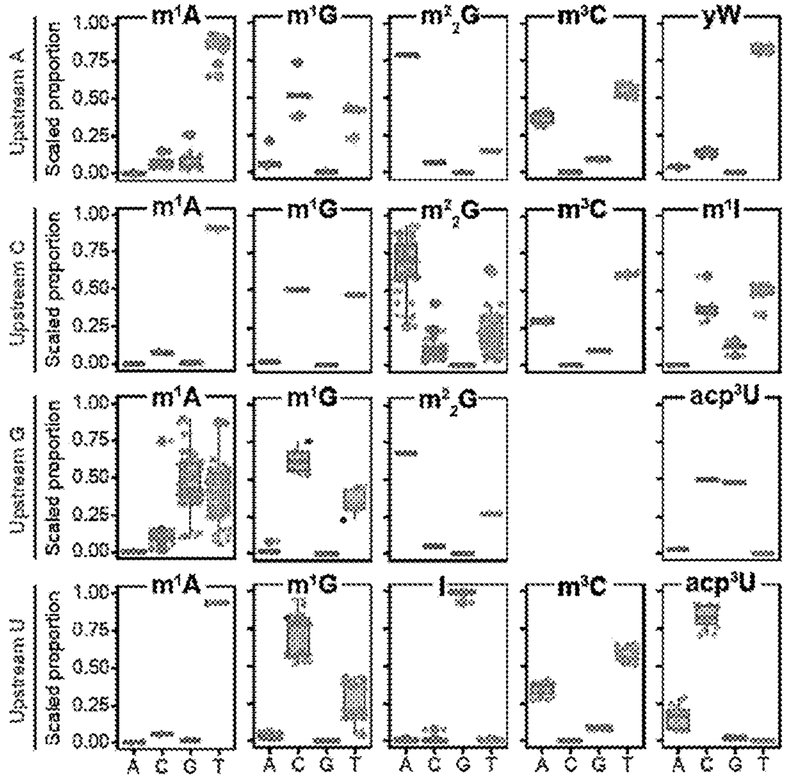

FIG. 5(C)-Boxplots of misincorporation signatures for annotated modified sites as in (B) (center line: median; box limits: upper and lower quartiles; whiskers: 1.5× interquartile range). Signatures stratified by upstream context (rows) and modification type (columns); proportion per nucleotide scaled to total misincorporation at this site.

Figure 5D:
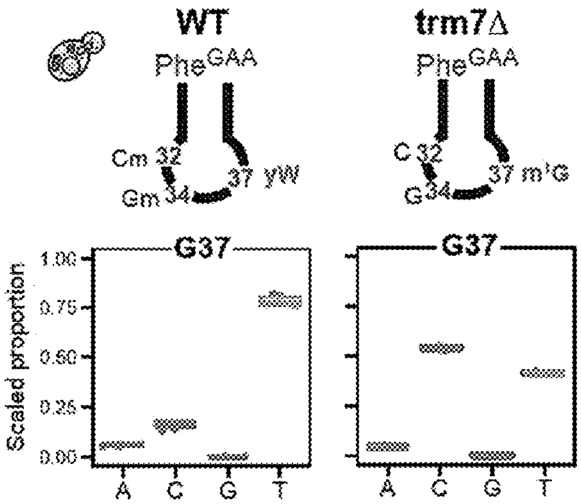

FIG. 5(D)-Boxplot of misincorporation signature at G37 of tRNA-Phe-GAA from WT and trm7Δ *S. cerevisiae* (n=3).

Figure 5E:
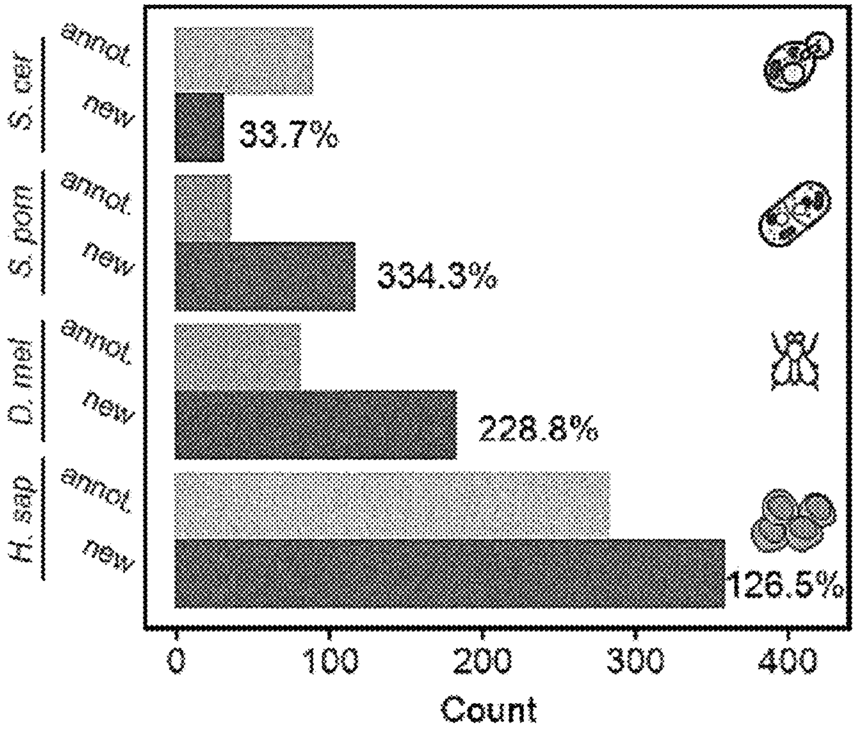

FIG. 5(E)-Modified site discovery by mim-tRNAseq ("new") compared with misincorporation-inducing modified sites previously annotated in MODOMICS ("annot."). Labels Indicate percentage of newly detected sites relative to annotated ones.

FIG. 6. Misincorporation rates in mim-tRNAseq reflect modification stoichiometry FIG. 6(A)-Global heatmap of average misincorporation proportions in *S. cerevisiae* per unique tRNA transcript with coverage above 2,000 reads (n=2; top bar graph, mean misincorporation per position; right bar graph, number of sites per transcript with detectable misincorporation signatures in ≥10% of reads spanning that position).

Figure 6A:
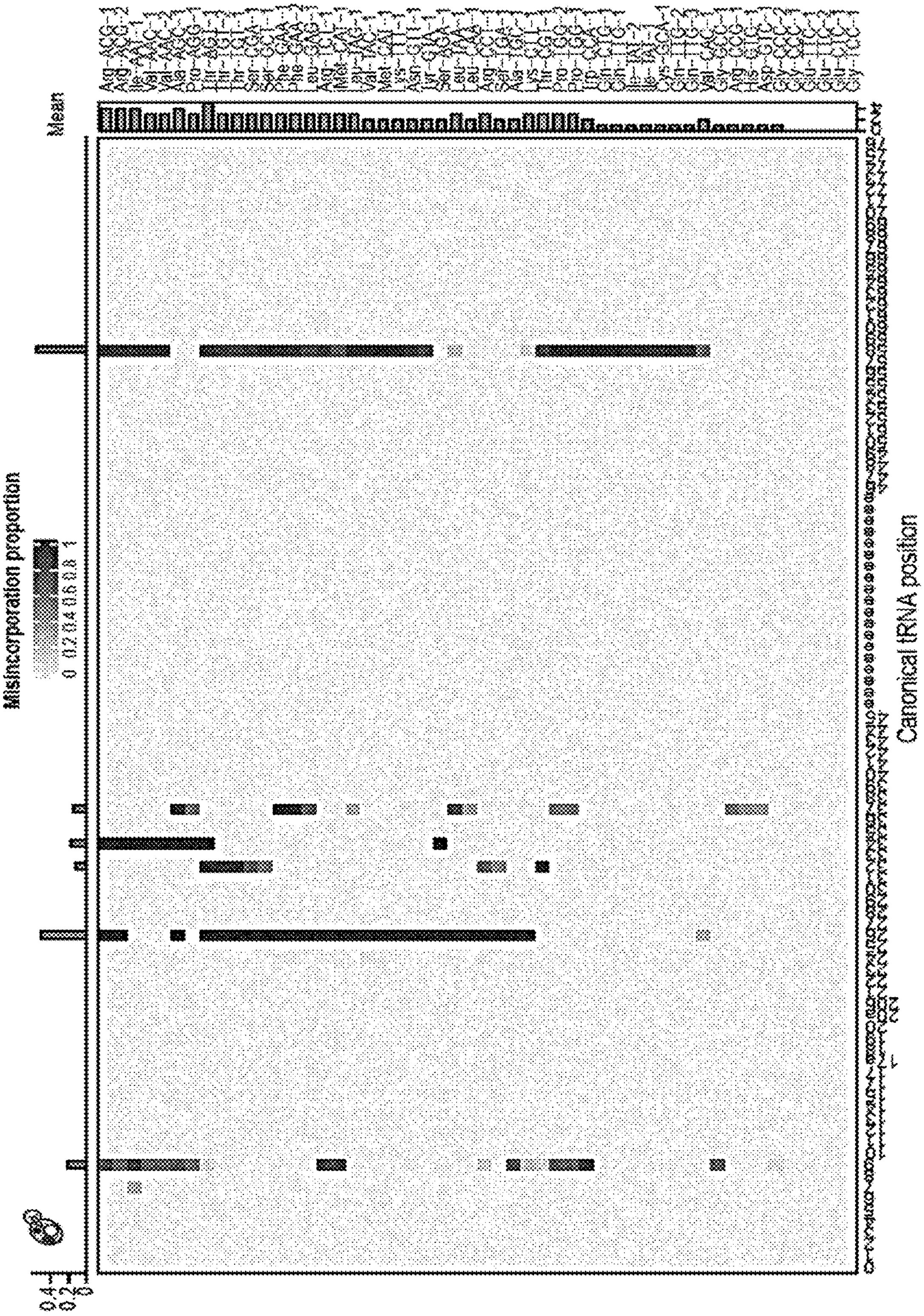
Figure 6B:
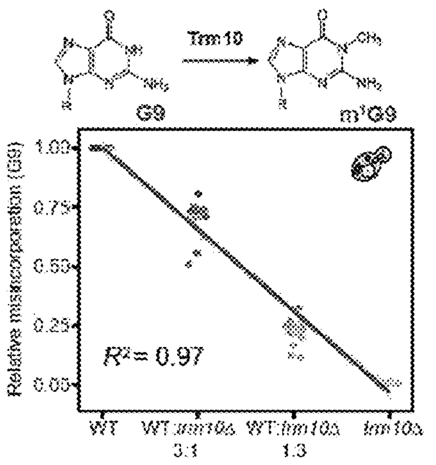

FIG. 6(B)-Relative misincorporation proportions at G9 in samples from wild-type (WT) *S. cerevisiae* and trm10Δ (lacking $m^1$G9) or mixes thereof (filtered for clusters with ≥10% misincorporation in WT and scaled to WT proportion; solid blue line, linear regression model; shaded gray, 95% CI).

Figure 6C:
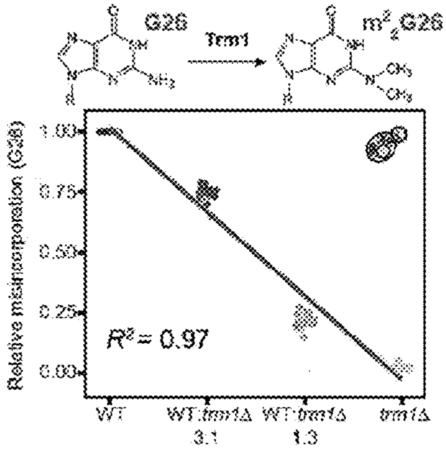

FIG. 6(C)-Analysis as in (B) but for misincorporation at G26 in samples from WT *S. cerevisiae* or trm1Δ (lacking $m^2{}_2$G26).

Figure 6D:
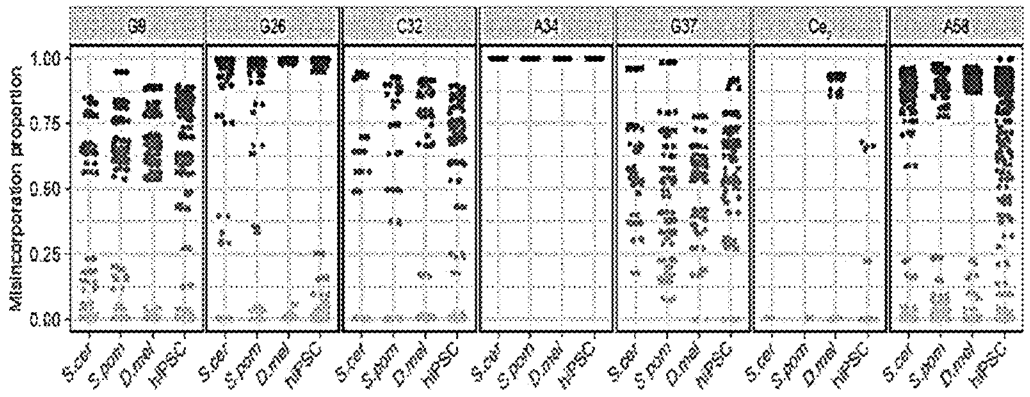

FIG. 6(D)-Misincorporation proportions per canonical nucleotide position and identity (aggregated per species; ez, second nucleotide of variable loop; n=2).

Figure 6E:
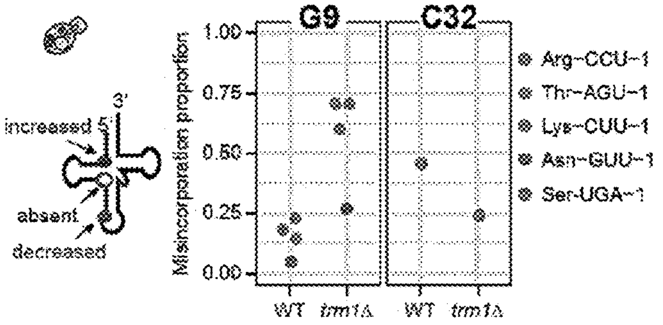

FIG. 6(E)-Significant changes in misincorporation rates in trm1Δ relative to WT *S. cerevisiae* (FDR-adjusted chi-square p≤0.01, $\log_2$ fold change ≥0.5, n=1).

The examples illustrate the invention.

Example 1—Design

Efficient Sequencing Library Generation from Native Eukaryotic tRNA Pools

To develop a method for high-resolution tRNA quantitation, it was focused on improving the efficiency of full-length cDNA synthesis from endogenously modified tRNAs by TGIRT. This enzyme can attach adapter sequences to RNA by template switching (Mohr et al., 2013), which circumvents potential hindrances to 3' adapter ligation and RT posed by tRNA structure (Katibah et al., 2014; Qin et al., 2016; Zheng et al., 2015). TGIRT can also read through a subset of Watson-Crick face modifications more efficiently than other commercial RTs (Li et al., 2017), albeit with reduced fidelity (Katibah et al., 2014; Qin et al., 2016; Zheng et al., 2015). Despite these advantages, RT stops at modified sites in tRNA are still pervasive in TGIRT-mediated reactions (Clark et al., 2016; Zheng et al., 2015), and cDNA yield is extremely low (Zhao et al., 2018; Zheng et al., 2015).

As TGIRT is active in a wide range of conditions (Mohr et al., 2013), it was asked whether its efficiency on tRNA templates can be further improved. To test this, tRNA pools were first purified from *S. cerevisiae* and human K562 cells by gel size selection of 60-100 nt RNAs from total RNA. These were then used, along with a synthetic unmodified *E. coli* tRNA-Lys-UUU, in template-switching TGIRT reactions. The cDNA yield from all templates was minimal under conditions previously used for tRNA sequencing (450 mM salt, 60 °C; Katibah et al., 2014; Qin et al., 2016; Zheng et al., 2015) but dramatically improved at lower temperatures and salt concentration (FIG. 1A). Although a considerable fraction of cDNAs were full length, some RT stops still occurred, and larger products potentially derived from two tRNA molecules linked by template switching were also present (FIG. 1A). To circumvent these issues and the known sequence bias of TGIRT during template switching (Xu et al., 2019), DNA adapters were introduced at the 3' end of tRNA with T4 RNA ligase 2. It was reasoned that the stable structure of mature tRNAs would not pose a challenge, as their 3' ends contain the stretch of at least two unpaired nucleotides that is required for efficient 3' adapter ligation (Zhuang et al., 2012). To further minimize potential bias and enable sample pooling prior to RT, four barcoded adapters were designed with limited potential to co-fold with tRNA and confirmed that they can be ligated to size-selected yeast tRNA pools with 89%-95% efficiency (FIG. 1B). Pooled adapter-containing tRNA samples were then subjected to primer-dependent RT with TGIRT in a low-salt buffer at 42 °C Strikingly, it as found that extending the reaction time eliminated nearly all premature RT stops on endogenously modified yeast and human tRNAs (FIG. 1B) without compromising template integrity. The primer for cDNA synthesis contained a 5' RN dinucleotide to ensure efficient cDNA circularization (Heyer et al., 2015; McGlincy and Ingolia, 2017) prior to PCR amplification with KAPA HiFi DNA Polymerase, which exhibits minimal bias for fragment length or GC content (Quail et al., 2011). This optimization enabled us to construct Illumina sequencing libraries starting from as little as 50 ng of endogenously modified tRNA with only five or six PCR cycles, minimizing sample input requirements and amplification bias.

a Comprehensive Computational Framework for tRNA Sequencing Data Analysis

We reasoned that the increase in full-length cDNA reads would reduce alignment ambiguity. However, given TGIRT's low fidelity at modified sites, it was expected many tRNA-derived reads to contain multiple mismatches to the reference genome. Another source of mismatches are non-templated nucleotides added to 3' cDNA ends by TGIRT and other RTs (Chen and Patton, 2001; Mohr et al., 2013). Such read extensions are penalized by most algorithms but can be recognized and dynamically processed ("soft-clipped") by some aligners. It was therefore asked how two short-read aligners commonly used for tRNA analysis-Bowtie (Langmead et al., 2009) and Bowtie 2 (Langmead and Salzberg, 2012)—would perform on a tRNA sequencing dataset from human HEK293T cells obtained with our improved library construction protocol (FIG. 1B).

We first generated a non-redundant reference of 420 mature tRNA transcripts from 596 curated nuclear- and mitochondrial-encoded tRNA genes retrieved from GtR- NAdb and mitotRNAdb (Chan and Lowe, 2016; Juhling et al., 2009; FIG. 2A; STAR methods). Alignment was performed with Bowtie or Bowtie 2 with parameters previously used for tRNA sequencing analysis (Clark et al., 2016; Cozen et al., 2015; Katibah et al., 2014; Qin et al., 2016; Zheng et al., 2015). Bowtie end-to-end alignment allows a maximum of three mismatches to the reference at any position. Its inability to distinguish modification-induced misincorporations from other mismatches can lead to data loss for highly modified tRNAs or misalignment for highly similar tRNAs. Indeed, only 25% of reads from our HEK293T tRNA library aligned with Bowtie, with a third of those mapping to multiple tRNA references (FIG. 2A). Trimming a fixed number of nucleotides from 5' read ends prior to alignment, which can remove non-templated nucleotides, expectedly improved mapping rates. The variable length of non-templated additions, however, makes such a trimming approach imprecise, and many trimmed reads still failed to align or were multi-mapped.

In contrast, Bowtie 2's lack of mismatch restrictions and ability to soft-clip read ends make it seem more suited for tRNA read mapping. High mismatch tolerance, however, compounds the problem of misalignment: while Bowtie 2 increased alignment rates of our HEK293T-derived dataset to 82%, most mapped reads (85%) could not be assigned to a single reference (FIG. 2A). Multi-mapping rates were similarly high when human QuantM-tRNAseq data were aligned using Bowtie 2 with the published settings (Pinkard et al., 2020) (85%). These high rates of data loss indicate that standard read alignment approaches are poorly suited to the complexity of tRNA sequencing data, with consequences for the accuracy of all downstream analyses.

Given these limitations, it was reasoned that an accurate tRNA read analysis workflow requires solutions to two main challenges: alignment bias against reads with modification-induced misincorporations and multi-mapping of reads from nearly identical tRNAs. To tackle the first issue, it was taken advantage of the comprehensive annotation of tRNA modifications in MODOMICS (Boccaletto et al., 2018) and used these data to enable position-specific mismatch tolerance during alignment (FIG. 2B, top panel). To achieve this, GSNAP was chose, an aligner designed for detecting complex variants in sequencing reads (Wu and Nacu, 2010). Unlike most other algorithms, GSNAP considers alignments to a reference and an alternative allele equally in SNP-tolerant alignment mode while also effectively soft-clipping read ends. To address multi-mapping, a strategy was devised to cluster reference sequences by a sequence identity (ID) threshold. Given that many reads still map to multiple references with the commonly used strategy of clustering only completely identical tRNA genes (ID=1; FIG. 2A) (Clark et al., 2016; Hoffmann et al., 2018; Zheng et al., 2015), it was reasoned that alignment ambiguity could be decreased by lowering the sequence ID threshold. To maintain isoacceptor resolution, only cluster tRNA transcripts were chosen that share an anticodon regardless of sequence ID.

On the basis of these premises, a new computational workflow was developed to suit the intricacies of tRNA sequencing data (FIG. 2B; STAR methods). To generate an alignment reference, mature tRNA transcript sequences are matched to MODOMICS to index known modified sites and clustered by anticodon according to sequence ID. Reads are aligned to the resulting indexed reference using GSNAP in SNP-tolerant mode. Unannotated potentially modified sites are detected by a mismatch rate of >10% and included in an updated index, followed by re-alignment of all reads with a more stringent tolerance to mismatches outside of modified sites to further boost alignment accuracy. To restore single-transcript resolution for subsequent analyses, a deconvolution algorithm was developed that assigns cluster-aligned reads to unique tRNA species (FIG. 2B, middle panel; STAR methods). For this, each cluster is assessed for single-nucleotide differences that distinguish unique tRNA sequences, on the basis of which each read is separated from the cluster "parent" and assigned to an individual transcript. Analysis of coverage, 3'-CCA, differential tRNA abundance, and modification profiling is then performed after read deconvolution (FIG. 2B, bottom panel). The entire computational framework for tRNA read alignment, analysis, and visualization is packaged in an open-source tool with a command-line interface and a broad set of customizable parameters.

This computational workflow dramatically improved both the efficiency and accuracy of tRNA read alignment. Both clustering and SNP tolerance at modified sites prevented data loss for defined tRNA subsets. A cluster ID of 0.95 maximized unique transcript resolution and minimized multi-mapping for human tRNAs, yielding 86% uniquely mapped and only 2.5% ambiguously aligned reads (FIG. 2C). Multi-mapping rates were 5-fold higher when only completely identical tRNA transcripts were clustered, resulting in data loss for selected tRNAs (e.g., tRNA-Asn-GTT-2 and tRNA-Pro-AGG-1). Aligning without SNP tolerance had similar effects, particularly for transcripts with inosine at position 34 (I34), which is encoded as an A but yields a G in cDNA libraries. The number of reads mapping to tRNA-Val-AAC, for example, increased by 300-fold in SNP-tolerant mode, and virtually all of these contained a G34. This high mismatch rate at I34 also presented obvious challenges for Bowtie and Bowtie 2. Almost no reads mapped to the I34-containing tRNA-Ser-AGA and tRNA-Pro-AGG with these algorithms, while many were assigned to tRNA-Ser-UGA and tRNA-Pro-UGG instead (FIG. 2D). The same dramatic under-representation of tRNA-Ser-AGA and tRNA-Pro-AGG was evident in published counts for QuantM-tRNAseq libraries, which were generated by Bowtie 2 local alignment. In contrast, our computational workflow yielded a more balanced representation of these four tRNA species for both mim-tRNAseq (FIG. 2D) and QuantM-tRNAseq libraries. The choice of read alignment parameters can thus yield very different tRNA abundance estimates.

Example 2—Results

The mim-tRNAseq Workflow Alleviates tRNA Sequencing Bias

To benchmark our workflow, mim-tRNAseq was used to analyze HEK293T tRNAs and compared our results with those published for the same cell type with DM-tRNAseq (Zheng et al., 2015) and from the closely related HEK293 T-Rex Flp-IN line (Lin et al., 2014) obtained with hydro-tRNAseq (Gogakos et al., 2017) or QuantM-tRNAseq (Pinkard et al., 2020). To distinguish experimental from computational differences, the published datasets was also re-analyzed using the computational pipeline as described herein (FIG. 2B). Reads from tRNA isotypes with a single known barrier to RT (Boccaletto et al., 2018) were substantially overrepresented in DM-tRNAseq (tRNA-Val, 19%-21%) and hydro-tRNAseq (tRNA-Gly, 30%) compared with our dataset (~6%). In QuantM-tRNAseq, tRNA-Arg constituted 16% of published tRNA counts versus 3.5% in hydro-tRNAseq, 7%-9% in DM-tRNAseq, and 9% in our dataset.

Figure 2E:
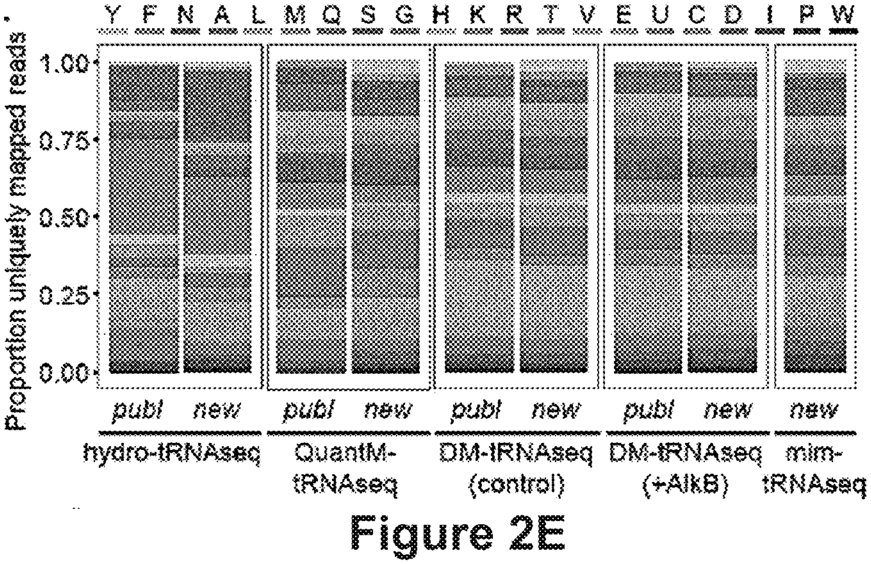

This isotype over-representation persisted regardless of alignment algorithm (FIG. 2E, "publ" versus "new"), suggesting that it originated during library construction. In contrast, tRNA-Tyr, which has five known RT-blocking modifications, constituted ~4% of mapped reads in our dataset versus only 1% for published hydro-tRNAseq and DM-tRNAseq counts and 0.3% for QuantM-tRNAseq. This under-representation was largely relieved when DM-tRNAseq and QuantM-tRNAseq datasets were re-analyzed with our computational pipeline (FIG. 2E). Thus, mim-tRNAseq recovers highly modified tRNAs more efficiently than current methods through a combination of advances in library construction and data analysis.

mim-tRNAseq Improves tRNA coverage and abundance estimates

We extended our analysis to single-cell and multicellular eukaryotes by preparing mim-tRNAseq libraries from exponentially growing *S. cerevisiae* and *S. pombe*, as well as *D. melanogaster* BG3-c2 cells and human induced pluripotent stem cells (hiPSCs) with a normal karyotype. The optimal cluster ID threshold was determined as 0.90 for budding yeast and 0.95 for fission yeast, *Drosophila*, and human tRNA pools. These settings yielded between 85% and 91% of uniquely mapped reads (FIG. 3A), with a median of 65%-83% full-length ones (FIGS. 3B and 3C). In contrast, unique alignment rates were lower for datasets from DM-tRNAseq and QuantM-tRNAseq and for libraries that were generated with the standard TGIRT protocol. tRNA coverage in those datasets also had substantial 3' end bias, consistent with RT stops at modified sites. Accordingly, unique tRNA transcripts were represented by a median of <11% and 6% full-length reads in DM-tRNAseq and QuantM-tRNAseq, respectively.

Most reads in mim-tRNAseq datasets mapped to cytosolic tRNA, with mitochondrial tRNA fractions ranging from 0.5% in budding yeast to 3% in hiPSCs. Importantly, nearly all mapped reads (>96%) spanned the post-transcriptionally added 3'-CCA stretch, indicating that they originate from mature tRNA. This was not due to bias toward A-ending RNA species, as our workflow accurately captured the 3:1 ratio of two synthetic *E. coli* tRNA-Lys-UUU tRNAs with either 3'-CCA or 3'-CC spiked in prior to library construction. cDNA circularization also did not introduce appreciable length bias, as tRNA coverage after alignment mirrored initial cDNA size (FIGS. 3B and 1B). Moreover, circularization sequence context is very similar for all cDNAs, as most have a stretch of one to three non-templated Ts at their 5' ends, corresponding to non-templated A added to cDNA 3' ends by TGIRT, which were effectively soft-clipped during GSNAP alignment. Indeed, nucleotide frequencies downstream of non-templated nucleotides were highly similar to those obtained by aligning the 5' ends of predicted tRNA transcripts.

We asked whether these experimental and computational advances would enable more accurate tRNA quantitation. It was first sought to compare our measurements of absolute tRNA abundance with data obtained with an orthogonal, hybridization-based approach. Absolute RNA quantitation by, for example, Northern blotting or arrays requires highly specific probes and careful comparisons of signal in serial sample dilutions to calibration curves with known target amounts. The design of specific probes for tRNAs, however, is extremely challenging: even with full-length probes, a difference of at least 8 nt is required to avoid cross-hybridization (Dittmar et al., 2004, 2006). Probe design is particularly problematic for human tRNA pools, which can contain >400 tRNA species from 57 anticodon families. As the major tRNA transcript for each anticodon family can differ among cell types (Ishimura et al., 2014), probe selection can unduly influence measurement accuracy. In contrast, the 41 anticodon families of *S. cerevisiae* consist of only 54 tRNA species, and most major anticodon variants differ sufficiently in sequence to be distinguished by hybridization. Therefore fluorescence intensity measurements for 39 of the 41 budding yeast anticodon families obtained by direct hybridization to a tRNA microarray (Tuller et al., 2010) were compared to the fraction of reads mapping to those anticodon families in mim-tRNAseq datasets. This comparison yielded Pearson's r=0.75 ($p=3.8\times10^{-8}$), corroborating the quantitative nature of mim-tRNAseq.

The main regulatory elements for tRNA transcription are intrinsic and overlap with conserved structural regions of mature tRNAs, and it remains unclear how selective tRNA gene expression is achieved in metazoans (Ishimura et al., 2014; Kutter et al., 2011; Schmitt et al., 2014). In rapidly growing yeast cells, however, nearly all tRNA loci are transcribed (Harismendy et al., 2003; Roberts et al., 2003). tRNA gene copy number thus positively correlates with the abundance of tRNA anticodon families during exponential growth measured by hybridization ($R^2$=0.47 in microscale thermophoresis and $R^2$=0.60 in tRNA microarray; Jacob et al., 2019; Tuller et al., 2010). The superior resolution of mim-tRNAseq were leveraged to probe this relationship at the level of individual tRNA transcripts (FIG. 3D). The highest correlation was obtained between gene copy number and tRNA abundance reported so far (adjusted $R^2$=0.92 for *S. cerevisiae* and $R^2$=0.91 for *S. pombe*, $p<3.71\times10^{-30}$), further underscoring the quantitative nature of mim-tRNAseq. This correlation decreased substantially for a *S. cerevisiae* library from budding yeast generated by template switching in otherwise identical RT conditions ($R^2$=0.61), consistent with 3' sequence preferences of TGIRT in this setup (Xu et al., 2019). An even more drastic reduction was seen in a *S. cerevisiae* library generated with Superscript III ($R^2$=0.31), which displayed substantial 3' end coverage bias despite high rates of unique read alignment.

The correlation between gene copy number and tRNA abundance was also lower in *Drosophila* BG3-c2 cells (adjusted $R^2$=0.79) and hiPSCs (adjusted $R^2$=0.62). The values were similar regardless of whether copy numbers for all predicted human tRNA genes or only the high-confidence tRNA gene set were used. These findings are consistent with differential tRNA gene use in distinct cell types (Dittmar et al., 2006; Ishimura et al., 2014; Kutter et al., 2011; Schmitt et al., 2014) and highlight that mechanisms beyond gene copy number shape metazoan tRNA pools.

mim-tRNAseq Captures Differences in tRNA Abundance and Aminoacylation

To establish whether mim-tRNAseq can accurately detect differences in tRNA abundance, first the tRNA pools of karyotypically normal hiPSCs were compared with those in two aneuploid human cell lines (K562 and HEK293T). Of the 368 cytosolic tRNA species resolved quantitatively by mim-tRNAseq, 205 were undetectable in one or more cell lines (≤0.005% of tRNA-mapped reads). Remarkably, more than half of the detectable tRNAs were differentially expressed, some by up to 3 orders of magnitude (adjusted $p<0.05$; FIG. 4A). In contrast, the relative levels of tRNAs with a given anticodon differed by only up to 1.7-fold among the three cell lines (FIG. 4B). Of the 47 tRNA anticodon families passing our detection threshold, 11 differed in abundance between HEK293T cells and hiPSCs, and 21 differed in abundance between K562 cells and hiPSCs (FIG. 4B). Each cell line exhibited a distinct pattern of tRNA expression, with differences being more pronounced for low-abundance transcripts (FIG. 4C; base mean expression given by line plot in rightmost panel). These data suggest that different cell types can converge on similar anticodon pools via distinct tRNA transcript subsets, possibly through the relatively stable expression of major tRNA isodecoders (Kutter et al., 2011).

We validated the changes in relative abundance by Northern blotting for two tRNA species: tRNA-Arg-UCU-4 and tRNA-Gly-CCC-2, which differ sufficiently from their isodecoders to avoid probe cross-hybridization and represent tRNAs with low and high abundance. tRNA-Arg-UCU-4 and its mouse ortholog are highly expressed in the central nervous system and are also present at low levels in HEK293T cells (Ishimura et al., 2014; Torres et al., 2019). mim-tRNAseq detected 6- to 8-fold lower levels of tRNA-Arg-UCU-4 in K562 and hiPSCs versus HEK293T, and a similar 5- to 10-fold decrease was observed by Northern blotting (FIGS. 4D and 4E). Differential abundance estimates by mim-tRNAseq and Northern blotting were also highly concordant for the abundant tRNA-Gly-CCC-2 (~1% of tRNA-mapped reads; FIGS. 4D and 4E).

We then confirmed the ability of mim-tRNAseq to accurately measure tRNA aminoacylation. Charged tRNAs have periodate-resistant 3' ends and can be quantified as a fraction of tRNAs with 3'-CCA versus 3'-CC following oxidation and β-elimination (Evans et al., 2017). mim-tRNAseq data from oxidized tRNA of wild-type (WT) yeast and a trm7Δ strain were compared, which has a tRNA-Phe-GAA charging defect (Han et al., 2018). This defect was evident by a 2.5-fold decrease in 3'-CCA proportions for both tRNA-Phe-GAA isodecoders in tRNA pools from trm7Δ cells in the absence of other changes in aminoacylation status (FIG. 4F). Thus, mim-tRNAseq enables the sensitive and accurate quantitation of differences in tRNA abundance or charging.

Improved Readthrough Facilitates the Discovery and Annotation of Watson-Crick Face tRNA modifications Mismatches to reference and/or premature RT stop signatures are frequently used to detect Watson-Crick face RNA modifications (Clark et al., 2016; Ebhardt et al., 2009; Hauenschild et al., 2015; Katibah et al., 2014; Li et al., 2017; Motorin et al., 2007; Qin et al., 2016; Ryvkin et al., 2013; Safra et al., 2017; Zheng et al., 2015), but their analysis is prone to both experimental and computational artifacts (Sas-Chen and Schwartz, 2019). As tRNA-derived reads are particularly misalignment-prone with standard algorithms (FIGS. 2A and 2D), this could affect the accuracy of modification calling.

In contrast, mim-tRNAseq abrogated nearly all RT stops and yielded reproducibly high levels of mismatches coinciding with frequently modified tRNA positions (FIG. 5A). The extent of readthrough was quantified at annotated Watson-Crick face tRNA modifications by calculating the proportion of aligned reads extending past a given position. The minimum value in a 3-nt window centered around was taken to avoid readthrough overestimation. The median readthrough values that were obtained with this approach were ~100% at the most common RT barriers in tRNA such as $m^1A$, $N^1$-methylguanosine ($m^1G$), $N^2$, $N^2$-dimethylguanosine ($m^2{}_2G$), and No-methylcytosine ($m^3C$), as well as bulkier modifications such as wybutosine (yW) and other wyosine derivatives (FIG. 5B). All 162 annotated Watson-Crick face modifications in tRNA from budding yeast (100%) and 232 of the 250 annotated ones in human tRNA (93%) had a readthrough efficiency of >80%. This is due to both experimental and computational advances, as readthrough was much lower in libraries generated with standard TGIRT conditions or in DM-tRNAseq. There was a notably large variation in bypass of the same modification type in different tRNAs in libraries made with Superscript IV.

The only RT blocks remaining in mim-tRNAseq datasets were at rare hypermodified positions. These include 2-methylthio-derivatives of A37 ($ms^2t^6A$/$ms^2i^6A$ in human cytosolic tRNA-Lys-UUU and 3-4 mitochondrial tRNAs in *Drosophila* and human cells) and rare stretches of two modified sites ($m^2{}_2G26/27$ and 20/20a $N^3$-[3-amino-3-carboxypropyl]-uridines [$acp^3U$]; FIGS. 5B, S2I, S4D, and S4E). These few remaining RT stops do not affect tRNA quantitation, as the cDNA fragments derived from them are sufficiently long (39-56 nt) for unambiguous read alignment with our pipeline.

We then examined whether different modifications are marked by specific signatures of nucleotide misincorporation. This can depend on the processivity and fidelity of an RT, the reaction conditions, and the sequence context of the modified site (Hauenschild et al., 2015; Katibah et al., 2014; Li et al., 2017; Qin et al., 2016; Safra et al., 2017). Signature analysis is especially challenging when RT stops are pervasive, as mismatches at read ends stemming from non-templated nucleotide addition during RT may manifest as misincorporation and lead to spurious modification calls (Sas-Chen and Schwartz, 2019). As mim-tRNAseq enables near-complete modification readthrough (FIG. 5B), misincorporation patterns were examined at annotated sites as a function of modification type and sequence context. Distinct and highly reproducible misincorporation signatures were found at specific modifications (FIG. 5C). The ones at $m^1G$, $m^2{}_2G$, and $m^3C$ were largely independent of sequence context, whereas those at $m^1A$ and $acp^3U$ were influenced by the upstream template nucleotide (FIG. 5C). Also distinct signatures were observed for wyosine derivatives, inosine and M-methylinosine ($m^1I$), where the tRNA sequence space is not sufficiently large to explore the impact of sequence context. In contrast, misincorporation signatures of Superscript IV were much less specific for distinct modifications, with a high prevalence of T mismatches regardless of modification type. A recent comparison of 13 RTs found a similar lack of distinguishable signatures for $m^1G$ and $m^2{}_2G$ (Werner et al., 2020).

To validate the specificity of these signatures, misincorporation patterns at G37 in tRNA-Phe-GAA from WT and trm7Δ yeast were compared (FIG. 5D). The conversion of $m^1G37$ to yW in this tRNA requires 2'-O-methylation of C32 and G34 by Trm7 (Guy et al., 2012). Accordingly, the misincorporation signature at G37 in tRNA-Phe-GAA from trm7Δ cells was distinct from that in WT (FIG. 5D) and nearly identical with that of $m^1G$ in our aggregate analysis (FIG. 5C).

This remarkable consistency enables the use of misincorporation signatures not only for mapping RNA modifications but also for predicting their identity. The datasets from *S. cerevisiae, S. pombe*, and *Drosophila* BG3-c2 cells and human cells were therefore probed for misincorporation-inducing modifications not annotated in MODOMICS. Such sites were identified by a mismatch frequency of >10% and the presence of a distinct misincorporation signature to limit spurious modification calls due to genomic misannotation or SNPs. Modification type was then predicted by combining information on the canonical tRNA position, nucleotide type, and misincorporation signature in comparison with known sites (FIG. 5C). Performing this analysis with single-transcript resolution revealed many uncatalogued modifications (FIG. 5E), including 30 sites in *S. cerevisiae* and 358 sites in human tRNAs, despite comprehensive existing annotation. Discovery rates were higher in poorly annotated species such as *S. pombe* and *D. melanogaster*. Our predictions generally agreed with prior annotation of modified sites based on RT stops and/or misincorporations, with some important differences. First, one $m^1G9$ site, two $m^2_2G26$ sites, and seven $m^1A58$ sites were identified in tRNAs from *S. pombe*, which had not been detected by hydro-tRNAseq (Arimbasseri et al., 2015). Second, no detectable misincorporation was found at G37 in human tRNA-Pro-AGG or C47d in human tRNA-Ser-AGA and tRNA-Ser-CGA, although these positions have been annotated as $m^1G37$ and $m^3C47d$, respectively (Arimbasseri et al., 2016; Clark et al., 2016). These differences likely result from our workflow's improved resolution of nearly identical tRNAs, as human tRNA-Pro-UGG and tRNA-Ser-UGA contain $m^1G37$ and $m^3C47d$, respectively (FIG. 2D). These data demonstrate that mim-tRNAseq can map potentially modified tRNA sites and predict modification type with high sensitivity and specificity.

Accurate Quantitation of RNA Modification Stoichiometry on the Basis of Misincorporation Rates Proportions of RT stops and/or misincorporations are widely used to estimate RNA modification levels (Arimbasseri et al., 2015; Clark et al., 2016; Gogakos et al., 2017; Ryvkin et al., 2013), but whether such measurements are quantitative is unknown. Misincorporation rates at individual modified positions in mim-tRNAseq datasets varied remarkably across tRNA species (FIG. 6A) despite efficient readthrough (FIG. 5B). To test whether this variation reflects modification stoichiometry, endogenously modified tRNA were sequenced from WT and mutant yeast lacking $m^1G9$ (trm10Δ) (Jackman et al., 2003) or $m^2_2G26$ (trm1Δ) (Ellis et al., 1986) pooled in defined ratios prior to library construction. Misincorporations were predictably absent at G9 or G26 sites in samples from the knockout strains. Strikingly, their rates had a near-perfect linear correlation to initial pooling ratios in mixed samples ($R^2$=0.97; FIGS. 6B and 6C). Mismatch proportions in mim-tRNAseq datasets thus accurately reflect the stoichiometry of $m^1G$ and $m^2_2G26$, and possibly all other misincorporation-inducing modified tRNA bases. Calibration curves with endogenously modified tRNAs are not feasible for all misincorporation-inducing modifications (FIG. 5B), however, as some of them are essential for cell viability (Anderson et al., 1998; Gerber and Keller, 1999).

These findings enabled us to profile modified tRNA fractions with single-transcript resolution in cells from four eukaryotic species. Misincorporation rates were ~100% at all instances of 134 and of wyosine derivatives at position 37, suggesting these modifications are present in stoichiometric levels. A similar trend was observed for $m^2_2G26$, with a clear separation between a majority of fully modified tRNAs and a very small number of transcripts with 10%-30% misincorporation. In contrast, the modified fractions of $m^1G$, $m^3C$, and $m^1A$ varied substantially among individual tRNAs independently of sequence context. Instances of very high misincorporation were detectable for all three modifications ($m^1A$, 100%; $m^3C$, 94%; $m^1G$, 88%), indicating that mim-tRNAseq can capture high stoichiometry at these sites if it is present (FIG. 6D). However, some tRNAs seem to contain these modifications at sub-stoichiometric levels. Sub-stoichiometric $m^3C32$ and $m^1G37$ are consistent with the regulatory rather than structural roles of modifications within the tRNA anticodon loop. The stoichiometry of $m^1G37$ measured by mim-tRNAseq ranged from 14% to 80% in tRNAs from the four eukaryotic species. In bacteria, $m^1G37$ in tRNA-Pro-UGG and RNA-Pro-GGG aids in reading frame maintenance (Gamper et al., 2015; Maehigashi et al., 2014). Eukaryotic cells, however, lack tRNA-Pro-GGG because of toxicity from its high miscoding capacity (Pernod et al., 2020). A recent study estimated $m^1G37$ stoichiometry in bacterial tRNA-Pro-UGG by primer extension at 68% in *E. coli* and 73% in *Salmonella enterica* (Masuda et al., 2019). Our workflow estimated $m^1G37$ stoichiometry at 53% in yeast tRNA-Pro-UGG and 72% for tRNA-Leu-UAA. Gel-based primer extension assays with AMV RT, which is blocked by $m^1G$, were consistent with these measurements, providing an orthogonal validation of mim-tRNAseq modification stoichiometry estimates.

In contrast to the regulatory roles of anticodon loop modifications, $m^1A58$ is important for the maturation and stability of initiator tRNA-Met in yeast (Anderson et al., 1998) and may play a similar role in other eukaryotic tRNA species. A sequence comparison of budding yeast tRNAs with high or low $m^1A58$ levels revealed no notable differences, however, indicating that sequence alone is unlikely to be a major determinant of modification stoichiometry at this position.

To examine whether the stoichiometry of misincorporation-inducing tRNA modifications differs in distinct cell types or states, log odds ratios of misincorporation proportions were calculated across all tRNA positions (see STAR methods). There were very few statistically significant changes when comparing mim-tRNAseq datasets from hiPSCs and HEK293T or K562 cells, suggesting that most tRNAs are modified to a similar extent in these cell lines. A comparison of datasets from WT and trm10Δ or trm1Δ yeast, however, revealed the striking precision of our approach in detecting transcripts with large reductions in $m^1G9$ or $m^2_2G26$. Unexpectedly, in trm1Δ yeast cells that lack $m^2_2G26$, there were also differences in modification levels at other tRNA sites. These included a 3- to 6.5-fold increase in $m^1G9$ levels in four tRNAs (tRNA-Lys-CUU-1, tRNA-Thr-AGU-1, tRNA-Arg-CCU-1, and tRNA-Asn-GUU-1) and a 2-fold decrease in $m^3C32$ of tRNA-Ser-UGA-1. $m^1G9$ levels in tRNA-Lys-CUU-1 and tRNA-Thr-AGU-1 also increase upon $Trm^{10}$ overexpression in yeast (Swinehart et al., 2013). Sequence comparisons between tRNAs with increased versus unchanged $m^1G9$ levels in trm1Δ cells indicate that a U7: A66 pair rather than G7: C66 pair may be linked to $m^1G9$ hypermethylation in the absence of $m^2_2G26$. These findings reveal an interdependence between Watson-Crick face modifications at distinct tRNA sites and suggest that their stoichiometry is determined by structural features.

Example 3—Discussion

The abundance, charging, and modification status of individual tRNA species can differ in distinct cellular environments. Measuring these properties on a global scale, however, has not been feasible because of technical limitations. No library construction method so far has allowed the efficient reverse transcription of these highly modified RNAs, while the lack of computational tools suited to the complexity of tRNA sequencing data has been another major methodological gap.

We describe conditions that permit near-complete tRNA modification readthrough by TGIRT, dramatically improving cDNA yield and the fraction of full-length products from tRNA templates. All but one rare tRNA modification roadblock are resolved by mim-tRNAseq, which alleviates the bias of existing tRNA quantitation methods toward low-modified tRNAs species. Our library construction protocol circumvents the need to purify enzymes for modification removal (Zheng et al., 2015) or RT (Zhou et al., 2019), which can introduce unwanted variation. Also described are multiple conceptual advances in the analysis of tRNA sequencing data, including the use of modification annotations, which permits position-specific mismatch tolerance during read alignment. Collectively, these advances enable the efficient and accurate mapping and analysis of tRNA-derived reads with single-transcript resolution.

One poignant example of the substantial improvements in our computational workflow concerns IRNAs with 134, which is essential for wobble pairing during decoding. Inosines are interpreted as cytosines during RT, resulting in the stoichiometric presence of G in sequencing reads. When using Bowtie or Bowtie 2 to align tRNA datasets from human cells, it was found that reads with G34 were frequently mapped to nearly identical tRNA isoacceptors with U34. Such misalignment can have wide-ranging implications, as it would not only skew abundance estimates but can also lead to spurious conclusions about tRNA modification status and stoichiometry. These findings highlight the importance of both sensitivity and accuracy of read alignment in the context of analyzing tRNA transcriptomes.

The robust misincorporation signatures deposited by TGIRT reveal the location, type, and stoichiometry of Watson-Crick face base modifications in tRNA. Calibration measurements of observed versus expected modified fractions in existing approaches for sequencing-based modification analysis are either lacking (Ryvkin et al., 2013; Zheng et al., 2015) or display a non-linear relationship (Zhou et al., 2019), likely because of persistent RT stops. In contrast, mim-tRNAseq enables efficient readthrough of almost all tRNA modifications, while modification ID is also discernible by highly specific misincorporation patterns. Improved readthrough permits accurate measurements of modification stoichiometry from misincorporation rates alone, evident from calibration curves with near-perfect linear regression for $m^1G$ and $m^2_2G$ ($R^2$=0.97). Performing this calibration with mixtures of endogenously modified tRNA pools shows that our entire workflow is free of bias toward low-modified tRNAs.

Remarkably, although some tRNA positions are almost always fully modified (e.g., $m^2_2$G26 and 134), others are sub-stoichiometric in some tRNA species. This is in line with a model in which some modifications are deposited because of overlapping substrate specificities in RNA modification enzymes (Phizicky and Alfonzo, 2010). Indeed, methylation at G9 in some yeast tRNAs is enhanced when they lack $m^2_2$G26, while methylation of C32 is decreased, suggesting that a tRNA conformational change upon $m^2_2$G26 loss (Steinberg and Cedergren, 1995) might change the affinity of other modification enzymes for individual tRNAs.

In summary, mim-tRNAseq is a sensitive and accurate start-to-finish technique for quantitation of tRNA abundance and charging, which also reports on the presence and stoichiometry of misincorporation-inducing RNA modifications. The robust library construction workflow and the easy-to-use and freely available computational toolkit make mim-tRNAseq broadly applicable for studying key aspects of tRNA biology in a range of organisms and cell types. Our experimental workflow can also be implemented for the discovery and quantitation of modified sites in other RNA species.

Example 4—Material and Methods

| REAGENT or RESOURCE | SOURCE | IDENTIFIER |
|---|---|---|
| | Commercial reagents | |
| mTeSR1 | STEMCELL Technologies | Cat# 85850 |
| Micro Bio-Spin P30 columns, RNase-free | Bio Rad | Cat# 7326251 |
| Glycogen | Ambion | Cat# AM9510 |
| T4 Polynucleotide Kinase | New England Biolabs | Cat# M0201L |
| T4 RNA ligase 2 (truncated KQ) | New England Biolabs | Cat# M0373L |
| SUPERase In | Ambion | Cat# AM2694 |
| TGIRT | InGex | Cat# TGIRT50 |
| Superscript III | Invitrogen | Cat# 18080044 |
| AMV RT | Promega | Cat# M9004 |
| CircLigase ssDNA ligase | Lucigen | Cat# CL4115K |

| REAGENT or RESOURCE | SOURCE | IDENTIFIER |
|---|---|---|
| KAPA HiFi DNA Polymerase | Roche | Cat# KK2102 |
| DNA Clean&Concentrator-5 PCR purification kit | Zymo Research | Cat# D4013 |
| Immobilon NY+ | Millipore | Cat# INYC00010 |
| | Deposited data | |
| Raw and analyzed sequencing data | This paper | GEO: GSE152621 |
| DM-tRNAseq raw data for *H. sapiens* HEK293T | Zheng et al., 2015 | GEO: GSE66550 |
| Hydro-tRNAseq raw data for *H. sapiens* HEK293 T-Rex Flp-IN | Gogakos et al., 2017 | GEO: GSE95683 |
| QuantM-tRNAseq raw data for *H. sapiens* HEK293 T-Rex Flp-IN | Pinkard et al., 2020 | GEO: GSE141436 |

Experimental Models: Cell Lines

| | | |
|---|---|---|
| *D. melanogaster* BG3-c2 cells | P. Becker, LMU | N/A |
| HEK293T cells | O. Griesbeck, MPIN | N/A |
| HPSI0214i-kucg_2 cells | Kilpinen et al., 2017; ECACC | Cat# 77650065 |

Experimental Models: Organisms/Strains

| | | |
|---|---|---|
| *S. cerevisiae*: strain BY4741 | Euroscarf | N/A |
| *S. cerevisiae*: strain BY4741 trm1Δ::kanMX | Euroscarf | N/A |
| *S. cerevisiae*: strain BY4741 trm7Δ::kanMX | Euroscarf | N/A |
| *S. cerevisiae*: strain BY4741 trm10Δ::kanMX | Euroscarf | N/A |
| *S. pombe*: strain ED668 h+ | S. Braun, LMU | N/A |

Oligonucleotides

| REAGENT or RESOURCE | SOURCE | IDENTIFIER |
|---|---|---|
| RNA sequences, primers for library construction, and probes for primer extension and Northern blotting, | This paper | N/A |
| Software and algorithms | | |
| mim-tRNAseq v0.2.5.6 | This paper | https://github.com/nedialkova-lab/mim-tRNAseq |
| Bowtie v1.2.2 | Langmead et al., 2009 | http://bowtie-bio.sourceforge.net/index.shtml |
| Bowtie2 v2.3.3.1 | Langmead and Salzberg, 2012 | http://bowtie-bio.sourceforge.net/bowtie2/index.shtml |
| GSNAP v2019-02-26 | Wu and Nacu, 2010 | http://research-pub.gene.com/gmap/ |
| Samtools v1.11 | Li et al., 2009 | http://samtools.sourceforge.net/ |
| Bedtools v2.29.2 | Quinlan and Hall, 2010 | https://bedtools.readthedocs.io/en/latest/ |
| BLAST+ v2.9.0 | Camacho et al., 2009 | https://blast.ncbi.nlm.nih.gov |
| Infernal v1.1.2 | Nawrocki and Eddy, 2013 | http://eddylab.org/infernal/ |
| usearch v10.0.240_i86linux32 | Edgar, 2010 | https://www.drive5.com/usearch/ |
| R/DESeq2 v1.26.0 | Love et al., 2014 | https://bioconductor.org/packages/release/bioc/html/DESeq2.html |
| R/ComplexHeatmap v2.2.0 | Gu et al., 2016 | https://www.bioconductor.org/packages/release/bioc/html/ComplexHeatmap.html |
| Python/Biopython v1.70 | Cock et al., 2009 | https://biopython.org/ |

Data and Code Availability

The accession number for the sequencing data reported in this paper is GEO: GSE152621. The mim-tRNAseq computational pipeline is available under a GNU public License v3 at https://github.com/nedialkova-lab/mim-tRNAseq. A package description and installation guide are available at https://mim-trnaseq.readthedocs.io/en/latest/.

Experimental Model and Subject Details

Cell Lines and Strains

*S. cerevisiae* cells (BY4741 wild-type, trm7Δ, trm1Δ and trm 10Δ) were grown in yeast extract-peptone-dextrose (YPD) medium. *S. pombe* cells (ED668 h+, ade6-M216 ura4-D18 leu1-32) were cultured in yeast extract with supplements (YES). Overnight cultures were diluted to an optical density 600 ($OD_{600}$) of 0.05, grown at 30 °C at 250 revolutions per minute, and harvested at $OD_{600}$=0.5 by rapid filtration and snap-freezing in liquid nitrogen. *D. melanogaster* BG3-c2 cells were cultured at 26 °C in Schneider's *Drosophila* Medium (GIBCO) supplemented with 10% fetal calf serum, 1% penicillin/streptomycin, and 10 μg/ml human insulin. HEK293T cells were grown at 37 °C and 5% $CO_2$ in DMEM supplemented with 10% fetal bovine serum (Sigma Aldrich). The HPSI0214i-kucg_2 human induced pluripotent stem cell line (obtained from HipSci; Kilpinen et al., 2017) was cultured at 37 °C and 5% $CO_2$ in mTeSR1 (STEMCELL Technologies). K562 cells were grown at 37 °C and 5% $CO_2$ in RPMI 1640 supplemented with 10% fetal calf serum and 2 mM L-Glutamine.

RNA Isolation

RNA from *Drosophila* BG3-c2, HEK293T, and human iPS cells was isolated with Trizol (Sigma Aldrich) according to the manufacturer's instructions. For total RNA isolation from yeast, frozen cells were resuspended in 100 mM sodium acetate pH=4.5, 10 mM EDTA pH=8.0, 1% SDS (1 mL per 50 $OD_{600}$ units). An equal volume of hot acid phenol (pH=4.3) was added, and the cell suspension was vortexed vigorously followed by incubation at 65 °C for 5 min (*S. cerevisiae*) or 45 min (*S. pombe*) with intermittent mixing. After addition of 1/10 volume 1-Bromo-3-chloropropane (BCP, Sigma Aldrich), samples were centrifuged at 10,000×g for 5 min and the aqueous phase was transferred to a new tube. Following an additional round of hot acid phenol/BCP and a round of BCP only extraction, RNA was precipitated from the aqueous phase by the addition of 3 volumes of 100% ethanol. Pellets were washed in 80% ethanol, briefly air-dried, and resuspended in RNase-free water. For RNA isolation from yeast under conditions that preserve tRNA charging, frozen cells were resuspended in ice-cold 100 mM sodium acetate pH=4.5, 10 mM EDTA pH=8.0. One volume of cold acid phenol (pH=4.3) was added and cells were lysed with 500 μm-diameter glass beads by three rounds of vortexing for 45 s with a 1-min incubation on ice in between. One-tenth volume of BCP was then added and the samples were centrifuged at 10,000×g/4 °C for 5 min, followed by a second round of cold phenol-BCP and one round of BCP-only extraction. RNA was ethanol-precipitated from the aqueous phase and pellets were washed in 80% ethanol containing 50 mM sodium acetate, pH=4.5, briefly air-dried, and resuspended in 50 mM sodium acetate pH=4.5, 1 mM EDTA PH=8.0. RNA concentration was determined with NanoDrop and samples were frozen at −80 °C in single-use aliquots.

RNA Oxidation and β-Elimination

To measure tRNA charging levels, RNA oxidation and β-elimination were performed as described (Evans et al., 2017) with minor modifications. 25 μg of total RNA were resuspended in 10 mM sodium acetate pH 4.5 and oxidized by the addition of freshly prepared $NaIO_4$ to a final concentration of 50 mM in a 58 μL volume for 30 min at 22 °C. The reaction was quenched by addition of 6 μL 1 M glucose for 5 min at 22 °C. RNA was purified with Micro Bio Spin P30 columns (BioRad) followed by two rounds of ethanol precipitation in the presence of 0.3M sodium acetate pH=4.5. Pellets were resuspended in 20 µL RNase-free water and β-elimination was performed by addition of 30 µl 100 mM sodium borate pH=9.5 (freshly prepared) for 90 min at 45 °C. RNA was recovered with Micro Bio Spin P30 columns followed by ethanol precipitation, resuspended in RNase-free water, quantified on a NanoDrop, and stored at −80 °C in single-use aliquots.

tRNA Purification by Gel Size Selection

Two synthetic RNA standards corresponding to *E. coli* tRNA-Lys-UUU with intact 3'-CCA (5'-GGGUCGUUAGCUCAGUUGGUAGAGCAGUUGACUUUUAAUCAAUUGGUCGCAGGUU CGAAUCCUGCACGACCCACCA-3') or a 3'-CC (5'-GGGUCGUUAGCUCAGUUGGUAGAGCAGUUGACUUUUAAUCAAUUGGUCGCAGGUU CGAAUCCUGCACGACCCACC-3') were added to total RNA in a 3:1 molar ratio at 0.06 pmol/µg, followed by incubation at 37 °C in 50 mM Tris-HCl PH=9.0 to deacylate tRNAs. Deacylation was omitted for samples subjected to oxidation and β-elimination. Total RNA was subsequently dephosphorylated with 10 U of T4 PNK (NEB) at 37 °C for 30 min and purified by ethanol precipitation in 0.3M sodium acetate pH=4.5 with 25 µg glycogen (Ambion) as a carrier. RNA was resolved on a denaturing 10% polyacrylamide/7M urea/1×TBE gel alongside Low Range ssRNA marker (NEB) and visualized with SYBR Gold. Species migrating at the size range of mature tRNAs (60-100 nt) were excised and gel slices were crushed with disposable pestles. Low-retention tubes and tips (Biotix, Axygen) were used for all subsequent steps of sequencing library construction to maximize nucleic acid recovery. Following addition of 400 µl gel elution buffer (0.3M sodium acetate pH=4.5, 0.25% SDS, 1 mM EDTA pH=8.0), the gel slurry was incubated at 65 °C for 10 min, snap-frozen on dry ice, and thawed at 65 °C for 5 min. RNA was eluted overnight at room temperature with continuous mixing. Gel pieces were removed with Costar Spin-X centrifuge tube filters and RNA was recovered from the flow-through by ethanol precipitation in the presence of 25 µg of glycogen. This protocol typically recovers 5%-10% of total RNA in the 60-100 nt fraction, consistent with estimates of tRNA proportions in cells (Warner, 1999).

3' Adapter Ligation 50 to 200 ng of gel-purified tRNA was ligated to one of four adapters with distinct barcodes:

I1: 5'-pGATATCGTCAAGATCGGAAGAGCACACGTCTGAA/ddC/-3';

I2: 5'-pGATAGCTACAAGATCGGAAGAGCACACGTCTGAA/ddC/-3';

I3: 5'-pGATGCATACAAGATCGGAAGAGCACACGTCTGAA/ddC/-3';

I4: 5'-pGATTCTAGCAAGATCGGAAGAGCACACGTCTGAA/ddC/-3' (barcodes italicised; underlined sequence complementary to RT primer). The adapters are blocked by the 3' chain terminator dideoxycytidine to prevent concatemer formation, and 5'-phosphorylated to enable pre-adenylation by Mth RNA ligase prior to ligation (McGlincy and Ingolia, 2017). Ligation was performed for 3 hours at 25 °C in a 20-µl reaction volume containing pre-adenylated adapter and RNA substrate in a 4:1 molar ratio, 1×T4 RNA Ligase Reaction Buffer, 200 U of T4 RNA ligase 2 (truncated KQ; NEB), 25% PEG 8000, and 10 U SUPERase In (Ambion). Ligation products were separated from excess adapter on denaturing 10% polyacrylamide/7M urea/1×TBE gels. Bands migrating at 95-125 nt were excised and ligation products were recovered from crushed gel slices.

Reverse Transcription

All reactions contained 125 nM primer, 125 nM template and 500 nM TGIRT (InGex) or 200 U Superscript III (Invitrogen). To prime reverse transcription in template-switching reactions, a synthetic RNA/DNA duplex with a single-nucleotide 3' overhang was generated by annealing an RNA oligonucleotide (5'-GAGCACACGUCUGAACUCCACUCUUUCCCUACACGACGCUCUUCCGAUCU-3') to a DNA oligonucleotide (5'-PRAGATCGGAAGAGCGTCGTGTAGGGAAAGAGTGGAGTTCAGACGTGTGCTCN-3'). The DNA oligonucleotide contained a phosphorylated A/G at its 5' end, which is a preferred substrate for CircLigase used in subsequent cDNA circularization (Heyer et al., 2015; McGlincy and Ingolia, 2017). For primer-dependent reverse transcription reactions, adapter-ligated RNA and RT primer (5'-pRNAGATCGGAAGAGCGTCGTGTAGGGAAAGAG/iSp18/GTGACTGGAGTTCAGACGTG TGCTC-3'; underlined sequence complementary to 3' adapter, 5'-RN to ameliorate potential biases during circularization) were mixed in MAXYMum Recovery PCR Tubes (Axygen), denatured at 82 °C for 2 min and annealed at 25 °C for 5 min in a Thermocycler. TGIRT reactions were assembled in a 20-µl final volume by combining template and primer with 10 U SUPERase In, 5 mM DTT (from a freshly made 100 mM stock) and manufacturer-recommended TGIRT buffer (20 mM Tris-HCl PH=7.6, 450 mM NaCl, 5 mM $MgCl_2$) or low salt buffer (50 mM Tris-HCl PH=8.3, 75 mM KCl, 3 mM $MgCl_2$). After TGIRT addition, samples were pre-incubated at reaction temperature for 10 min (primer-dependent reactions) or 22 °C for 30 min (template-switching reactions), initiated by addition of dNTPs to a final concentration of 1.25 mM, and incubated in a Thermocycler for 1 hour or 16 hours. For Superscript III RT, template and primer were denatured at 75 °C for 5 min and chilled on ice, and reverse transcription was performed in the presence of 1× First-Strand Buffer, 5 mM DTT, 0.5 mM dNTPs, 10 U SUPERase In, and 200 U Superscript III (Invitrogen) at 57 °C for 60 min.

Template RNA was subsequently hydrolyzed by the addition of 1 µl 5M NaOH and incubation at 95 °C for 3 min and reaction products were separated from unextended primer on denaturing 10% polyacrylamide/7M urea/1×TBE gels. Gels were stained with SYBR Gold, the region between 60 and 150 nt was excised and cDNA was eluted from crushed gel slices in 400 µl 10 mM Tris-HCl PH=8.0, 1 mM EDTA at 70 °C/2000 rpm for 1 hour in a Thermoblock, followed by ethanol precipitation in 0.3M sodium acetate pH=5.5 in the presence of 25 µg glycogen.

cDNA Circularization and Library Construction PCR

Purified cDNA was circularized with CircLigase ssDNA ligase (Lucigen) in 1× reaction buffer supplemented with 1 mM ATP, 50 mM $MgCl_2$, and 1M betaine for 3 hours at 60 °C, followed by enzyme inactivation for 10 min at 80 °C. One-fifth of circularized cDNA was directly used for library construction PCR with a common forward (5' AATGATACGGCGACCACCGAGATCTACACTCTTTCCCTACACGACGCT·C-3') and (5'-unique indexed reverse primers CAAGCAGAAGACGGCATACGAGATNNNNNNGTGACTGGAGTTCAGACGTGT·G-3', asterisks denote a phosphorothioate bond and NNNNNN corresponds to the reverse complement of an Illumina index sequence). Amplification was performed with KAPA HiFi DNA Polymerase (Roche) in 1× GC buffer with initial denaturation at 95 °C for 3 min, followed by five to six cycles of 98 °C for 20 s, 62 °C for 30 s, 72 °C for 30 s at a ramp rate of 3 °C/sec. PCR products were purified with DNA Clean&Concentrator 5

(Zymo Research) and resolved on 8% polyacrylamide/1× TBE gels alongside pBR322 DNA-Mspl Digest (NEB). The 130-220 bp region of each lane was excised and DNA was eluted from crushed gel slices in 400 µl water with continuous mixing at room temperature overnight. After ethanol precipitation in 0.3M sodium acetate pH=5.5 and 25 µg glycogen, libraries were dissolved in 10 µl 10 mM Tris-HCl pH=8.0, quantified with the Qubit dsDNA HS kit, and sequenced for 150 cycles on an Illumina NextSeq platform.

Northern Blotting

Two micrograms of total RNA were resolved on denaturing 10% polyacrylamide/7M urea/1×TBE gels. RNA was transferred to Immobilon NY+membranes (Millipore) in 1×TBE for 40 min at 4 mA/cm$^2$ on a TransBlot Turbo semi-dry blotting apparatus (Bio-Rad) and crosslinked at 0.04 J in a Stratalinker UV crosslinker. Membranes were incubated at 80 °C for one hour and pre-hybridized in 20 mM $Na_2HPO_4$ PH=7.2, 5×SSC, 7% SDS, 2×Denhardt, 40 µg/ml sheared salmon sperm DNA at 55 °C for 4 hours. The buffer was exchanged 10 pmol and 5'-end $^{32}$P-labeled probe (Arg-UCU-4: 5'-CGGAACCTCTGGATTAGAAGTCC-AGCGCGCTCGTCC-3'; Gly-CCC-2: 5'-CGGGTCGCA-AGAATGGGAATCTTGCATGATAC-3') was added, followed by hybridization at 55 °C overnight. Membranes were washed three times in 25 mM $Na_2PO_4$ PH=7.5, 3×SSC, 5% SDS, 10×Denhardt, once in 1×SSC, 10% SDS, and exposed to PhosphorImager screens, which were subsequently scanned on a Typhoon FLA 9000 (GE Healthcare). Band intensity was quantified with ImageQuant (GE Healthcare).

Primer Extension Analysis of m$^1$G37

The extent of RT arrest at m$^1$G37 in tRNA-Leu-UAA and tRNA-Pro-UGG from *S. cerevisiae* was quantified via primer extension with AMV RT, an enzyme with low processivity at this modification (Werner et al., 2020). The primers were designed to enable a 4-nucleotide extension to m$^1$G37 (tRNA-Leu-UAA: 5'-CGCGGACAACCGTC-CAAC-3'; tRNA-Pro-UGG: 5'-TGAACCCAGGGCCTCT-3') and 5'-end-labeled with γ-32P-ATP. 3 µg of total RNA from exponentially growing yeast cells was mixed with 1 pmol end-labeled primer and incubated at 95 °C for 3 min followed by slow cooling to 37 °C. RT reactions were assembled by adding 15 U AMV RT (Promega), 0.5 mM dNTPs, 20 U SUPERase In (Ambion) and 1×AMV RT buffer in a 5-µl volume. Following incubation at 37 °C for 45 min, reactions were stopped by addition of 5 µl 2×RNA loading dye (47.5% Formamide, 0.01% SDS, 0.01% bromophenol blue, 0.005% Xylene Cyanol, 0.5 mM EDTA), boiled at 95 °C for 5 min, and resolved on a denaturing 15% PAA/7M urea/1×TBE gel. The gel was exposed at −80 °C to a PhosphorImager screen, which was scanned on a Typhoon FLA 9000 (GE Healthcare). Band intensity was quantified with ImageQuant (GE Healthcare).

Read Preprocessing

Sequencing libraries were demultiplexed using cutadapt v2.5 (Martin, 2011) and a fasta file (barcodes.fa) of the first 10 nt for the four different 3' adapters (see 3' adapter ligation above). Indels in the alignment to the adapter sequence were disabled with --no-indels. Following demultiplexing, reads were further trimmed to remove the two 5'-RN nucleotides introduced by circularization from the RT primer with-u 2. In both processing steps, reads shorter than 10 nt were discarded using-m 10. Example commands for demultiplexing and 5' nucleotide trimming:

cutadapt --no-indels-a file: barcodes.fa -m 10 -o mix1_{name}_trim.fastq.gz mix.fastq.gz cutadapt -j 40 -m 10 -u 2 -o mix1_barcode1_trimFinal.fastq.gz mix1_barcode1_trim.fastq.gz Modification Indexing and Clustering mim-tRNAseq uses modification data from MODOMICS (Boccaletto et al., 2018) to guide accurate alignment of short reads from tRNAs. A prepackaged set of data is available for *S. cerevisiae, S. pombe, C. elegans, D. melanogaster, M. musculus, H. sapiens* and *E. coli*, and can be specified with the-species parameter. For other organisms, mim-tRNAseq requires a fasta file of predicted genomic tRNA sequences (-t) and a tRNAscan-SE “out” file containing information about tRNA introns (-o), both of which should be obtained from GtRNAdb (Chan and Lowe, 2016) or from running tRNAscan-SE (Lowe and Chan, 2016) on the genome of interest. Lastly, a user-generated sample input file is required which contains two tab-separated columns specifying the path to trimmed tRNAseq reads in fastq format, and the experimental condition of each fastq file. Additionally, a mitochondrial tRNA fasta reference is supplied with the prepackaged data inputs listed above, or may be supplied (-m) for custom genomes as a fasta file obtained from mitotRNAdb (Jühling et al., 2009). mim-tRNAseq automatically removes nuclear-encoded mitochondrial tRNAs (nmt-tRNAs) and tRNA species with undetermined anticodons (where applicable), generates mature, processed tRNA sequences (with appended 3'-CCA if necessary, 5'-G for tRNA-His, and spliced introns), and fetches species-matched MODOMICS entries accordingly. Transcript sequences are then matched to MODOMICS entries using BLAST in order to index all known instances of residues modified at the Watson-Crick face within each tRNA. An additional modifications file for modifications reported in the literature but not yet added to MODOMICS may be supplied and is automatically processed by the pipeline (e.g., 134 annotation; Arimbasseri et al., 2015; Torres et al., 2015). tRNA clustering is enabled with the --cluster parameter, which utilizes the usearch --cluster_fast algorithm (Edgar, 2010) to cluster tRNA sequences by a user-defined sequence identity threshold (customizable with --cluster-id). Regardless of the chosen threshold, only tRNAs sharing an anticodon are clustered to maintain isoacceptor resolution in cases where tRNA transcripts differ by a single nucleotide in the anticodon. The clusters are re-centered based on the number of identical sequences, and this is used to re-cluster and improve the selection of a representative centroid/parent sequence for each cluster (https://www.drive5.com/usearch/manual7/recenter.html). Polymorphisms between cluster members are recorded, and mismatches at these sites during alignment are tolerated, but they are not included in misincorporation analysis for modified sites. Since inosine is interpreted as a G during reverse transcription, annotated inosines are changed to G in tRNA reference sequences.

Read Alignment and Modification Discovery

After clustering, reads are aligned using GSNAP to the representative centroid cluster sequences of mature tRNA transcripts. By enabling SNP-tolerant alignment with --snp-tolerance, the indexed modified sites are treated as pseudo-SNPs to allow modification-induced mismatches at these sites in a sequence- and position-specific manner. Soft-clipping during alignment in combination with the GSNAP parameter --ignore-trim-in-filtering=1 ensures that non-templated nucleotide extensions are not counted as mismatches during alignment. Mismatch tolerance outside of indexed SNPs is controlled using the --max-mismatches parameter, where an integer of allowed mismatches per read can be provided, or a relative mismatch fraction of read length between 0.0 and 0.1 can be supplied (default 0.1). If --remap is specified, then misincorporation analysis is performed and new, unannotated modifications are called where --misinc-thresh (total misincorporation proportion at a residue; default is 0.1 or 10%) and --min-cov (minimum total coverage for a cluster) regulate the calling of new modifications, which exclude mismatch sites between cluster members appearing as misincorporations in this analysis. The existing SNP index is then updated with these new sites, and realignment of all reads is performed with a mismatch tolerance set using --remap-mismatches. New potential inosine sites are classified for position 34 where a reference A nucleotide is misincorporated with a G in 95% or more total misincorporation events. Both --remap and --max-mismatches are extremely useful for detecting unknown modifications in poorly annotated tRNAs, subsequently allowing more accurate and efficient read alignment, which improves the results of all downstream analyses. Users should consider a low mismatch tolerance during remap to avoid inaccuracy resulting from lenient alignment parameters. a relative mismatch fraction of 0.075 during remapping (--remap-mismatches 0.075) is recommended. Only uniquely mapped reads are retained for post-alignment analyses.

Read Deconvolution

This process aims to recapitulate the single-transcript resolution of--cluster-id 1 (see above), but with the alignment accuracy and decreased multi-mapping achieved at lower--cluster-id values. The deconvolution algorithm first searches each cluster of tRNA reference sequences for single-nucleotide differences that distinguish among cluster members. For this, each nucleotide in a reference sequence is assessed for uniqueness at that position when compared to all other reference sequences in the cluster. If a nucleotide is unique in position and identity for a specific tRNA reference in the cluster, it is catalogued. Then, after alignment, each read is assessed for mismatches to the cluster parent to which it was aligned. These are then scanned individually to find potential matches to the previously catalogued set for the cluster which can distinguish unique tRNA references. Based on the presence and identity of a unique distinguishing mismatch, a read is then be assigned to a specific tRNA reference within a cluster. Depending on the organism and/or cluster ID threshold, unique distinguishing mismatches may not always be present for all tRNA references in a cluster. Reads without distinguishing mismatches remain assigned to the cluster parent, which is then marked as not fully deconvolved. Using this algorithm, uniquely aligned reads are assigned to individual tRNA sequences in the reference (where possible) before any of the downstream analyses detailed below. For differential expression analyses of reads summed per tRNA anticodon, read deconvolution is not necessary and therefore not performed.

Modification, RT Stop, Readthrough and 3' CCA End Analyses

Following read deconvolution, all other mismatched positions for the read are extracted from alignment records in bam files, and converted into positions relative to the unique transcript to which the read was assigned (or the cluster parent if definitive assignment is not possible). The identity of the misincoporated nucleotide is recorded to enable signature analysis, and the counts of mismatches for each of the four nucleotides for all reads with the misincorporation are normalized relative to total read coverage at that position. Stops during reverse transcription are extracted from the alignment start position of each read relative to the reference (5' read ends correspond to cDNA 3' ends during RT) and normalized to total read counts for the unique tRNA. Similarly, readthrough for each position is calculated as the fraction of reads that stop at a position relative to read coverage at each position (as opposed to stop proportions which are normalized to total tRNA read coverage). This value is then subtracted from one to estimate the proportion of reads per position that extend beyond that site, and the minimum value in a 3-nucleotide window centered around the modification is recorded. Using a 3-nucleotide window ensures that potential variance in the position at which the RT stalls due to the modification is accounted for. Taking the minimum value of readthrough for these 3 nucleotides reduces the likelihood of readthrough overestimation. Misincorporation, stop data, and readthrough per unique tRNA sequence, per position are output as tab-separated files, and global heatmaps showing misincorporation and stop proportions across all unique tRNA sequences are plotted per experimental condition. Misincorporation signatures are also plotted for well-known conserved modified tRNA sites (9, 20, 26, 32, 34, 37 and 58) separated by upstream and downstream sequence context to assess potential factors influencing misincorporation signatures. Lastly, the dinucleotide at the 3' ends of reads is quantified, so long as the read aligns to the conserved 3'-CCA tail of the reference. Proportions of transcripts with absent 3' tails, 3'-C, 3'-CC and 3'-CCA are calculated per unique tRNA sequence and plotted pairwise between conditions for quantitation and comparison of functional tRNA pools, or tRNA charging fractions in periodate oxidation experiments.

Post-Alignment Analyses

The cluster deconvolution algorithm allows coverage analysis, novel modification discovery and read counting for tRNA quantitation to be done at the level of unique tRNA sequences. Coverage is calculated as the depth of reads at all positions across a tRNA sequence and plotted using custom R scripts. Cytosolic tRNAs with low read coverage can be filtered at the coverage analysis step by supplying a minimum coverage threshold to--min-cov. Unique tRNA sequences filtered out here are excluded from all downstream analyses, except differential expression analysis by DESeq2 (Love et al., 2014) where all unique tRNA sequences are included. Normalized coverage (read fraction relative to library size) is plotted per sample in 25 bins across gene length in a metagene analysis. Normalized coverage is also scaled relative to the second last bin to account for potential differences in 3' CCA intactness. Read counts per unique tRNA sequence are summed to calculate read counts per isoacceptor family (all tRNAs sharing an anticodon). These counts are subsequently used by a DESeq2 pipeline for count transformations, sample distance analysis using distance matrix heatmaps, PCA plots, and differential expression analysis at the level of isoacceptor families and unique tRNA transcripts (only for completely resolved clusters). In the case that only one experimental condition is supplied, or if there are no replicates for one or more conditions, differential expression analysis is not performed on these samples, but a normalized counts table is still produced for investigations into tRNA abundance.

Data Analysis with the Mim-tRNAseq Package

The following parameters were used for the analysis of mim-tRNAseq generated sequencing datasets (see mimseq--help or https://mim-trnaseq.readthedocs.io/en/latest/intro.html for full explanations of parameters; package version v0.2.5.6):

*S. cerevisiae*: --cluster --cluster-id 0.90 --snp-tolerance --min-cov 2000 --max-mismatches 0.1 --control-condition Exp --cca-analysis --remap --remap-mismatches 0.075

*S. pombe*: --cluster --cluster-id 0.95 --snp-tolerance --min-cov 2000 --max-mismatches 0.1 --control-condition Exp --cca-analysis --remap --remap-mismatches 0.075

*D. melanogaster*: --cluster --cluster-id 0.95 --snp-tolerance --min-cov 2000 --max-mismatches 0.1 --control-condition bg3 --cca-analysis --remap --remap-mismatches 0.075

*H. sapiens*: --snp-tolerance --cluster --cluster-id 0.95 --min-cov 2000 --max-mismatches 0.1 --control-condition kiPS --cca-analysis --remap --remap-mismatches 0.075 tRNA Read Alignment with Bowtie and Bowtie 2

To test previously used alignment strategies as in DM-tRNAseq (Zheng et al., 2015) or ARM-seq (Cozen et al., 2015), a non-redundant set of reference human tRNA transcripts was created by fetching the full set of 610 predicted tRNA genes for human genome hg19 from GtRNAdb (Chan and Lowe, 2016) and the 22 mitochondrially encoded human tRNA genes from mitotRNAdb (Juhling et al., 2009). Following intron removal and addition of 3' CCA (for nuclear-encoded transcripts) and 5'-G (for tRNA-His), a curated set of 596 genes (excluding anticodon/isotype mismatch and nuclear-encoded mitochondrial tRNAs) were collapsed into 420 unique sequences. Corresponding Bowtie and Bowtie 2 indices were built from this set of references. Bowtie alignment was performed with a maximum of 3 allowed mismatches per read (-v 3), filtering for uniquely aligning reads (-m 1) and ensuring the best alignment from the best stratum (i.e., reads with the least number of mismatches) were reported (--best --strata). Bowtie 2 alignments were performed in very sensitive local mode (--very-sensitive --local) and up to 100 alignments per read were allowed (-k 100). Read quality scores were ignored for alignment score and mismatch penalty calculation (--ignore-quals) with increased penalties for ambiguous characters ("N") in reference or read (--np 5). Output alignments in SAM format were reordered to match read order in input fastq file (--reorder). The alignment commands for both algorithms are given below:

bowtie-v 3 -m 1 --best --strata --threads 40-S bowtie2 --local-x-k 100 --very-sensitive --ignore-quals --np 5 --reorder-p 40-U QuantM-tRNAseq data for HEK293 T-Rex Flp-IN cells downloaded from the NCBI Gene Expression Omnibus repository was adapter-trimmed and analyzed with Bowtie 2 as described in (Pinkard et al., 2020):

bowtie2 --local --score-min G, 1,8 -D 20 -R 3 -N 1 -L 10 -i S, 1, 0.5

Sequence Logo Analysis

Alignment files for uniquely aligned reads from human HEK293T and *S. cerevisiae* cells were utilized to generate frequency plots of untemplated nucleotide additions by TGIRT, and 5' sequence logos in each sample. Briefly, CIGAR strings for each unique alignment were assessed for GSNAP soft-clipped nucleotides representing untemplated additions. The number of additions per read were recorded and plotted as frequency histograms. Since a total of 3 additions or less were present in >90% of reads analyzed, sequence logos were generated using the Python package Logomaker (Tareen and Kinney, 2020) for these reads using soft-clipped residues and the first 10 nucleotides after them. For the logo representing all cataloged tRNA genes, mature tRNA transcript sequences was used from each genome present in GtRNAdb, and generated a multiple sequence alignment of these using Infernal (Nawrocki and Eddy, 2013). A sequence logo was then generated from the first 11 nucleotides of each aligned tRNA transcript (in order to include G-1 for tRNA-His, plus 10 additional nucleotides as in the uniquely aligned read logo above).

Differential Modification Analysis

To test for global differential modification between two conditions, first, misincorporation proportion and coverage data generated by mim-tRNAseq were used to calculate absolute counts of modified and unmodified bases per position for each resolved tRNA transcript. Then, log odds ratios (log OR) were calculated for each position, x, as follows:

$$\log ORx = \log\left((M_a/M_b)/(U_a/U_b)\right)$$

where $M_a$ and $M_b$ are the counts of modified nucleotides at position x in condition a and b, and $U_a$ and $U_b$ are the counts of unmodified nucleotides at position x in condition a and b, respectively. Significance for each log OR was determined with chi-square tests using the respective modified and unmodified nucleotide counts for each condition in a two-dimensional contingency table for the Pearson's chi-square test. Correction for multiple testing was performed with the FDR method. Following significance tests, log OR values were filtered for FDR-adjusted p values ≤0.01, absolute log 2 fold-changes ≥1, and total misincorporation at the given position of 10% or more in at least one of the conditions to ensure only sites with high-confidence misincorporation levels are kept. The resulting log OR were used in generating heatmaps for individual contrasts between cell types or experimental conditions.

REFERENCES

Anderson J., Phan L., Cuesta R., Carlson B. A., Pak M., Asano K., Björk G. R., Tamame M., Hinnebusch A. G. The essential Gcd10p-Gcd14p nuclear complex is required for 1-methyladenosine modification and maturation of initiator methionyl-tRNA. *Genes Dev.* 1998; 12:3650-3662.

Arimbasseri A. G., Blewett N. H., Iben J. R., Lamichhane T. N., Cherkasova V., Hafner M., Maraia R. J. RNA Polymerase Ill output is functionally linked to tRNA dimethyl-G26 modification. *PLOS Genet.* 2015; 11:e1005671.

Arimbasseri A. G., Iben J., Wei F. Y., Rijal K., Tomizawa K., Hafner M., Maraia R. J. Evolving specificity of tRNA 3-methyl-cytidine-32 ($m^3C32$) modification: a subset of tRNAsSer requires N6-isopentenylation of A37. *RNA.* 2016; 22:1400-1410.

Boccaletto P., Machnicka M. A., Purta E., Piatkowski P., Baginski B., Wirecki T. K., de Crécy-Lagard V., Ross R., Limbach P. A., Kotter A. MODOMICS: a database of RNA modification pathways. 2017 update. *Nucleic Acids Res.* 2018; 46 (D1): D303-D307.

Camacho C., Coulouris G., Avagyan V., Ma N., Papadopoulos J., Bealer K., Madden T. L. BLAST+: architecture and applications. *BMC Bioinformatics.* 2009; 10:421.

Chan P. P., Lowe T. M. GtRNAdb 2.0: an expanded database of transfer RNA genes identified in complete and draft genomes. *Nucleic Acids Res.* 2016; 44 (D1): D184-D189.

Chen D., Patton J. T. Reverse transcriptase adds nontemplated nucleotides to cDNAs during 5'-RACE and primer extension. *Biotechniques.* 2001; 30:574-580, 582.

Clark W. C., Evans M. E., Dominissini D., Zheng G., Pan T. tRNA base methylation identification and quantification via high-throughput sequencing. *RNA.* 2016; 22:1771-1784.

Cock P. J. A., Antao T., Chang J. T., Chapman B. A., Cox C. J., Dalke A., Friedberg I., Hamelryck T., Kauff F., Wilczynski B., de Hoon M. J. L. Biopython: freely available Python tools for computational molecular biology and bioinformatics. *Bioinformatics.* 2009; 25:1422-1423.

Cozen A. E., Quartley E., Holmes A. D., Hrabeta-Robinson E., Phizicky E. M., Lowe T. M. ARM-seq: AlkB-facilitated RNA methylation sequencing reveals a complex landscape of modified tRNA fragments. *Nat. Methods.* 2015; 12:879-884.

Dittmar K. A., Mobley E. M., Radek A. J., Pan T. Exploring the regulation of tRNA distribution on the genomic scale. *J. Mol. Biol.* 2004; 337:31-47.

Dittmar K. A., Goodenbour J. M., Pan T. Tissue-specific differences in human transfer RNA expression. *PLOS Genet.* 2006; 2: e221-e229.

Ebhardt H. A., Tsang H. H., Dai D. C., Liu Y., Bostan B., Fahlman R. P. Meta-analysis of small RNA-sequencing errors reveals ubiquitous post-transcriptional RNA modifications. *Nucleic Acids Res.* 2009; 37:2461-2470.

Edgar R. C. Search and clustering orders of magnitude faster than BLAST. *Bioinformatics.* 2010; 26:2460-2461.

Ellis S. R., Morales M. J., Li J. M., Hopper A. K., Martin N. C. Isolation and characterization of the TRM1 locus, a gene essential for the N2, N2-dimethylguanosine modification of both mitochondrial and cytoplasmic tRNA in *Saccharomyces cerevisiae. J. Biol. Chem.* 1986; 261:9703-9709.

Evans M. E., Clark W. C., Zheng G., Pan T. Determination of tRNA aminoacylation levels by high-throughput sequencing. *Nucleic Acids Res.* 2017; 45: e133.

Gamper H. B., Masuda I., Frenkel-Morgenstern M., Hou Y.-M. Maintenance of protein synthesis reading frame by EF-P and m(')G37-tRNA. *Nat. Commun.* 2015; 6:7226.

Gerber A. P., Keller W. An adenosine deaminase that generates inosine at the wobble position of tRNAs. *Science.* 1999; 286:1146-1149.

Gogakos T., Brown M., Garzia A., Meyer C., Hafner M., Tuschl T. Characterizing expression and processing of precursor and mature human tRNAs by hydro-tRNAseq and PAR-CLIP. *Cell Rep.* 2017; 20:1463-1475.

Goodenbour J. M., Pan T. Diversity of tRNA genes in eukaryotes. *Nucleic Acids Res.* 2006; 34:6137-6146.

Gu Z., Eils R., Schlesner M. Complex heatmaps reveal patterns and correlations in multidimensional genomic data. *Bioinformatics.* 2016; 32:2847-2849.

Guy M. P., Podyma B. M., Preston M. A., Shaheen H. H., Krivos K. L., Limbach P. A., Hopper A. K., Phizicky E. M. Yeast $Trm^7$ interacts with distinct proteins for critical modifications of the tRNAPhe anticodon loop. *RNA.* 2012; 18:1921-1933. [

Han L., Guy M. P., Kon Y., Phizicky E. M. Lack of 2'-O-methylation in the tRNA anticodon loop of two phylogenetically distant yeast species activates the general amino acid control pathway. *PLOS Genet.* 2018; 14: e1007288.

Harismendy O., Gendrel C.-G., Soularue P., Gidrol X., Sentenac A., Werner M., Lefebvre O. Genome-wide location of yeast RNA polymerase III transcription machinery. *EMBO J.* 2003; 22:4738-4747.

Hauenschild R., Tserovski L., Schmid K., Thuring K., Winz M.-L., Sharma S., Entian K.-D., Wacheul L., Lafontaine D. L. J., Anderson J. The reverse transcription signature of N-1-methyladenosine in RNA-Seq is sequence dependent. *Nucleic Acids Res.* 2015; 43:9950-9964.

Heyer E. E., Ozadam H., Ricci E. P., Cenik C., Moore M. J. An optimized kit-free method for making strand-specific deep sequencing libraries from RNA fragments. *Nucleic Acids Res.* 2015; 43: e2.

Hoffmann A., Fallmann J., Vilardo E., Morl M., Stadler P. F., Amman F. Accurate mapping of tRNA reads. *Bioinformatics.* 2018; 34:1116-1124

Ishimura R., Nagy G., Dotu I., Zhou H., Yang X.-L., Schimmel P., Senju S., Nishimura Y., Chuang J. H., Ackerman S. L. RNA function. Ribosome stalling induced by mutation of a CNS-specific tRNA causes neurodegeneration. *Science.* 2014; 345:455-459.

Jackman J. E., Montagne R. K., Malik H. S., Phizicky E. M. Identification of the yeast gene encoding the tRNA $m^1G$ methyltransferase responsible for modification at position 9. *RNA.* 2003; 9:574-585.

Jacob D., Thuring K., Galliot A., Marchand V., Galvanin A., Ciftci A., Scharmann K., Stock M., Roignant J.-Y., Leidel S. A. Absolute quantification of noncoding RNA by microscale thermophoresis. *Angew. Chem. Int. Ed. Engl.* 2019; 58:9565-9569.

M., Stadler P. F., Pütz J. tRNAdb 2009: compilation of tRNA sequences and tRNA genes. *Nucleic Acids Res.* 2009; 37: D159-D162.

Karaca E., Weitzer S., Pehlivan D., Shiraishi H., Gogakos T., Hanada T., Jhangiani S. N., Wiszniewski W., Withers M., Campbell I. M., Baylor Hopkins Center for Mendelian Genomics Human CLP1 mutations alter tRNA biogenesis, affecting both peripheral and central nervous system function. *Cell.* 2014; 157:636-650.

Katibah G. E., Qin Y., Sidote D. J., Yao J., Lambowitz A. M., Collins K. Broad and adaptable RNA structure recognition by the human interferon-induced tetratricopeptide repeat protein IFIT5. *Proc. Natl. Acad. Sci. USA.* 2014; 111:12025-12030.

Kilpinen H., Gonçalves A., Leha A., Afzal V., Alasoo K., Ashford S., Bala S., Bensaddek D., Casale F. P., Culley O. J. Common genetic variation drives molecular heterogeneity in human iPSCs. *Nature.* 2017; 546:370-375.

Kirchner S., Ignatova Z. Emerging roles of tRNA in adaptive translation, signalling dynamics and disease. *Nat. Rev. Genet.* 2015; 16:98-112.

Kutter C., Brown G. D., Gonçalves A., Wilson M. D., Watt S., Brazma A., White R. J., Odom D. T. Pol Ill binding in six mammals shows conservation among amino acid isotypes despite divergence among tRNA genes. *Nat. Genet.* 2011; 43:948-955.

Langmead B., Salzberg S. L. Fast gapped-read alignment with Bowtie 2. *Nat. Methods.* 2012; 9:357-359.

Langmead B., Trapnell C., Pop M., Salzberg S. L. Ultrafast and memory-efficient alignment of short DNA sequences to the human genome. *Genome Biol.* 2009; 10: R25.

Li H., Handsaker B., Wysoker A., Fennell T., Ruan J., Homer N., Marth G., Abecasis G., Durbin R., 1000 Genome Project Data Processing Subgroup The sequence alignment/map format and SAMtools. *Bioinformatics.* 2009; 25:2078-2079.

Li X., Xiong X., Zhang M., Wang K., Chen Y., Zhou J., Mao Y., Lv J., Yi D., Chen X.-W. Base-resolution mapping reveals distinct m$^1$A methylome in nuclear- and mitochondrial-encoded transcripts. *Mol. Cell.* 2017; 68:993-1005.e9.

Lin Y.-C., Boone M., Meuris L., Lemmens I., Van Roy N., Soete A., Reumers J., Moisse M., Plaisance S., Drmanac R. Genome dynamics of the human embryonic kidney 293 lineage in response to cell biology manipulations. *Nat. Commun.* 2014; 5:4767.

Love M. I., Huber W., Anders S. Moderated estimation of fold change and dispersion for RNA-seq data with DESeq2. *Genome Biol.* 2014; 15:550.

Lowe T. M., Chan P. P. tRNAscan-SE On-line: integrating search and context for analysis of transfer RNA genes. *Nucleic Acids Res.* 2016; 44 (W1): W54-W57.

Maehigashi T., Dunkle J. A., Miles S. J., Dunham C. M. Structural insights into +1 frameshifting promoted by expanded or modification-deficient anticodon stem loops. *Proc. Natl. Acad. Sci. USA.* 2014; 111:12740-12745.]

Martin M. M. E. Cutadapt removes adapter sequences from high-throughput sequencing reads. *EMBnet. J.* 2011; 17:10-12.

Masuda I., Matsubara R., Christian T., Rojas E. R., Yadavalli S. S., Zhang L., Goulian M., Foster L. J., Huang K. C., Hou Y.-M. tRNA methylation is a global determinant of bacterial multi-drug resistance. *Cell Syst.* 2019; 8:302-314.e8.

McGlincy N. J., Ingolia N. T. Transcriptome-wide measurement of translation by ribosome profiling. *Methods.* 2017; 126:112-129.

Mohr S., Ghanem E., Smith W., Sheeter D., Qin Y., King O., Polioudakis D., lyer V. R., Hunicke-Smith S., Swamy S. Thermostable group II intron reverse transcriptase fusion proteins and their use in cDNA synthesis and next-generation RNA sequencing. *RNA.* 2013; 19:958-970.

Motorin Y., Helm M. Methods for RNA modification mapping using deep sequencing: established and new emerging technologies. *Genes (Basel)* 2019; 10:35.

Motorin Y., Muller S., Behm-Ansmant I., Branlant C. Identification of modified residues in RNAs by reverse transcription-based methods. *Methods Enzymol.* 2007; 425:21-53.

Nawrocki E. P., Eddy S. R. Infernal 1.1:100-fold faster RNA homology searches. *Bioinformatics.* 2013; 29:2933-2935.

Pernod K., Schaeffer L., Chicher J., Hok E., Rick C., Geslain R., Eriani G., Westhof E., Ryckelynck M., Martin F. The nature of the purine at position 34 in tRNAs of 4-codon boxes is correlated with nucleotides at positions 32 and 38 to maintain decoding fidelity. *Nucleic Acids Res.* 2020; 48:6170-6183.

Phizicky E. M., Alfonzo J. D. Do all modifications benefit all tRNAs? *FEBS Lett.* 2010; 584:265-271.

Pinkard O., McFarland S., Sweet T., Coller J. Quantitative tRNA-sequencing uncovers metazoan tissue-specific tRNA regulation. *Nat. Commun.* 2020; 11:4104-4115.

Qin Y., Yao J., Wu D. C., Nottingham R. M., Mohr S., Hunicke-Smith S., Lambowitz A. M. High-throughput sequencing of human plasma RNA by using thermostable group II intron reverse transcriptases. *RNA.* 2016; 22:111-128.

Quail M. A., Otto T. D., Gu Y., Harris S. R., Skelly T. F., McQuillan J. A., Swerdlow H. P., Oyola S. O. Optimal enzymes for amplifying sequencing libraries. *Nat. Methods.* 2011; 9:10-11. Quinlan A. R., Hall I. M. BEDTools: a flexible suite of utilities for comparing genomic features. *Bioinformatics.* 2010; 26:841-842.

Roberts D. N., Stewart A. J., Huff J. T., Cairns B. R. The RNA polymerase III transcriptome revealed by genome-wide localization and activity-occupancy relationships. *Proc. Natl. Acad. Sci. USA.* 2003; 100: 14695-14700.

Ryvkin P., Leung Y. Y., Silverman I. M., Childress M., Valladares O., Dragomir I., Gregory B. D., Wang L. S. HAMR: high-throughput annotation of modified ribonucleotides. *RNA.* 2013; 19:1684-1692.

Safra M., Sas-Chen A., Nir R., Winkler R., Nachshon A., Bar-Yaacov D., Erlacher M., Rossmanith W., Stern-Ginossar N., Schwartz S. The m$^1$A landscape on cytosolic and mitochondrial mRNA at single-base resolution. *Nature.* 2017; 551:251-255.

Sas-Chen A., Schwartz S. Misincorporation signatures for detecting modifications in mRNA: Not as simple as it sounds. *Methods.* 2019; 156:53-59.

Schmitt B. M., Rudolph K. L. M., Karagianni P., Fonseca N. A., White R. J., Talianidis I., Odom D. T., Marioni J. C., Kutter C. High-resolution mapping of transcriptional dynamics across tissue development reveals a stable mRNA-tRNA interface. *Genome Res.* 2014; 24:1797-1807.

Steinberg S., Cedergren R. A correlation between N$^2$-dimethylguanosine presence and alternate tRNA conformers. *RNA.* 1995; 1:886-891.

Swinehart W. E., Henderson J. C., Jackman J. E. Unexpected expansion of tRNA substrate recognition by the yeast m$^1$G9 methyltransferase Trm$^{10}$. *RNA.* 2013; 19:1137-1146.

Tareen A., Kinney J. B. Logomaker: beautiful sequence logos in Python. *Bioinformatics.* 2020; 36:2272-2274.

Torres A. G., Pineyro D., Rodríguez-Escriba M., Camacho N., Reina O., Saint-Léger A., Filonava L., Batlle E., Ribas de Pouplana L. Inosine modifications in human tRNAs are incorporated at the precursor tRNA level. *Nucleic Acids Res.* 2015; 43:5145-5157.

Torres A. G., Reina O., Stephan-Otto Attolini C., Ribas de Pouplana L. Differential expression of human tRNA genes drives the abundance of tRNA-derived fragments. *Proc. Natl. Acad. Sci. USA.* 2019; 116:8451-8456.

Tuller T., Carmi A., Vestsigian K., Navon S., Dorfan Y., Zaborske J., Pan T., Dahan O., Furman I., Pilpel Y. An evolutionarily conserved mechanism for controlling the efficiency of protein translation. *Cell.* 2010; 141:344-354.

Warner J. R. The economics of ribosome biosynthesis in yeast. *Trends Biochem. Sci.* 1999; 24:437-440.

Werner S., Schmidt L., Marchand V., Kemmer T., Falschlunger C., Sednev M. V., Bec G., Ennifar E., Hobartner C., Micura R. Machine learning of reverse transcription signatures of variegated polymerases allows mapping and discrimination of methylated purines in limited transcriptomes. *Nucleic Acids Res.* 2020; 48:3734-3746.

Wu T. D., Nacu S. Fast and SNP-tolerant detection of complex variants and splicing in short reads. *Bioinformatics.* 2010; 26:873-881.

Xu H., Yao J., Wu D. C., Lambowitz A. M. Improved TGIRT-seq methods for comprehensive transcriptome profiling with decreased adapter dimer formation and bias correction. *Sci. Rep.* 2019; 9:7953.

Zhao C., Liu F., Pyle A. M. An ultraprocessive, accurate reverse transcriptase encoded by a metazoan group II intron. RNA. 2018; 24:183-195.

Zheng G., Qin Y., Clark W. C., Dai Q., Yi C., He C., Lambowitz A. M., Pan T. Efficient and quantitative high-throughput tRNA sequencing. *Nat. Methods.* 2015; 12:835-837.

Zhou H., Rauch S., Dai Q., Cui X., Zhang Z., Nachtergaele S., Sepich C., He C., Dickinson B. C. Evolution of a reverse transcriptase to map N1-methyladenosine in human messenger RNA. *Nat. Methods.* 2019; 16:1281-1288.

Zhuang F., Fuchs R. T., Sun Z., Zheng Y., Robb G. B. Structural bias in T4 RNA ligase-mediated 3'-adapter ligation. *Nucleic Acids Res.* 2012; 40: e54.

The invention claimed is:

1. A method for generation of a cDNA library from tRNA comprising (a) optionally ligating at least one DNA adapter to the 3'-end of tRNA under one or more of the following conditions:

(i) crowding reagent at 5% to 35%, (ii) MgCl2 concentration of 1 mM to 15 mM, (iii) a temperature of 12 °C to 37 °C, (iv) a pH of 6.0 to 9.0, (v) reducing agent concentration of 0.1 mM to 10 mM, (vi) a reaction time of at least 30 min; and (b) reverse transcription in a primer-dependent reaction, in case step (a) is present, or in a template-switching reaction, in case step (a) is absent, of the tRNA, under the following conditions:

(i) KCI or NaCl at a concentration of 20 mM to 250 mM, (ii) MgCl2 at a concentration of 0.5 mM to 15 mM, (iii) a temperature of 30 °C to 65 °C, and (iv) a reaction time of at least 2 h, and optionally (v) a pH of 6.5 to 9.5, and/or (vi) a reducing agent (DTT) at a concentration of 1 mM to 12.5 mM.

2. The method of claim 1 further comprising prior to step (a), (a') the purification of tRNAs from an RNA preparation.

3. The method of claim 2 further comprising prior to step (a'), (a") the isolation of an RNA preparation from eukaryotic cells.

4. The method of claim 1, further comprising (c) construction of a sequencing library by PCR amplification of the cDNA(s) as obtained in step (b), wherein the cDNA(s) is/are optionally circularized prior to the amplification.

5. The method of claim 1, wherein the DNA adapter comprises at least two, three or four DNA adapters that are distinguished from each other by a barcode sequence.

6. The method of claim 1, further comprising (d) sequencing the sequencing library as obtained in step (c).

7. The method of claim 6, further comprising (e) aligning sequencing reads as obtained in step (d) to known tRNA reference sequences.

8. The method of claim 6, further comprising (f) aligning sequencing reads as obtained in step (d) to a reference of known tRNA transcript sequences, wherein the reference comprises information on identity and location of known modified ribonucleosides in tRNAs.

9. The method of claim 8, wherein the reads are aligned using a short read alignment algorithm.

10. The method of claim 8, wherein reads are aligned to RNA reference sequences in single nucleotide polymorphism (SNP)-tolerant mode, using known modified ribonucleotides as potential sites of mismatch to the reference sequence.

11. The method of claim 8, further comprising (g) subjecting the reads aligned to clusters to a deconvolution algorithm that assigns the aligned reads to unique tRNA species.

12. The method of claim 8, further comprising after read deconvolution (h) analysis of one or more of read coverage, 3'-CCA, differential tRNA abundance and modification profiling.

13. The method of claim 1, wherein the group II intron reverse transcriptase is a thermostable group II intron reverse transcriptase.

14. The method of claim 13, the thermostable group II intron reverse transcriptase is a TGIRT RT, or a MarathonRT that has the sequence of SEQ ID NO: 6 or a sequence being at least 80% identical thereto.

15. The method of claim 14, wherein TGIRT has the sequence of any one of SEQ ID NOs: 1 to 5 or a sequence being at least 80% identical thereto.

* * * * *